US011066653B2

(12) United States Patent
Felle et al.

(10) Patent No.: US 11,066,653 B2
(45) Date of Patent: Jul. 20, 2021

(54) METHOD OF TRANSFORMING BACTERIAL CELLS

(71) Applicant: BASF SE, Ludwigshafen (DE)

(72) Inventors: Max Fabian Felle, Ludwigshafen (DE); Stefan Seemayer, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/631,994

(22) PCT Filed: Jul. 11, 2018

(86) PCT No.: PCT/EP2018/068846
§ 371 (c)(1),
(2) Date: Jan. 17, 2020

(87) PCT Pub. No.: WO2019/016051
PCT Pub. Date: Jan. 24, 2019

(65) Prior Publication Data

US 2020/0165581 A1 May 28, 2020

(30) Foreign Application Priority Data

Jul. 21, 2017 (EP) .................................. 17182610.0

(51) Int. Cl.
*C12N 15/75* (2006.01)
*C12N 9/10* (2006.01)

(52) U.S. Cl.
CPC ........... *C12N 9/1007* (2013.01); *C12N 15/75* (2013.01)

(58) Field of Classification Search
CPC .............................. C12N 15/75; C12N 9/1007
See application file for complete search history.

(56) References Cited

U.S. PATENT DOCUMENTS

| | | | | |
|---|---|---|---|---|
| 6,689,573 | B1 | 2/2004 | Roberts et al. | |
| 7,820,408 | B2 * | 10/2010 | Thomas | C12P 21/00 435/69.1 |

FOREIGN PATENT DOCUMENTS

| | | | |
|---|---|---|---|
| DE | 4005025 | A1 | 10/1990 |
| EP | 0618295 | A1 | 10/1994 |
| EP | 2089516 | A2 | 8/2009 |
| WO | WO-2008/067423 | A2 | 6/2008 |
| WO | WO-2019/016052 | A1 | 1/2019 |

OTHER PUBLICATIONS

"RecName: Full-Cytosine-specific Methyltransferase {ECO:0000256:RuleBase:RU000417}; EC=2.1.1.37 {ECO:0000256:RuleBase:RU000417};", Database UniProt [Online], XP55408366, Database accession No. F1KC48, May 3, 2011, 2 pages.

"RecName: Full-Cytosine-specific methyltransferase,{EC0:0000256:RuleBase:RU000417}; EC=2.1.1.37 {EC0:0000256:RuleBase:RU000417}", Database UniProt [Online], XP55408419, Database accession No. A0A1T1DCH1, May 10, 2017, 2 pages.

Barker, et al., "Pathway of lysine degradation in Fusobacterium nucleatum", Journal of Bacteriology, vol. 152, Issue 1, Oct. 1982, pp. 201-207.

Blow, et al., "The Epigenomic Landscape of Prokaryotes", PLOS Genetics, vol. 12, Issue 5, Feb. 12, 2016, 28 pages.

Braunstein, et al., "Two Nonredundant SecA Homologues Function in Mycobacteria", Journal of Bacteriology, vol. 183, Issue 24, Dec. 1, 2001, pp. 6979-6990.

European Search Report for EP Patent Application No. 17182610.0, dated Sep. 29, 2017, 4 pages.

Feltcher, et al., "Emerging themes in SecA2-mediated protein export", Nature Reviews Microbiology, vol. 10, Issue 11, Sep. 24, 2012, pp. 779-789.

Feyter, et al., "Use of Cloned DNA Methylase Genes to Increase the Frequency of Transfer of Foreign Genes into Xanthomonas Campestris pv. Malvacearum", Journal of Bacteriology American Society for Microbiology, vol. 173, Issue 20, Oct. 1991, pp. 6421-6427.

Green, et al., "Bacterial Secretion Systems: An Overview", Microbiology spectrum 4.1, Apr. 9, 2016, 32 pages.

International Search Report and Written Opinion for PCT Patent Application No. PCT/EP2018/068846, dated Sep. 4, 2018.

Lubys , et al., "Cloning and analysis of the plasmid-borne genes encoding the Bsp6l restriction and modification enzymes", Gene, vol. 157, Issue 1-2, May 19, 1995, pp. 25-29.

Madsen, et al., "Cloning and Characterization of the Lactococcal Plasmid-Encoded Type II Restriction/Modification System, LlaDII", Applied and Environmental Microbiology, vol. 64, Issue 7, Jul. 1998, pp. 2424-2431.

Pfeifer, et al., "Isolation and characterisation of DNA cytosine 5-methyltransferase from human placenta", Biochimica et Biophysica Acta (BBA)—Gene Structure and Expression, vol. 740, Issue 3, Aug. 2, 1983, pp. 323-330.

(Continued)

*Primary Examiner* — Tekchand Saidha
(74) *Attorney, Agent, or Firm* — Marshall, Gerstein & Borun LLP

(57) ABSTRACT

The present invention is directed to a producing a DNA methyltransferase in a recombinant host cell, wherein the DNA methyltransferase methylates DNA resulting in a DNA containing 5-methylcytosine within the recognition sequence GCNGC and wherein the DNA methyltransferase comprises less than (35) amino acid residues between amino acid residue (72) and amino acid residue (106) according to the numbering of SEQ ID NO: 33. Furthermore, the present invention is directed to the use of such DNA methyltransferase for the production of bacterial transformants comprising the steps of (a) introducing into a first bacterial host cell a polynucleotide comprising a polynucleotide sequence encoding the DNA methyltransferase to produce a methylated DNA and (b) transferring the methylated DNA from the first bacterial host cell into a second bacterial host cell, wherein the second bacterial host cell comprises a restriction endonuclease able to degrade the DNA but unable to degrade the methylated DNA.

5 Claims, 4 Drawing Sheets

Specification includes a Sequence Listing.

(56) References Cited

OTHER PUBLICATIONS

Richhardt, et al., "An improved transconjugation protocol for Bacillus megaterium facilitating a direct genetic knockout", Applied Microbiology and Biotechnology, vol. 86, Mar. 10, 2010, pp. 1959-1965.
Roberts, et al., "REBASE—a database for DNA restriction and modification: enzymes, genes and genomes", Nucleic Acids Research, vol. 43, Issue D1, Jan. 28, 2015, pp. D298-D299.
Schafer, et al., "High-frequency conjugal plasmid transfer from gram-negative *Escherichia coli* to various gram-positive coryneform bacteria", Journal of Bacteriology, vol. 172, Issue 3, Mar. 1990, pp. 1663-1666.

* cited by examiner

SEQUENCE LISTING

<160> NUMBER OF SEQ ID NOS: 118

<210> SEQ ID NO 1
<211> LENGTH: 27
<212> TYPE: DNA
<213> ORGANISM: Artificial Sequence
<220> FEATURE:
<223> OTHER INFORMATION: PCR-amplification of fragment of pCB56C

<400> SEQUENCE: 1
aggaagagct cggtacccga cgatcat 27

<210> SEQ ID NO 2
<211> LENGTH: 37
<212> TYPE: DNA
<213> ORGANISM: Artificial Sequence
<220> FEATURE:
<223> OTHER INFORMATION: PCR-amplification of fragment of pCB56C

<400> SEQUENCE: 2
gaggagtacg taaaatcttt ttgttccatt aaagggc 37

<210> SEQ ID NO 3
<211> LENGTH: 30
<212> TYPE: DNA
<213> ORGANISM: Artificial Sequence
<220> FEATURE:
<223> OTHER INFORMATION: PCR-amplification of fragment of pUB110

<400> SEQUENCE: 3
gacctctacg taaccaacat gattaacaat 30

<210> SEQ ID NO 4
<211> LENGTH: 30
<212> TYPE: DNA
<213> ORGANISM: Artificial Sequence
<220> FEATURE:
<223> OTHER INFORMATION: PCR-amplification of fragment of pUB110

<400> SEQUENCE: 4
ggatcgagct cccaagaaaa acacgattta 30

<210> SEQ ID NO 5
<211> LENGTH: 33
<212> TYPE: DNA
<213> ORGANISM: Artificial Sequence
<220> FEATURE:
<223> OTHER INFORMATION: PCR-amplification of fragment of pBR322

<400> SEQUENCE: 5
ccatgtacgt agtggcactt ttcggggaaa tgt 33

<210> SEQ ID NO 6
<211> LENGTH: 30
<212> TYPE: DNA
<213> ORGANISM: Artificial Sequence
<220> FEATURE:
<223> OTHER INFORMATION: PCR-amplification of fragment of pBR322

<400> SEQUENCE: 6
ccaggatatc tgagcaaaag gccagcaaaa 30

<210> SEQ ID NO 7
<211> LENGTH: 37
<212> TYPE: DNA
<213> ORGANISM: Artificial Sequence
<220> FEATURE:
<223> OTHER INFORMATION: PCR-amplification of fragment of lacI from pZS4-int1

<400> SEQUENCE: 7
aggccggtac ctataaaaat aggcgtatca cgaggcc 37

<210> SEQ ID NO 8
<211> LENGTH: 33
<212> TYPE: DNA
<213> ORGANISM: Artificial Sequence
<220> FEATURE:
<223> OTHER INFORMATION: PCR-amplification of fragment of lacI from pZS4-int1

<400> SEQUENCE: 8
aactcctcta gattaattgc gttgcgctca ctg 33

<210> SEQ ID NO 9
<211> LENGTH: 41
<212> TYPE: DNA
<213> ORGANISM: Bacilllus licheniformis

<400> SEQUENCE: 9
aattgtttgg aaatgacaaa aggtatgata tgatattgca t 41

<210> SEQ ID NO 10
<211> LENGTH: 249
<212> TYPE: DNA
<213> ORGANISM: Artificial Sequence
<220> FEATURE:
<223> OTHER INFORMATION: Synthetic DNA fragment comprising the B.licheniformis promoter of secA gene followed by cloning site and terminator

<400> SEQUENCE: 10
ctcgagaatt gtttggaaat gacaaaaggt atgatatgat attgcatata tcgagaccat 60
tttctccagc ctgcttttcc atgcgggctg ccgcttatcg tggtctcaag cttagtgact 120
gagcttggac tcctgttgat agatccagta atgacctcag aactccatct ggatttgttc 180
agaacgctcg gttgccgccg ggcgtttttt attggtgaga atccaagcta ggttggcgag 240
atttctaga 249

<210> SEQ ID NO 11
<211> LENGTH: 81
<212> TYPE: DNA
<213> ORGANISM: Artificial Sequence
<220> FEATURE:
<223> OTHER INFORMATION: T5-promoter with lac-operator sites

<400> SEQUENCE: 11
aaatcataaa aaatttattt gctttgtgag cggataacaa ttataataga ttcaattgtg 60
agcggataac aatttcacac a 81

<210> SEQ ID NO 12
<211> LENGTH: 289
<212> TYPE: DNA
<213> ORGANISM: Artificial Sequence
<220> FEATURE:
<223> OTHER INFORMATION: Synthetic DNA fragment comprising the T5-promoter with lac-operator sites followed by cloning site and terminator

<400> SEQUENCE: 12
ctcgagaaat cataaaaaat ttatttgctt tgtgagcgga taacaattat aatagattca 60
attgtgagcg gataacaatt tcacacaata tcgagaccat tttctccagc ctgcttttcc 120
atgcgggctg ccgcttatcg tggtctcaag cttagtgact gagcttggac tcctgttgat 180
agatccagta atgacctcag aactccatct ggatttgttc agaacgctcg gttgccgccg 240
ggcgtttttt attggtgaga atccaagcta ggttggcgag attggtacc 289

<210> SEQ ID NO 13
<211> LENGTH: 59
<212> TYPE: DNA
<213> ORGANISM: Bacillus licheniformis

<400> SEQUENCE: 13
atataaaaat tactgtttac tcatgcttaa acaaggaaat taaagaggag cgttattct 59

<210> SEQ ID NO 14
<211> LENGTH: 39
<212> TYPE: DNA
<213> ORGANISM: Artificial Sequence
<220> FEATURE:
<223> OTHER INFORMATION: PCR-amplification of fragment of pBS1C

<400> SEQUENCE: 14
aggccggtct ccctagtaag gagtgtcaag aatgtttgc 39

<210> SEQ ID NO 15
<211> LENGTH: 33
<212> TYPE: DNA
<213> ORGANISM: Artificial Sequence
<220> FEATURE:
<223> OTHER INFORMATION: PCR-amplification of fragment of pBS1C

<400> SEQUENCE: 15
aggccgtctc gtcgaccgtc tagccttgcc ctc 33

<210> SEQ ID NO 16
<211> LENGTH: 32
<212> TYPE: DNA
<213> ORGANISM: Artificial Sequence
<220> FEATURE:
<223> OTHER INFORMATION: PCR-amplification of fragment of pMDS003

<400> SEQUENCE: 16
aagggatccc tcgagaattg tttggaaatg ac 32

<210> SEQ ID NO 17
<211> LENGTH: 29
<212> TYPE: DNA
<213> ORGANISM: Artificial Sequence
<220> FEATURE:
<223> OTHER INFORMATION: PCR-amplification of fragment of pMDS003

<400> SEQUENCE: 17
tcctctagag ccaacctagc ttggattct 29

<210> SEQ ID NO 18
<211> LENGTH: 1053
<212> TYPE: DNA
<213> ORGANISM: Fusobacterium nucleatum 4HI

<400> SEQUENCE: 18
atgtataaag tagcaagtct ttttgcaggt gtaggtggta tagatttggg ttttgaacaa 60
acaggtcatt ttaaaacagt atgggcaaat gaatatgatg ataaagctag ggaaacattt 120
agatgtaatt tttctaataa attaaatgaa aatgatataa gagaagtaga tgtacaagaa 180
attcctgata tagacatatt gttatcagga tttccttgta cttcatttag tgtagcaggt 240
tatagaaaag gctttgaaga tgaaaataca ggagatttat tttttgaaac tttaagaatt 300
atagttgcaa aacaacctaa agtaattttt ttagaaaatg ttaaaaattt acttggtcat 360
gataagggaa agacttttaa gataataaaa gaagctttag aaaaaaataa ttataaaata 420
aagtatcaag tattaaatgc aaaagactat ggaaatatac cacaaaatag ggaaagaatc 480
tatattgttg gttttaagaa tgaagaacat tttaaaaatt ttgaatttcc tttcccatta 540
gaattaacta gaaatattga agatatgctt gaaaaaaata atatagatga aaaatattat 600
tattcaaaag aaaaaaataa attttatgat accttagaaa aagaaataac taatgaaaac 660
acaatatatc agtggcgaag aagatatgta agagaaaata aaagtaatgt gtgtccaaca 720
ttaactgcaa atatgggaac aggagggcat aatgtccctt taataagagt taaagaaaga 780
ataagaaaac taacaccaag agaatgtttt aattttcaag gatatcccaa ggattttaag 840
ctcccagatt tagctccttc tcacttatat aaacaagcag gaaattcagt tgtagtgcca 900
gttataaaaa gaattgcaga gaatattttc aaagcattgg aagaatttaa tgtaagtttt 960
gaaataaaag taataaatta tttaaaaagt aaaaatatta atacatatga tgaattttta 1020
aattttattg aagaaaagca aatgaagttg ttt 1053

<210> SEQ ID NO 19
<211> LENGTH: 1053
<212> TYPE: DNA
<213> ORGANISM: Artificial Sequence
<220> FEATURE:
<223> OTHER INFORMATION: Codon-variant of MTase gene of Fusobacterium nucleatum 4HI

<400> SEQUENCE: 19
atgtataaag tggcatctct gtttgccggt gtaggcggta ttgaccttgg ttttgaacag 60
acaggtcatt ttaaaactgt ctgggcgaat gagtacgatg acaaagcccg cgaaactttt 120
agatgcaact tcagtaacaa actgaatgaa aacgatattc gtgaagtgga tgtccaagaa 180
attccggaca ttgatatctt gctatccggg ttcccgtgta ccagcttttc tgtcgcaggc 240
taccgcaagg gctttgaaga tgaaaacacg ggagatctgt tttcgaaac cttacggatc 300 attgttgcga aacagccaaa agttatattc cttgaaaacg tgaagaacct gttaggtcat 360
gataaaggga aaccttcaa gattatcaag gaagccttgg agaaaaataa ctataagata 420
aaataccaag tgctgaacgc gaaagactac ggcaatatcc ctcaaaatcg tgagcgcatc 480
tatatcgtgg gtttcaagaa tgaagagcac ttcaaaaatt ttgagttccc tttcccgctg 540
gagctgaccc ggaacattga agatatgctc gaaaagaaca atattgacga aaaatattac 600
tatagcaaag aaaaaaacaa attttatgat acgcttgaaa aagagattac caacgaaaac 660
acgatctacc agtggcgtcg ccgttatgta cgtgaaaaca aaagtaacgt gtgtcccaca 720
ctgactgcca acatgggcac cggcggacat aatgtgccgc tgatccgtgt taaagagcga 780
attcgcaaac tgacgccacg cgaatgcttt aattttcagg ggtatccgaa agattttaaa 840
ctccccgact tagcaccgtc gcacttatat aaacaggcgg gcaacagcgt agtcgtgccg 900

```
gttatcaaac gtattgctga gaatatcttt aaagcgctcg aagagttcaa tgtttccttt     960

gagattaaag tgatcaatta cttgaagtcg aaaaacatca atacctatga tgaattcctg    1020

aacttcattg aagagaaaca gatgaagctg ttc                                 1053


<210> SEQ ID NO 20
<211> LENGTH: 1053
<212> TYPE: DNA
<213> ORGANISM: Artificial Sequence
<220> FEATURE:
<223> OTHER INFORMATION: Codon-variant of MTase gene of Fusobacterium
      nucleatum 4HI

<400> SEQUENCE: 20

atgtataaag tcgcgagtct gttcgcggga gtcggcggaa ttgatcttgg ttttgagcag      60

accggccatt tcaaaactgt atgggcgaat gaatatgatg acaaagcccg cgagacgttc     120

cgttgtaatt tcagcaacaa gctgaacgaa aacgatattc gtgaagttga cgtccaggaa     180

atcccggaca ttgatatatt gctttcgggt ttcccatgca catctttcag cgttgcaggt     240

taccgcaaag ggttcgaaga tgagaacaca ggggacttat ttttcgagac tctgcgtatt     300

atcgttgcca agcagcccaa agtgatcttt ctggagaatg tgaaaaacct gttaggccac     360

gataaaggga aaacttttaa aattatcaaa gaagctctgg aaaaaaacaa ttataaaatc     420

aagtaccaag ttctgaacgc gaaagactac ggtaacatcc cgcagaatcg tgaacgaatt     480

tatatcgtag gctttaaaaa tgaagagcac tttaaaaact ttgagtttcc ttttcctttg     540

gagttaaccc ggaacataga ggacatgctc gaaaaaaata acattgatga aaaatactat     600

tactccaaag aaaaaaacaa attttatgac actctggaga aagaaattac caatgaaaat     660

acgatttatc agtggcgccg gcgctatgtg cgcgaaaaca agtctaatgt atgcccaacc     720

ctgacggcca acatgggcac gggtggccat aacgtgcccc tcatccgtgt gaaagaaaga     780

atccgcaaac tgaccccgcg cgaatgtttt aacttccaag gctatccgaa ggattttaaa     840

ttaccggatc ttgccccgag tcatctctac aaacaagcag gcaattccgt ggtcgtgccg     900

gtgattaagc gtattgcgga aaatatcttt aaggcactgg aggaattcaa cgtgtcgttt     960

gagatcaaag ttatcaatta cctaaagagc aagaacatta atacctacga tgaatttttg    1020

aacttcatcg aggaaaaaca gatgaaactg ttc                                 1053


<210> SEQ ID NO 21
<211> LENGTH: 1053
<212> TYPE: DNA
<213> ORGANISM: Artificial Sequence
<220> FEATURE:
<223> OTHER INFORMATION: Codon-variant of MTase gene of Fusobacterium
      nucleatum 4HI

<400> SEQUENCE: 21

atgtataaag tggcgagctt gtttgcgggt gtgggtggta ttgatttagg ttttgaacag      60

accggtcatt ttaaaaccgt gtgggcgaac gaatatgatg ataaagcccg tgaaaccttt     120

cgctgcaact ttagtaacaa actgaacgaa aacgatattc gcgaagtgga tgtgcaggaa     180

atcccagata ttgacatttt actgtcgggc tttccatgca cgtcgtttag cgtggcgggt     240

tatcgcaaag ggtttgaaga tgaaaacacc ggcgatctgt tttttgaaac gctgcgcatc     300

attgttgcga aacagccaaa agtgatcttt ctggaaaacg ttaaaaacct gttgggtcat     360

gataagggca agacgtttaa gattattaaa gaagccctgg aaaaaaacaa ctataaaatt     420

aagtatcagg tgctgaacgc gaaagactat ggcaacattc cgcagaaccg tgaacgcata     480
```

```
tatatcgttg gttttaagaa cgaagaacat tttaaaaact ttgaatttcc attcccgctg    540

gaactgacgc gcaacatcga agatatgttg gaaaaaaaca acattgatga aaaatattat    600

tattcgaaag aaaaaaacaa attttatgat actctggaaa aagaaattac gaacgaaaat    660

accatttatc aatggcggcg ccgctatgtg cgcgaaaaca aaagcaacgt ctgcccgacc    720

ctgacggcga acatgggcac cggcggacat aacgtaccac tgattcgcgt taaagaacgc    780

attcgcaaac ttaccccgcg cgaatgcttt aactttcagg gctatcctaa ggattttaag    840

ctcccggatc tggccccaag tcacctgtat aaacaggcgg gcaactcggt tgtggtcccg    900

gttattaaac gcatcgcgga gaacatcttc aaagcgttag aagaatttaa cgtgagcttt    960

gaaattaaag tgattaacta tctgaaaagc aaaaacatca acacctatga tgaatttctg   1020

aactttatcg aagaaaagca gatgaagtta ttt                                1053
```

<210> SEQ ID NO 22
<211> LENGTH: 1011
<212> TYPE: DNA
<213> ORGANISM: Bacillus licheniformis

<400> SEQUENCE: 22

```
atgacttatc gagtaggtag tatgtttgct gggataggtg gaacttgttt agggtttatc     60

caagctggcg ctaggattgt ctgggcaaat gaaatagaca aaaatgcttg tattacttat    120

agaaattatt ttggggatgc ttacttacaa gagggtgaca ttaacctaat agataaaaac    180

tccatacctg aactggacat tttgattgga ggttttcctt gccaagcctt ctctatagct    240

ggctatcgta aagggtttga agatgaaagg ggaaacgtgt tctttcaaat attagaggta    300

ttggaagcac aaagaaatgt ttatggacac ttaccccaag caataatgct tgagaatgta    360

aagaacttat ttacacatga tagaggtaat acgtacagag taataaaaga ggctttggaa    420

gcctttggtt ataccgtaaa agctgaggtt cttaattcaa tggaatacgg taacgtgcca    480

caaaacagag agcggattta tattgtaggt tttcaagatg agagccaagc tgaaaggttt    540

agctttccag acccaattcc tttaacaaat caacttaatg atgtaattga ccgaactcgg    600

agagttgata aaagatatta ttatgatgaa acctctcaat attatgatat gttgcgagaa    660

gccatggaca gtacagatac aacttatcaa ataagacgta tatatgttcg agaaaataga    720

agcaatgttt gtcctacact gacagcgaat atgggaactg gagggcataa tgttcctatt    780

gtattagact ttgaaaataa tataagaaaa ctaacaccag aagaatgctt actattgcaa    840

ggtttcccag ctgactatca ttttccagaa ggcatggcaa acactcacaa atataaacaa    900

gctggtaact ctgttacggt gccagttata agaagaattg ccactaatat tattagcgta    960

ttgaacattg gaatgaatat aaatcaagaa catgaatatg caatagctga a           1011
```

<210> SEQ ID NO 23
<211> LENGTH: 1011
<212> TYPE: DNA
<213> ORGANISM: Artificial Sequence
<220> FEATURE:
<223> OTHER INFORMATION: Codon-variant of MTase gene of Bacillus licheniformis

<400> SEQUENCE: 23

```
atgacttatc gagtaggtag tatgtttgcc ggtattggtg gcacctgtct gggttttatt     60

caggcaggcg cacgtattgt ttgggccaat gaaattgata aaaatgcctg cattacctat    120

cgcaattatt ttggtgatgc ctatctgcaa gaaggtgata ttaatctgat tgataagaat    180
```

```
agcattccgg aactggatat tctgattggt ggttttccgt gtcaggcatt tagcattgcc    240

ggttatcgta aaggctttga agatgaacgt ggcaatgtgt tttttcagat tctggaagtg    300

ctggaagcac agcgtaatgt ttatggtcat ctgccgcagg caattatgct ggaaaatgtg    360

aaaaacctgt ttacccatga tcgtggtaat acctatcgcg tgattaaaga agcactggaa    420

gcctttggtt ataccgttaa agccgaagtt ctgaatagca tggaatatgg taatgttccg    480

cagaatcgcg aacgtattta tattgtgggc tttcaggatg aaagccaggc agaacgtttt    540

agctttccag atccgattcc gctgaccaat cagctgaatg atgtgattga tcgtacccgt    600

cgtgtggata aacgctatta ttatgatgaa accagccagt attatgatat gctgcgtgaa    660

gcaatggata gcaccgatac cacctatcag attcgtcgta tttatgtgcg tgaaaatcgt    720

agcaatgttt gtccgaccct gaccgcaaat atgggcaccg gtggtcataa tgttccgatt    780

gtgctggatt ttgaaaataa tattcgcaaa ctgacaccgg aagaatgtct gctgctgcaa    840

ggttttccgg cagattatca ttttccggaa ggtatggcca atacccataa atacaaacag    900

gcaggcaata gcgttaccgt tccggttatt cgtcgcattg ccaccaatat tatttccgtg    960

ctgaatattg gcatgaatat taatcaggaa catgaatacg ccatcgccga a            1011
```

<210> SEQ ID NO 24
<211> LENGTH: 993
<212> TYPE: DNA
<213> ORGANISM: Artificial Sequence
<220> FEATURE:
<223> OTHER INFORMATION: Truncated variant of Bacillus licheniformis Mtase with deletion of 6 amino acids

<400> SEQUENCE: 24

```
atgacttatc gagtaggtag tatgtttgct gggataggtg gaacttgttt agggtttatc     60

caagctggcg ctaggattgt ctgggcaaat gaaatagaca aaaatgcttg tattacttat    120

agaaattatt ttggggatgc ttacttacaa gagggtgaca ttaacctaat agataaaaac    180

tccatacctg aactggacat tttgattgga ggttttcctt gccaagcctt ctctatagct    240

ggctatcgta aagggtttga agatgaaagg ggaaacgtgt tctttcaaat attagaggta    300

ttggaaggac acttacccca agcaataatg cttgagaatg taaagaactt atttacacat    360

gatagaggta atacgtacag agtaataaaa gaggctttgg aagcctttgg ttataccgta    420

aaagctgagg ttcttaattc aatggaatac ggtaacgtgc cacaaaacag agagcggatt    480

tatattgtag gttttcaaga tgagagccaa gctgaaaggt ttagctttcc agacccaatt    540

cctttaacaa atcaacttaa tgatgtaatt gaccgaactc ggagagttga taaaagatat    600

tattatgatg aaacctctca atattatgat atgttgcgag aagccatgga cagtacagat    660

acaacttatc aaataagacg tatatatgtt cgagaaaata gaagcaatgt ttgtcctaca    720

ctgacagcga atatgggaac tggagggcat aatgttccta ttgtattaga ctttgaaaat    780

aatataagaa aactaacacc agaagaatgc ttactattgc aaggtttccc agctgactat    840

cattttccag aaggcatggc aaacactcac aaatataaac aagctggtaa ctctgttacg    900

gtgccagtta taagaagaat tgccactaat attattagcg tattgaacat tggaatgaat    960

ataaatcaag aacatgaata tgcaatagct gaa                                 993
```

<210> SEQ ID NO 25
<211> LENGTH: 945
<212> TYPE: DNA
<213> ORGANISM: Bacillus sp. RFL6

<400> SEQUENCE: 25

```
atgttacaaa tagcaagttt attcgcaggt gtaggtggaa ttgatttagg atttgaacaa      60
actggatatt ttgaaacggt ttgggcaaat gaatatgata aaaatgcagc tattacctat     120
caatcaaatt ttaaaaacaa attaattata gatgatattc gaaatatcaa agtagaagat     180
gttcctgatt ttgatgtttt attatcagga tttccttgta cttcttttag cgtggctgga     240
tatagaaaag gctttgaaga tgaaaaaagc ggagatttat tttttgaaac tttacgcttg     300
attgtagcta aaaaaccaca agttatattt ttagaaaatg ttaaaaatct tgtgggtcat     360
gacaacggaa atacctttaa agtcatttat gaagcgttag aaagcaacgg atatcatata     420
aaataccaag ttctaaacgc aaaagatttt gggaatatac ctcaaaatag agagcgtatc     480
tatattgtag gttttaggaa tattgaacac tataaaaatt ttaattttcc gatgccacaa     540
ccacttacat taacaataaa agatatgata aatctttcag ataaactaga tgatagattt     600
tattatacag aggataaatg ttctttttat tcacctttac aagaacaaat gacttcagat     660
gaaacaatat atcaatggcg tagaaaatat gtgagagaaa acaaaagtaa tgtatgccct     720
acgttaactg cgaacatggg aactggagga cataatgttc cattagttaa aacaaaacat     780
ggaattagaa agttgactcc tagagagtgt ttcaattttc aaggttatcc tgaagatttc     840
attttacccg aattggctcc tacgcatctt tataagcaag ctggaaattc tgttgttgtt     900
cctgtcataa gacgcatagc agaaaatatt tataaatcta tgttg                    945
```

<210> SEQ ID NO 26
<211> LENGTH: 1224
<212> TYPE: DNA
<213> ORGANISM: Flavobacterium sp. 4H

<400> SEQUENCE: 26

```
atgagtttaa aacagacaat aagtattaat gaatttgacg gcaaaagcta tcaaattaga      60
cttgttgaag gtattgaaga caaagccgtt ttaacacatt atcttcataa ctatagaaat     120
ggtgtaaaaa agcattacga aaaagatgct atttcaactc taaaaaattt cgtagaatat     180
aaacaagagg aaactgaatt acctattgtt gcagaagatg ctttgcaaca acttttattt     240
gaagttgaaa acgtaccttt tccaactcca gaaaattata gctttaaatt cattgattta     300
tttgcaggaa ttggaggatt tagattagcg ttacaaaatg ttggcggaaa gtgtgttttt     360
acaagcgaat ggaataatga agctcaaaaa acttatcgag aaaattttgg agaagttccg     420
tttggcgaca taacaaaaga gcgaaataaa aattatattc ctgaaaaatt tgacatttta     480
tgtgcaggtt ttccttgcca agcattttca attgctggtt atcagaaagg ttttgctgac     540
acaagaggaa ctttattttt tgacattgag caaattgtag aaaaacataa acccaaggtt     600
gtatttttag aaaatgtaaa aaaccttgtt tctcacgaca atggaaatac atttaaaaca     660
attattgaaa cacttgaact aaaattgggt tataaaacat ttgcaaaagt tttaaattca     720
gcaactcacg caaatgttcc gcaaaatcgt gagcgaattt ttattgttgc atttgaccca     780
aaacaagtga aaaattattc aaaattcgag tttcctaaac caatcaaatt aacaaaaaca     840
attcacgact ttttggataa agaaaaagcaa gatgatattt tttattacaa aaaagaccat     900
caatattatc ctgaacttgt aaaaaacaatg atttcaaaag atacggttta tcaatggaga     960
agagtttatg caagagaaaa caaaagtaac ctttgcccta ctctaacggc aaatatgggt    1020
tctggcggac ataatgtacc attgattata gacgattttg gaattagaaa actaactcca    1080
aaagaatgtt ttgcgttcca aggttatcca atcgaaaaat atattattcc aaaacttgca    1140
```

aatagtaaac tttatatgca agctggaaat tctgtaacga caaatttaat tgaaagaatt 1200
gcaaatcaaa taattgaagt ttta 1224

<210> SEQ ID NO 27
<211> LENGTH: 951
<212> TYPE: DNA
<213> ORGANISM: Lactococcus lactis W39

<400> SEQUENCE: 27
atgttgaaaa ttgcttcttt tttcgccgga gttggcggaa ttgatttagg ttttgaaaat 60
gcaggtttca aaacaatata tgctaatgaa tttgataatt atgctgctga tacttttgaa 120
atgaactttg acgttaaggt agaccgacgt gatataaatg atgtacaagc tgatgaaata 180
ccagattttg atattatgtt agcaggtttt ccttgccaag ccttttctat tgctggttat 240
cgtcaaggct ttaacgatga acaaggtcga ggtaatcttt tttttgaact tgttcgtatt 300
ttagaaacaa aaaaacctcg tgttgcattc tttgaaaatg ttaaaaatct tgtttctcac 360
gatagcggga acacatttag agttatttgt tctgagttag aaagactagg gtacaagtat 420
ctttttcaag tgtttaatgc ttctgaatat ggaaatatac ctcaaaatag agaacgtatc 480
tatattgttg ctttcaaaaa taaaaaagat tatgcaaatt ttgaactacc aaaatctata 540
cctttaaaaa caacgattca cgatgttatt gatttttcta aaaaacaaga cgataagttc 600
tactatacct ctgaaaagaa taaatttttt gatgagttaa aagaaaatat gactaatcac 660
gacactacat atcagtggcg tagagtttat gtaagagaaa acaaaagtaa tttagtacca 720
acactaacgg ctaatatggg aacaggtggg cataatgtgc ctataatcct tacatatagc 780
ggagatattc gtaaattaac accaagagaa tgctttaacg ttcaaggttt cccaaaagaa 840
tataaacttc caaaccaaag taatgggaga ttatataaac aagcaggaaa cagtgttgta 900
gtaccagtta tagaaagaat tgcaaaaaat cttgcagata ctatagtcga a 951

<210> SEQ ID NO 28
<211> LENGTH: 1623
<212> TYPE: DNA
<213> ORGANISM: Clostridium difficile

<400> SEQUENCE: 28
atgtataatg ttatagatct ttttgcaggt gcaggtggtt tgagcttagg atttgaaatg 60
actaaaaaat ttaatatggt ggcttttgta gaaaaaaatg ataacgcagc aaaaacatac 120
cttgaaaatc atccgagtgt taagcgttat tgtgatatta aaagattaga ttttcaagat 180
atattaaaca gtgtcgataa gatagatgtt gttataggag gaccgccatg tcaaggtttt 240
tctaatgcta atagacaaaa aagaaaaatt ataaatggaa ataatgaatt agttaagcta 300
tatgttgatg ctattgataa attaaagcca aatgtatttg taatggaaaa tgtcaaaact 360
atatcttcaa ataagcattc attttatttg actaaaaaag ataaaaatca tataataaat 420
aatttaaaat taaatattta taataaagat agtgttttat atgatagaac tgagtatata 480
aatgaattat ttaatattat tagtatagaa gatattgaat catatattat atcaaatata 540
gacttaaaaa atttgaaaat aattattaag aaaaaaaagg atatatgtga ttatttaaat 600
aaaatatcta attataagaa agtaaaatct accatagaaa aattggaaac aaggggaaaa 660
atgccaaaat ggtatttaga attaataaat aaagtaaaaa atatattaga aaatatgtta 720
tataatagaa atttatcaga tgaacaaata ttttatttga acttattctt ggatattcaa 780
aatttatttt taggaatata tgagttaaaa tctgaatctg taattttcga aaatacactt 840

```
gatgataata aaattatagc taaaatggat acttacatta taatagatta tataaatgca    900

tcctttgagt atctaggata tgtattaaat ggaagtgcac taaattcaat tgattatgga    960

gtacctcaaa atagagaaag atttgtattg ataggagcaa aaaaagactt cttaaaaaat   1020

aaaaagatag aaactcctaa gcctatagtt ggagaaaatt atgttacagt aagagatgca   1080

ataggcgatt tagctgaata tgaggcttct aaaggtagta tggattattg ttttgaaaaa   1140

aatagtaata atattgaaaa agatttttat agaaagataa tattggatag caataaaata   1200

tacaatcatg tatgtacaga tacaagaaat atcgcactaa aaagatttga atatataaat   1260

caaggaaata attttcattc tttgccagat gagttaaaag gaacttatgc tgatccagaa   1320

agaactcaaa atactattta taaaagacta gtatatgata agccatcaga tactgttgta   1380

aatgtaagaa aatctatgtg gatacatcct attaaaaaca gagctgttag cgcaagagag   1440

gcggctagat tgcagtcatt ccctgatagt tataagtttt taggtacaaa agattctgta   1500

tatcaacaga taggaaatgc agtaccacct ttattaggtc gagtagtagc agaaaagata   1560

ttaaatttat ttaatgatga accaaatgag tatcttagag atgtgtttga agcactagat   1620

gga                                                                 1623
```

```
<210> SEQ ID NO 29
<211> LENGTH: 1623
<212> TYPE: DNA
<213> ORGANISM: Clostridium difficile 630

<400> SEQUENCE: 29

atgtataatg ttatagatct ttttgcaggt gcaggtggtt tgagcttagg atttgaaatg     60

actaaaaaat ttaatatggt ggcttttgta gaaaaaaatg ataacgcagc aaaaacatac    120

cttgaaaatc atccgagtgt taagcgttat tgtgatatta aaagattaga ttttcaagat    180

atattaaaca gtgtcgataa gatagatgtt gttataggag gaccgccatg tcaaggtttt    240

tctaatgcta atagacaaaa aagaaaaatt ataaatggaa ataatgaatt agttaagcta    300

tatgttgatg ctattgataa attaaagcca aatgtatttg taatggaaaa tgtcaaaact    360

atatcttcaa ataagcattc attttatttg actaaaaaag ataaaaatca tataataaat    420

aatttaaaat taaatattta taataaagat agtgttttat atgatagaac tgagtatata    480

aatgaattat ttaatattat tagtatagaa gatattgaat catatattat atcaaatata    540

gacttaaaaa atttgaaaat aattattaag aaaaaaaagg atatatgtga ttatttaaat    600

aaaatatcta attataagaa agtaaaatct accatagaaa aattggaaac aaggggaaaa    660

atgccaaaat ggtatttaga attaataaat aaagtaaaaa atatattaga aaatatgtta    720

tataatagaa atttatcaga tgaacaaata ttttatttga acttattctt ggatattcaa    780

aatttatttt taggaatata tgagttaaaa tctgaatctg taattttcga aaatacactt    840

gatgataata aaattatagc taaaatggat acttacatta taatagatta tataaatgca    900

tcctttgagt atctaggata tgtattaaat ggaagtgcac taaattcaat tgattatgga    960

gtacctcaaa atagagaaag atttgtattg ataggagcaa aaaaagactt cttaaaaaat   1020

aaaaagatag aaactcctaa gcctatagtt ggagaaaatt atgttacagt aagagatgca   1080

ataggcgatt tagctgaata tgaggcttct aaaggtagta tggattattg ttttgaaaaa   1140

aatagtaata atattgaaaa agatttttat agaaagataa tattggatag caataaaata   1200

tacaatcatg tatgtacaga tacaagaaat atcgcactaa aaagatttga atatataaat   1260

caaggaaata attttcattc tttgccagat gagttaaaag gaacttatgc tgatccagaa   1320
```

```
agaactcaaa atactattta taaaagacta gtatatgata agccatcaga tactgttgta   1380

aatgtaagaa aatctatgtg gatacatcct attaaaaaca gagctgttag cgcaagagag   1440

gcggctagat tgcagtcatt ccctgatagt tataagtttt taggtacaaa agattctgta   1500

tatcaacaga taggaaatgc agtaccacct ttattaggtc gagtagtagc agaaaagata   1560

ttaaatttat ttaatgatga accaaatgag tatcttagag atgtgtttga agcactagat   1620

gga                                                                 1623
```

```
<210> SEQ ID NO 30
<211> LENGTH: 957
<212> TYPE: DNA
<213> ORGANISM: Caldicellulosiruptor kristjanssonii 177R1B

<400> SEQUENCE: 30

gtgattaaaa taagagtagt aagtttgttt tctggagttg gtggtatttg cttagctttc     60

aaacaagcag gatttgatgt gatttgggca aatgatattg ataagtatgc ttgtataaca    120

tatagatcta atttcccaac agtagagctt gttgaaggtg atatacaaag tattgattcc    180

aataatatac ctgaatgtga tatcattaca gcaggatttc cttgccaacc tttttctatt    240

gcaggttatc agagaggtct caatgaccct cgtggaagac tattttatga aattgttcgt    300

atcgttcatg ataaaaagcc aaaaattatt tttctcgaaa atgtaaaaaa tcttgtttca    360

cataacaacg ggattacctt taaaaatatt ttaaatgctc tggaaaatga gggatactat    420

ttaaagtatg ctgtgcttaa ttctttagaa tacggtaatg tacctcaaaa tagggaaagg    480

gtttatatag taggtttttt agataaatca atgtatgaag catttaagtt tccagaacca    540

gtatcactaa cagttactat tcacgatatt attaagccat gggagaaaaa agacgaaaag    600

tattactaca gagaagggaa gtattatgaa cttctcaaac aaaatgtaga tgaccctaat    660

acagtttatc agataaggcg tatatatgtc agaaaaaata agaagggtgt atgtcctact    720

ttaactgcaa acatgggtga aggtggtcat aatgttccta tcgtaatgga taactatgga    780

tttagaaaat tgaccccacg agaatgtttc atactacaag gcttcccaga agattttgta    840

ctaccttcag gtttagcaga ttctaagttg tataaacaag caggtaatgc cgttactgta    900

acagttgtaa agcgtattgc agataaaata ttggaaactt gtcttgtaaa atcaata       957
```

```
<210> SEQ ID NO 31
<211> LENGTH: 1218
<212> TYPE: DNA
<213> ORGANISM: Clostridium mangenotii LM2

<400> SEQUENCE: 31

atgactaaaa acaatgatgc tgtaagtacc aaaaactata ctgtagcaag ttttttcggt     60

ggagttggcg gtattgactt aggatttgaa caagctaaga agttcagtac ggtttacatt    120

aatgaattcg ataaaaatgc acaggagaca atatctataa atttccctag ggttagtcta    180

gatagacgag atatacatga agtaagggta gatgaagtgc caagtactga tatagttgcc    240

gggggatttc catgtcaagc tttctcgata gcagggtata gaaaaggatt tgaagatgaa    300

agaggagacc tgtttttga acttttaagg attataaaac atcataagcc aaaagttata    360

ttcatagaga atgtaaaaaa tatggttaca catgatcatg gaaatacatt taaggtaata    420

agagaagctt taactttaaa tggatactat ataaaatgga aagtcataaa tggaaaagat    480

tatggtgata ttcctcaaaa tagagaacgt atatatataa ctggattttt agataaaaat    540

gcttttgatg aatttgaatt tccgaataaa atagaactga ctaatggatt agatacagta    600
```

atagatttta aagctaaggt agaggataag tactactata gacaaggtat ccaaccattt 660
tatgataagc tagaagaaac tataacatct caaaattcag tttatcaatg gagaaggcaa 720
tatgttagag agaacaaaag tggagtagta ccaactctaa ctgctaacat gggaactgga 780
gggcataatg taccccttat tctatcatac tatggaataa gaaaattgac tccaagggaa 840
acttttaata ttcaaggatt tccaacggat tttaaattac ctgaaatttc aaatgctcag 900
ttatataaac aagcagggaa tagtgttgta gtaccagtta ttaaacgtat agcagaaaat 960
atagctaatg cattagaaga agcagagaat aagaatgaaa tatataatac tgtagaagaa 1020
aataataaaa atatacttat atatgtagat atgaaaagca ggtttgaagg agagagcttt 1080
gtgcaagcct actttgatga agtttgtgaa gctaacgact ttgcaattat aacagaaatt 1140
ccaattttat cagatgaaga atatctaaag cttgtaaaaa gaaatgtatc aaagcgtttt 1200
tattcattac aaactaag 1218

<210> SEQ ID NO 32
<211> LENGTH: 954
<212> TYPE: DNA
<213> ORGANISM: Capnocytophaga ochracea DSM 7271

<400> SEQUENCE: 32
atgggaaaaa gcgttaaatt catagattta tttgcagggg tagggggctt ccgctatgct 60
ttgcagaata taggggctga atgtgtcttt tcgtcagaat gggacaagtt cgctcagcaa 120
acctataagc taaactatgg agaagttcct tttggcgata ttactttaca agaaacgaaa 180
gataatattc ctaatgaatt tgatatactt tgcgcaggat ttccttgtca agcattttct 240
atagctggat atcaaaaagg ttttgaagat attaggggaa cacttttttt tgagatagaa 300
gaaatagtaa ggaagcatcg tcctaaggtt atttttttag aaaatgtaaa gaacttagtg 360
agtcacgata agggtaaaac atttaaggta ataacgaata tcttagaaga gaaattaggt 420
tacaagatat tttataaagt cctcaataca atggaatatg ctaatattcc acaaaataga 480
gagcgtattt ttatagtagc ttttgatcct aaacaagttc ctaattataa agagttccaa 540
tttcctgaaa aaattaaact tactaaaacg attcatagct tttagagaa aggaaaacag 600 aatgattatt tttattatca gctatctcac aaatacagtc cagaacttat taaaatagta 660
acacgtaaag atactattta tcaatggagg cgtgtgtatg ttcgagaaaa taagaacaat 720
gtttgtccta ctttaacagc taatatgggt acagggggac ataatgtacc gattattaaa 780
gataattttg gtattaggaa gttaacccca cgagaatgtt ttaattttca aggttatcca 840
aaaggcttta tactttctaa agaaatagct atatcaaaat tatatatgca ggcagggaac 900
tctgtgacaa tgcctttaat tcaaagagta agtgaacaaa ttttgaaagt gtta 954

<210> SEQ ID NO 33
<211> LENGTH: 351
<212> TYPE: PRT
<213> ORGANISM: Fusobacterium nucleatum 4HI

<400> SEQUENCE: 33

```
Met Tyr Lys Val Ala Ser Leu Phe Ala Gly Val Gly Gly Ile Asp Leu
1               5                   10                  15

Gly Phe Glu Gln Thr Gly His Phe Lys Thr Val Trp Ala Asn Glu Tyr
            20                  25                  30

Asp Asp Lys Ala Arg Glu Thr Phe Arg Cys Asn Phe Ser Asn Lys Leu
        35                  40                  45
```

```
Asn Glu Asn Asp Ile Arg Glu Val Asp Val Gln Glu Ile Pro Asp Ile
    50                  55                  60

Asp Ile Leu Leu Ser Gly Phe Pro Cys Thr Ser Phe Ser Val Ala Gly
65                  70                  75                  80

Tyr Arg Lys Gly Phe Glu Asp Glu Asn Thr Gly Asp Leu Phe Phe Glu
                85                  90                  95

Thr Leu Arg Ile Ile Val Ala Lys Gln Pro Lys Val Ile Phe Leu Glu
            100                 105                 110

Asn Val Lys Asn Leu Leu Gly His Asp Lys Gly Lys Thr Phe Lys Ile
        115                 120                 125

Ile Lys Glu Ala Leu Glu Lys Asn Asn Tyr Lys Ile Lys Tyr Gln Val
    130                 135                 140

Leu Asn Ala Lys Asp Tyr Gly Asn Ile Pro Gln Asn Arg Glu Arg Ile
145                 150                 155                 160

Tyr Ile Val Gly Phe Lys Asn Glu Glu His Phe Lys Asn Phe Glu Phe
                165                 170                 175

Pro Phe Pro Leu Glu Leu Thr Arg Asn Ile Glu Asp Met Leu Glu Lys
            180                 185                 190

Asn Asn Ile Asp Glu Lys Tyr Tyr Tyr Ser Lys Glu Lys Asn Lys Phe
        195                 200                 205

Tyr Asp Thr Leu Glu Lys Glu Ile Thr Asn Glu Asn Thr Ile Tyr Gln
    210                 215                 220

Trp Arg Arg Arg Tyr Val Arg Glu Asn Lys Ser Asn Val Cys Pro Thr
225                 230                 235                 240

Leu Thr Ala Asn Met Gly Thr Gly Gly His Asn Val Pro Leu Ile Arg
                245                 250                 255

Val Lys Glu Arg Ile Arg Lys Leu Thr Pro Arg Glu Cys Phe Asn Phe
            260                 265                 270

Gln Gly Tyr Pro Lys Asp Phe Lys Leu Pro Asp Leu Ala Pro Ser His
        275                 280                 285

Leu Tyr Lys Gln Ala Gly Asn Ser Val Val Val Pro Val Ile Lys Arg
    290                 295                 300

Ile Ala Glu Asn Ile Phe Lys Ala Leu Glu Glu Phe Asn Val Ser Phe
305                 310                 315                 320

Glu Ile Lys Val Ile Asn Tyr Leu Lys Ser Lys Asn Ile Asn Thr Tyr
                325                 330                 335

Asp Glu Phe Leu Asn Phe Ile Glu Glu Lys Gln Met Lys Leu Phe
            340                 345                 350


<210> SEQ ID NO 34
<211> LENGTH: 337
<212> TYPE: PRT
<213> ORGANISM: Bacillus licheniformis

<400> SEQUENCE: 34

Met Thr Tyr Arg Val Gly Ser Met Phe Ala Gly Ile Gly Gly Thr Cys
1               5                   10                  15

Leu Gly Phe Ile Gln Ala Gly Ala Arg Ile Val Trp Ala Asn Glu Ile
            20                  25                  30

Asp Lys Asn Ala Cys Ile Thr Tyr Arg Asn Tyr Phe Gly Asp Ala Tyr
        35                  40                  45

Leu Gln Glu Gly Asp Ile Asn Leu Ile Asp Lys Asn Ser Ile Pro Glu
    50                  55                  60

Leu Asp Ile Leu Ile Gly Gly Phe Pro Cys Gln Ala Phe Ser Ile Ala
65                  70                  75                  80
```

```
Gly Tyr Arg Lys Gly Phe Glu Asp Glu Arg Gly Asn Val Phe Phe Gln
                85                  90                  95

Ile Leu Glu Val Leu Glu Ala Gln Arg Asn Val Tyr Gly His Leu Pro
            100                 105                 110

Gln Ala Ile Met Leu Glu Asn Val Lys Asn Leu Phe Thr His Asp Arg
        115                 120                 125

Gly Asn Thr Tyr Arg Val Ile Lys Glu Ala Leu Glu Ala Phe Gly Tyr
    130                 135                 140

Thr Val Lys Ala Glu Val Leu Asn Ser Met Glu Tyr Gly Asn Val Pro
145                 150                 155                 160

Gln Asn Arg Glu Arg Ile Tyr Ile Val Gly Phe Gln Asp Glu Ser Gln
                165                 170                 175

Ala Glu Arg Phe Ser Phe Pro Asp Pro Ile Pro Leu Thr Asn Gln Leu
            180                 185                 190

Asn Asp Val Ile Asp Arg Thr Arg Arg Val Asp Lys Arg Tyr Tyr Tyr
        195                 200                 205

Asp Glu Thr Ser Gln Tyr Tyr Asp Met Leu Arg Glu Ala Met Asp Ser
    210                 215                 220

Thr Asp Thr Thr Tyr Gln Ile Arg Arg Ile Tyr Val Arg Glu Asn Arg
225                 230                 235                 240

Ser Asn Val Cys Pro Thr Leu Thr Ala Asn Met Gly Thr Gly Gly His
                245                 250                 255

Asn Val Pro Ile Val Leu Asp Phe Glu Asn Asn Ile Arg Lys Leu Thr
            260                 265                 270

Pro Glu Glu Cys Leu Leu Leu Gln Gly Phe Pro Ala Asp Tyr His Phe
        275                 280                 285

Pro Glu Gly Met Ala Asn Thr His Lys Tyr Lys Gln Ala Gly Asn Ser
    290                 295                 300

Val Thr Val Pro Val Ile Arg Arg Ile Ala Thr Asn Ile Ile Ser Val
305                 310                 315                 320

Leu Asn Ile Gly Met Asn Ile Asn Gln Glu His Glu Tyr Ala Ile Ala
                325                 330                 335

Glu


<210> SEQ ID NO 35
<211> LENGTH: 331
<212> TYPE: PRT
<213> ORGANISM: Artificial Sequence
<220> FEATURE:
<223> OTHER INFORMATION: Truncated variant of Bacillus licheniformis
      Mtase with deletion of 6 amino acids

<400> SEQUENCE: 35

Met Thr Tyr Arg Val Gly Ser Met Phe Ala Gly Ile Gly Gly Thr Cys
1               5                   10                  15

Leu Gly Phe Ile Gln Ala Gly Ala Arg Ile Val Trp Ala Asn Glu Ile
            20                  25                  30

Asp Lys Asn Ala Cys Ile Thr Tyr Arg Asn Tyr Phe Gly Asp Ala Tyr
        35                  40                  45

Leu Gln Glu Gly Asp Ile Asn Leu Ile Asp Lys Asn Ser Ile Pro Glu
    50                  55                  60

Leu Asp Ile Leu Ile Gly Gly Phe Pro Cys Gln Ala Phe Ser Ile Ala
65                  70                  75                  80

Gly Tyr Arg Lys Gly Phe Glu Asp Glu Arg Gly Asn Val Phe Phe Gln
                85                  90                  95
```

```
Ile Leu Glu Val Leu Glu Ala Gln Arg Pro Gln Ala Ile Met Leu Glu
            100                 105                 110

Asn Val Lys Asn Leu Phe Thr His Asp Arg Gly Asn Thr Tyr Arg Val
        115                 120                 125

Ile Lys Glu Ala Leu Glu Ala Phe Gly Tyr Thr Val Lys Ala Glu Val
    130                 135                 140

Leu Asn Ser Met Glu Tyr Gly Asn Val Pro Gln Asn Arg Glu Arg Ile
145                 150                 155                 160

Tyr Ile Val Gly Phe Gln Asp Glu Ser Gln Ala Glu Arg Phe Ser Phe
                165                 170                 175

Pro Asp Pro Ile Pro Leu Thr Asn Gln Leu Asn Asp Val Ile Asp Arg
            180                 185                 190

Thr Arg Arg Val Asp Lys Arg Tyr Tyr Tyr Asp Glu Thr Ser Gln Tyr
        195                 200                 205

Tyr Asp Met Leu Arg Glu Ala Met Asp Ser Thr Asp Thr Thr Tyr Gln
    210                 215                 220

Ile Arg Arg Ile Tyr Val Arg Glu Asn Arg Ser Asn Val Cys Pro Thr
225                 230                 235                 240

Leu Thr Ala Asn Met Gly Thr Gly Gly His Asn Val Pro Ile Val Leu
                245                 250                 255

Asp Phe Glu Asn Asn Ile Arg Lys Leu Thr Pro Glu Glu Cys Leu Leu
            260                 265                 270

Leu Gln Gly Phe Pro Ala Asp Tyr His Phe Pro Glu Gly Met Ala Asn
        275                 280                 285

Thr His Lys Tyr Lys Gln Ala Gly Asn Ser Val Thr Val Pro Val Ile
    290                 295                 300

Arg Arg Ile Ala Thr Asn Ile Ile Ser Val Leu Asn Ile Gly Met Asn
305                 310                 315                 320

Ile Asn Gln Glu His Glu Tyr Ala Ile Ala Glu
                325                 330


<210> SEQ ID NO 36
<211> LENGTH: 315
<212> TYPE: PRT
<213> ORGANISM: Bacillus sp. RFL6

<400> SEQUENCE: 36

Met Leu Gln Ile Ala Ser Leu Phe Ala Gly Val Gly Gly Ile Asp Leu
1               5                   10                  15

Gly Phe Glu Gln Thr Gly Tyr Phe Glu Thr Val Trp Ala Asn Glu Tyr
            20                  25                  30

Asp Lys Asn Ala Ala Ile Thr Tyr Gln Ser Asn Phe Lys Asn Lys Leu
        35                  40                  45

Ile Ile Asp Asp Ile Arg Asn Ile Lys Val Glu Asp Val Pro Asp Phe
    50                  55                  60

Asp Val Leu Leu Ser Gly Phe Pro Cys Thr Ser Phe Ser Val Ala Gly
65                  70                  75                  80

Tyr Arg Lys Gly Phe Glu Asp Glu Lys Ser Gly Asp Leu Phe Phe Glu
                85                  90                  95

Thr Leu Arg Leu Ile Val Ala Lys Lys Pro Gln Val Ile Phe Leu Glu
            100                 105                 110

Asn Val Lys Asn Leu Val Gly His Asp Asn Gly Asn Thr Phe Lys Val
        115                 120                 125

Ile Tyr Glu Ala Leu Glu Ser Asn Gly Tyr His Ile Lys Tyr Gln Val
    130                 135                 140
```

```
Leu Asn Ala Lys Asp Phe Gly Asn Ile Pro Gln Asn Arg Glu Arg Ile
145                 150                 155                 160

Tyr Ile Val Gly Phe Arg Asn Ile Glu His Tyr Lys Asn Phe Asn Phe
                165                 170                 175

Pro Met Pro Gln Pro Leu Thr Leu Thr Ile Lys Asp Met Ile Asn Leu
            180                 185                 190

Ser Asp Lys Leu Asp Asp Arg Phe Tyr Tyr Thr Glu Asp Lys Cys Ser
        195                 200                 205

Phe Tyr Ser Pro Leu Gln Glu Gln Met Thr Ser Asp Glu Thr Ile Tyr
    210                 215                 220

Gln Trp Arg Arg Lys Tyr Val Arg Glu Asn Lys Ser Asn Val Cys Pro
225                 230                 235                 240

Thr Leu Thr Ala Asn Met Gly Thr Gly Gly His Asn Val Pro Leu Val
                245                 250                 255

Lys Thr Lys His Gly Ile Arg Lys Leu Thr Pro Arg Glu Cys Phe Asn
            260                 265                 270

Phe Gln Gly Tyr Pro Glu Asp Phe Ile Leu Pro Glu Leu Ala Pro Thr
        275                 280                 285

His Leu Tyr Lys Gln Ala Gly Asn Ser Val Val Val Pro Val Ile Arg
    290                 295                 300

Arg Ile Ala Glu Asn Ile Tyr Lys Ser Met Leu
305                 310                 315


<210> SEQ ID NO 37
<211> LENGTH: 541
<212> TYPE: PRT
<213> ORGANISM: Clostridium difficile

<400> SEQUENCE: 37

Met Tyr Asn Val Ile Asp Leu Phe Ala Gly Ala Gly Gly Leu Ser Leu
1               5                   10                  15

Gly Phe Glu Met Thr Lys Lys Phe Asn Met Val Ala Phe Val Glu Lys
            20                  25                  30

Asn Asp Asn Ala Ala Lys Thr Tyr Leu Glu Asn His Pro Ser Val Lys
        35                  40                  45

Arg Tyr Cys Asp Ile Lys Arg Leu Asp Phe Gln Asp Ile Leu Asn Ser
    50                  55                  60

Val Asp Lys Ile Asp Val Val Ile Gly Gly Pro Pro Cys Gln Gly Phe
65                  70                  75                  80

Ser Asn Ala Asn Arg Gln Lys Arg Lys Ile Ile Asn Gly Asn Asn Glu
                85                  90                  95

Leu Val Lys Leu Tyr Val Asp Ala Ile Asp Lys Leu Lys Pro Asn Val
            100                 105                 110

Phe Val Met Glu Asn Val Lys Thr Ile Ser Ser Asn Lys His Ser Phe
        115                 120                 125

Tyr Leu Thr Lys Lys Asp Lys Asn His Ile Ile Asn Asn Leu Lys Leu
    130                 135                 140

Asn Ile Tyr Asn Lys Asp Ser Val Leu Tyr Asp Arg Thr Glu Tyr Ile
145                 150                 155                 160

Asn Glu Leu Phe Asn Ile Ile Ser Ile Glu Asp Ile Glu Ser Tyr Ile
                165                 170                 175

Ile Ser Asn Ile Asp Leu Lys Asn Leu Lys Ile Ile Ile Lys Lys Lys
            180                 185                 190

Lys Asp Ile Cys Asp Tyr Leu Asn Lys Ile Ser Asn Tyr Lys Lys Val
        195                 200                 205
```

```
Lys Ser Thr Ile Glu Lys Leu Glu Thr Arg Gly Lys Met Pro Lys Trp
    210                 215                 220

Tyr Leu Glu Leu Ile Asn Lys Val Lys Asn Ile Leu Glu Asn Met Leu
225                 230                 235                 240

Tyr Asn Arg Asn Leu Ser Asp Glu Gln Ile Phe Tyr Leu Asn Leu Phe
                245                 250                 255

Leu Asp Ile Gln Asn Leu Phe Leu Gly Ile Tyr Glu Leu Lys Ser Glu
            260                 265                 270

Ser Val Ile Phe Glu Asn Thr Leu Asp Asp Asn Lys Ile Ile Ala Lys
        275                 280                 285

Met Asp Thr Tyr Ile Ile Ile Asp Tyr Ile Asn Ala Ser Phe Glu Tyr
    290                 295                 300

Leu Gly Tyr Val Leu Asn Gly Ser Ala Leu Asn Ser Ile Asp Tyr Gly
305                 310                 315                 320

Val Pro Gln Asn Arg Glu Arg Phe Val Leu Ile Gly Ala Lys Lys Asp
                325                 330                 335

Phe Leu Lys Asn Lys Lys Ile Glu Thr Pro Lys Pro Ile Val Gly Glu
            340                 345                 350

Asn Tyr Val Thr Val Arg Asp Ala Ile Gly Asp Leu Ala Glu Tyr Glu
        355                 360                 365

Ala Ser Lys Gly Ser Met Asp Tyr Cys Phe Glu Lys Asn Ser Asn Asn
    370                 375                 380

Ile Glu Lys Asp Phe Tyr Arg Lys Ile Ile Leu Asp Ser Asn Lys Ile
385                 390                 395                 400

Tyr Asn His Val Cys Thr Asp Thr Arg Asn Ile Ala Leu Lys Arg Phe
                405                 410                 415

Glu Tyr Ile Asn Gln Gly Asn Asn Phe His Ser Leu Pro Asp Glu Leu
            420                 425                 430

Lys Gly Thr Tyr Ala Asp Pro Glu Arg Thr Gln Asn Thr Ile Tyr Lys
        435                 440                 445

Arg Leu Val Tyr Asp Lys Pro Ser Asp Thr Val Val Asn Val Arg Lys
    450                 455                 460

Ser Met Trp Ile His Pro Ile Lys Asn Arg Ala Val Ser Ala Arg Glu
465                 470                 475                 480

Ala Ala Arg Leu Gln Ser Phe Pro Asp Ser Tyr Lys Phe Leu Gly Thr
                485                 490                 495

Lys Asp Ser Val Tyr Gln Gln Ile Gly Asn Ala Val Pro Pro Leu Leu
            500                 505                 510

Gly Arg Val Val Ala Glu Lys Ile Leu Asn Leu Phe Asn Asp Glu Pro
        515                 520                 525

Asn Glu Tyr Leu Arg Asp Val Phe Glu Ala Leu Asp Gly
    530                 535                 540
```

<210> SEQ ID NO 38
<211> LENGTH: 541
<212> TYPE: PRT
<213> ORGANISM: Clostridium difficile 630

<400> SEQUENCE: 38

```
Met Tyr Asn Val Ile Asp Leu Phe Ala Gly Ala Gly Gly Leu Ser Leu
1               5                   10                  15

Gly Phe Glu Met Thr Lys Lys Phe Asn Met Val Ala Phe Val Glu Lys
            20                  25                  30

Asn Asp Asn Ala Ala Lys Thr Tyr Leu Glu Asn His Pro Ser Val Lys
        35                  40                  45
```

-continued

```
Arg Tyr Cys Asp Ile Lys Arg Leu Asp Phe Gln Asp Ile Leu Asn Ser
    50                  55                  60

Val Asp Lys Ile Asp Val Val Ile Gly Gly Pro Pro Cys Gln Gly Phe
65                  70                  75                  80

Ser Asn Ala Asn Arg Gln Lys Arg Lys Ile Ile Asn Gly Asn Asn Glu
                85                  90                  95

Leu Val Lys Leu Tyr Val Asp Ala Ile Asp Lys Leu Lys Pro Asn Val
            100                 105                 110

Phe Val Met Glu Asn Val Lys Thr Ile Ser Ser Asn Lys His Ser Phe
        115                 120                 125

Tyr Leu Thr Lys Lys Asp Lys Asn His Ile Ile Asn Asn Leu Lys Leu
    130                 135                 140

Asn Ile Tyr Asn Lys Asp Ser Val Leu Tyr Asp Arg Thr Glu Tyr Ile
145                 150                 155                 160

Asn Glu Leu Phe Asn Ile Ile Ser Ile Glu Asp Ile Glu Ser Tyr Ile
                165                 170                 175

Ile Ser Asn Ile Asp Leu Lys Asn Leu Lys Ile Ile Ile Lys Lys Lys
            180                 185                 190

Lys Asp Ile Cys Asp Tyr Leu Asn Lys Ile Ser Asn Tyr Lys Lys Val
        195                 200                 205

Lys Ser Thr Ile Glu Lys Leu Glu Thr Arg Gly Lys Met Pro Lys Trp
    210                 215                 220

Tyr Leu Glu Leu Ile Asn Lys Val Lys Asn Ile Leu Glu Asn Met Leu
225                 230                 235                 240

Tyr Asn Arg Asn Leu Ser Asp Glu Gln Ile Phe Tyr Leu Asn Leu Phe
                245                 250                 255

Leu Asp Ile Gln Asn Leu Phe Leu Gly Ile Tyr Glu Leu Lys Ser Glu
            260                 265                 270

Ser Val Ile Phe Glu Asn Thr Leu Asp Asp Asn Lys Ile Ile Ala Lys
        275                 280                 285

Met Asp Thr Tyr Ile Ile Ile Asp Tyr Ile Asn Ala Ser Phe Glu Tyr
    290                 295                 300

Leu Gly Tyr Val Leu Asn Gly Ser Ala Leu Asn Ser Ile Asp Tyr Gly
305                 310                 315                 320

Val Pro Gln Asn Arg Glu Arg Phe Val Leu Ile Gly Ala Lys Lys Asp
                325                 330                 335

Phe Leu Lys Asn Lys Lys Ile Glu Thr Pro Lys Pro Ile Val Gly Glu
            340                 345                 350

Asn Tyr Val Thr Val Arg Asp Ala Ile Gly Asp Leu Ala Glu Tyr Glu
        355                 360                 365

Ala Ser Lys Gly Ser Met Asp Tyr Cys Phe Glu Lys Asn Ser Asn Asn
    370                 375                 380

Ile Glu Lys Asp Phe Tyr Arg Lys Ile Ile Leu Asp Ser Asn Lys Ile
385                 390                 395                 400

Tyr Asn His Val Cys Thr Asp Thr Arg Asn Ile Ala Leu Lys Arg Phe
                405                 410                 415

Glu Tyr Ile Asn Gln Gly Asn Asn Phe His Ser Leu Pro Asp Glu Leu
            420                 425                 430

Lys Gly Thr Tyr Ala Asp Pro Glu Arg Thr Gln Asn Thr Ile Tyr Lys
        435                 440                 445

Arg Leu Val Tyr Asp Lys Pro Ser Asp Thr Val Val Asn Val Arg Lys
    450                 455                 460
```

```
Ser Met Trp Ile His Pro Ile Lys Asn Arg Ala Val Ser Ala Arg Glu
465                 470                 475                 480

Ala Ala Arg Leu Gln Ser Phe Pro Asp Ser Tyr Lys Phe Leu Gly Thr
                485                 490                 495

Lys Asp Ser Val Tyr Gln Gln Ile Gly Asn Ala Val Pro Pro Leu Leu
            500                 505                 510

Gly Arg Val Val Ala Glu Lys Ile Leu Asn Leu Phe Asn Asp Glu Pro
        515                 520                 525

Asn Glu Tyr Leu Arg Asp Val Phe Glu Ala Leu Asp Gly
    530                 535                 540


<210> SEQ ID NO 39
<211> LENGTH: 319
<212> TYPE: PRT
<213> ORGANISM: Caldicellulosiruptor kristjanssonii 177R1B

<400> SEQUENCE: 39

Met Ile Lys Ile Arg Val Val Ser Leu Phe Ser Gly Val Gly Gly Ile
1               5                   10                  15

Cys Leu Ala Phe Lys Gln Ala Gly Phe Asp Val Ile Trp Ala Asn Asp
            20                  25                  30

Ile Asp Lys Tyr Ala Cys Ile Thr Tyr Arg Ser Asn Phe Pro Thr Val
        35                  40                  45

Glu Leu Val Glu Gly Asp Ile Gln Ser Ile Asp Ser Asn Asn Ile Pro
    50                  55                  60

Glu Cys Asp Ile Ile Thr Ala Gly Phe Pro Cys Gln Pro Phe Ser Ile
65                  70                  75                  80

Ala Gly Tyr Gln Arg Gly Leu Asn Asp Pro Arg Gly Arg Leu Phe Tyr
                85                  90                  95

Glu Ile Val Arg Ile Val His Asp Lys Lys Pro Lys Ile Ile Phe Leu
            100                 105                 110

Glu Asn Val Lys Asn Leu Val Ser His Asn Asn Gly Ile Thr Phe Lys
        115                 120                 125

Asn Ile Leu Asn Ala Leu Glu Asn Glu Gly Tyr Tyr Leu Lys Tyr Ala
    130                 135                 140

Val Leu Asn Ser Leu Glu Tyr Gly Asn Val Pro Gln Asn Arg Glu Arg
145                 150                 155                 160

Val Tyr Ile Val Gly Phe Leu Asp Lys Ser Met Tyr Glu Ala Phe Lys
                165                 170                 175

Phe Pro Glu Pro Val Ser Leu Thr Val Thr Ile His Asp Ile Ile Lys
            180                 185                 190

Pro Trp Glu Lys Lys Asp Glu Lys Tyr Tyr Tyr Arg Glu Gly Lys Tyr
        195                 200                 205

Tyr Glu Leu Leu Lys Gln Asn Val Asp Asp Pro Asn Thr Val Tyr Gln
    210                 215                 220

Ile Arg Arg Ile Tyr Val Arg Lys Asn Lys Lys Gly Val Cys Pro Thr
225                 230                 235                 240

Leu Thr Ala Asn Met Gly Glu Gly Gly His Asn Val Pro Ile Val Met
                245                 250                 255

Asp Asn Tyr Gly Phe Arg Lys Leu Thr Pro Arg Glu Cys Phe Ile Leu
            260                 265                 270

Gln Gly Phe Pro Glu Asp Phe Val Leu Pro Ser Gly Leu Ala Asp Ser
        275                 280                 285
```

```
Lys Leu Tyr Lys Gln Ala Gly Asn Ala Val Thr Val Thr Val Val Lys
    290                 295                 300

Arg Ile Ala Asp Lys Ile Leu Glu Thr Cys Leu Val Lys Ser Ile
305                 310                 315


<210> SEQ ID NO 40
<211> LENGTH: 406
<212> TYPE: PRT
<213> ORGANISM: Clostridium mangenotii LM2

<400> SEQUENCE: 40

Met Thr Lys Asn Asn Asp Ala Val Ser Thr Lys Asn Tyr Thr Val Ala
1               5                   10                  15

Ser Phe Phe Gly Gly Val Gly Gly Ile Asp Leu Gly Phe Glu Gln Ala
            20                  25                  30

Lys Lys Phe Ser Thr Val Tyr Ile Asn Glu Phe Asp Lys Asn Ala Gln
        35                  40                  45

Glu Thr Ile Ser Ile Asn Phe Pro Arg Val Ser Leu Asp Arg Arg Asp
    50                  55                  60

Ile His Glu Val Arg Val Asp Glu Val Pro Ser Thr Asp Ile Val Ala
65                  70                  75                  80

Gly Gly Phe Pro Cys Gln Ala Phe Ser Ile Ala Gly Tyr Arg Lys Gly
                85                  90                  95

Phe Glu Asp Glu Arg Gly Asp Leu Phe Phe Glu Leu Leu Arg Ile Ile
            100                 105                 110

Lys His His Lys Pro Lys Val Ile Phe Ile Glu Asn Val Lys Asn Met
        115                 120                 125

Val Thr His Asp His Gly Asn Thr Phe Lys Val Ile Arg Glu Ala Leu
    130                 135                 140

Thr Leu Asn Gly Tyr Tyr Ile Lys Trp Lys Val Ile Asn Gly Lys Asp
145                 150                 155                 160

Tyr Gly Asp Ile Pro Gln Asn Arg Glu Arg Ile Tyr Ile Thr Gly Phe
                165                 170                 175

Leu Asp Lys Asn Ala Phe Asp Glu Phe Glu Phe Pro Asn Lys Ile Glu
            180                 185                 190

Leu Thr Asn Gly Leu Asp Thr Val Ile Asp Phe Lys Ala Lys Val Glu
        195                 200                 205

Asp Lys Tyr Tyr Tyr Arg Gln Gly Ile Gln Pro Phe Tyr Asp Lys Leu
    210                 215                 220

Glu Glu Thr Ile Thr Ser Gln Asn Ser Val Tyr Gln Trp Arg Arg Gln
225                 230                 235                 240

Tyr Val Arg Glu Asn Lys Ser Gly Val Val Pro Thr Leu Thr Ala Asn
                245                 250                 255

Met Gly Thr Gly Gly His Asn Val Pro Leu Ile Leu Ser Tyr Tyr Gly
            260                 265                 270

Ile Arg Lys Leu Thr Pro Arg Glu Thr Phe Asn Ile Gln Gly Phe Pro
        275                 280                 285

Thr Asp Phe Lys Leu Pro Glu Ile Ser Asn Ala Gln Leu Tyr Lys Gln
    290                 295                 300

Ala Gly Asn Ser Val Val Val Pro Val Ile Lys Arg Ile Ala Glu Asn
305                 310                 315                 320

Ile Ala Asn Ala Leu Glu Glu Ala Glu Asn Lys Asn Glu Ile Tyr Asn
                325                 330                 335

Thr Val Glu Glu Asn Asn Lys Asn Ile Leu Ile Tyr Val Asp Met Lys
            340                 345                 350
```

Ser Arg Phe Glu Gly Glu Ser Phe Val Gln Ala Tyr Phe Asp Glu Val
        355                 360                 365

Cys Glu Ala Asn Asp Phe Ala Ile Ile Thr Glu Ile Pro Ile Leu Ser
    370                 375                 380

Asp Glu Glu Tyr Leu Lys Leu Val Lys Arg Asn Val Ser Lys Arg Phe
385                 390                 395                 400

Tyr Ser Leu Gln Thr Lys
                405

<210> SEQ ID NO 41
<211> LENGTH: 318
<212> TYPE: PRT
<213> ORGANISM: Capnocytophaga ochracea DSM 7271

<400> SEQUENCE: 41

Met Gly Lys Ser Val Lys Phe Ile Asp Leu Phe Ala Gly Val Gly Gly
1               5                   10                  15

Phe Arg Tyr Ala Leu Gln Asn Ile Gly Ala Glu Cys Val Phe Ser Ser
            20                  25                  30

Glu Trp Asp Lys Phe Ala Gln Gln Thr Tyr Lys Leu Asn Tyr Gly Glu
        35                  40                  45

Val Pro Phe Gly Asp Ile Thr Leu Gln Glu Thr Lys Asp Asn Ile Pro
    50                  55                  60

Asn Glu Phe Asp Ile Leu Cys Ala Gly Phe Pro Cys Gln Ala Phe Ser
65                  70                  75                  80

Ile Ala Gly Tyr Gln Lys Gly Phe Glu Asp Ile Arg Gly Thr Leu Phe
                85                  90                  95

Phe Glu Ile Glu Glu Ile Val Arg Lys His Arg Pro Lys Val Ile Phe
            100                 105                 110

Leu Glu Asn Val Lys Asn Leu Val Ser His Asp Lys Gly Lys Thr Phe
        115                 120                 125

Lys Val Ile Thr Asn Ile Leu Glu Glu Lys Leu Gly Tyr Lys Ile Phe
    130                 135                 140

Tyr Lys Val Leu Asn Thr Met Glu Tyr Ala Asn Ile Pro Gln Asn Arg
145                 150                 155                 160

Glu Arg Ile Phe Ile Val Ala Phe Asp Pro Lys Gln Val Pro Asn Tyr
                165                 170                 175

Lys Glu Phe Gln Phe Pro Glu Lys Ile Lys Leu Thr Lys Thr Ile His
            180                 185                 190

Ser Phe Leu Glu Lys Gly Lys Gln Asn Asp Tyr Phe Tyr Tyr Gln Leu
        195                 200                 205

Ser His Lys Tyr Ser Pro Glu Leu Ile Lys Ile Val Thr Arg Lys Asp
    210                 215                 220

Thr Ile Tyr Gln Trp Arg Arg Val Tyr Val Arg Glu Asn Lys Asn Asn
225                 230                 235                 240

Val Cys Pro Thr Leu Thr Ala Asn Met Gly Thr Gly Gly His Asn Val
                245                 250                 255

Pro Ile Ile Lys Asp Asn Phe Gly Ile Arg Lys Leu Thr Pro Arg Glu
            260                 265                 270

Cys Phe Asn Phe Gln Gly Tyr Pro Lys Gly Phe Ile Leu Ser Lys Glu
        275                 280                 285

Ile Ala Ile Ser Lys Leu Tyr Met Gln Ala Gly Asn Ser Val Thr Met
    290                 295                 300

Pro Leu Ile Gln Arg Val Ser Glu Gln Ile Leu Lys Val Leu
305                 310                 315

```
<210> SEQ ID NO 42
<211> LENGTH: 408
<212> TYPE: PRT
<213> ORGANISM: Flavobacterium sp. 4H

<400> SEQUENCE: 42

Met Ser Leu Lys Gln Thr Ile Ser Ile Asn Glu Phe Asp Gly Lys Ser
1               5                   10                  15

Tyr Gln Ile Arg Leu Val Glu Gly Ile Glu Asp Lys Ala Val Leu Thr
            20                  25                  30

His Tyr Leu His Asn Tyr Arg Asn Gly Val Lys Lys His Tyr Glu Lys
        35                  40                  45

Asp Ala Ile Ser Thr Leu Lys Asn Phe Val Glu Tyr Lys Gln Glu Glu
    50                  55                  60

Thr Glu Leu Pro Ile Val Ala Glu Asp Ala Leu Gln Gln Leu Leu Phe
65                  70                  75                  80

Glu Val Glu Asn Val Pro Phe Pro Thr Pro Glu Asn Tyr Ser Phe Lys
                85                  90                  95

Phe Ile Asp Leu Phe Ala Gly Ile Gly Gly Phe Arg Leu Ala Leu Gln
            100                 105                 110

Asn Val Gly Gly Lys Cys Val Phe Thr Ser Glu Trp Asn Asn Glu Ala
        115                 120                 125

Gln Lys Thr Tyr Arg Glu Asn Phe Gly Glu Val Pro Phe Gly Asp Ile
    130                 135                 140

Thr Lys Glu Arg Asn Lys Asn Tyr Ile Pro Glu Lys Phe Asp Ile Leu
145                 150                 155                 160

Cys Ala Gly Phe Pro Cys Gln Ala Phe Ser Ile Ala Gly Tyr Gln Lys
                165                 170                 175

Gly Phe Ala Asp Thr Arg Gly Thr Leu Phe Phe Asp Ile Glu Gln Ile
            180                 185                 190

Val Glu Lys His Lys Pro Lys Val Val Phe Leu Glu Asn Val Lys Asn
        195                 200                 205

Leu Val Ser His Asp Asn Gly Asn Thr Phe Lys Thr Ile Ile Glu Thr
    210                 215                 220

Leu Glu Leu Lys Leu Gly Tyr Lys Thr Phe Ala Lys Val Leu Asn Ser
225                 230                 235                 240

Ala Thr His Ala Asn Val Pro Gln Asn Arg Glu Arg Ile Phe Ile Val
                245                 250                 255

Ala Phe Asp Pro Lys Gln Val Lys Asn Tyr Ser Lys Phe Glu Phe Pro
            260                 265                 270

Lys Pro Ile Lys Leu Thr Lys Thr Ile His Asp Phe Leu Asp Lys Glu
        275                 280                 285

Lys Gln Asp Asp Ile Phe Tyr Tyr Lys Lys Asp His Gln Tyr Tyr Pro
    290                 295                 300

Glu Leu Val Lys Thr Met Ile Ser Lys Asp Thr Val Tyr Gln Trp Arg
305                 310                 315                 320

Arg Val Tyr Ala Arg Glu Asn Lys Ser Asn Leu Cys Pro Thr Leu Thr
                325                 330                 335

Ala Asn Met Gly Ser Gly Gly His Asn Val Pro Leu Ile Ile Asp Asp
            340                 345                 350

Phe Gly Ile Arg Lys Leu Thr Pro Lys Glu Cys Phe Ala Phe Gln Gly
        355                 360                 365

Tyr Pro Ile Glu Lys Tyr Ile Ile Pro Lys Leu Ala Asn Ser Lys Leu
    370                 375                 380
```

```
Tyr Met Gln Ala Gly Asn Ser Val Thr Thr Asn Leu Ile Glu Arg Ile
385                 390                 395                 400

Ala Asn Gln Ile Ile Glu Val Leu
                405
```

<210> SEQ ID NO 43
<211> LENGTH: 317
<212> TYPE: PRT
<213> ORGANISM: Lactococcus lactis W39

<400> SEQUENCE: 43

```
Met Leu Lys Ile Ala Ser Phe Phe Ala Gly Val Gly Gly Ile Asp Leu
1               5                   10                  15

Gly Phe Glu Asn Ala Gly Phe Lys Thr Ile Tyr Ala Asn Glu Phe Asp
            20                  25                  30

Asn Tyr Ala Ala Asp Thr Phe Glu Met Asn Phe Asp Val Lys Val Asp
        35                  40                  45

Arg Arg Asp Ile Asn Asp Val Gln Ala Asp Glu Ile Pro Asp Phe Asp
    50                  55                  60

Ile Met Leu Ala Gly Phe Pro Cys Gln Ala Phe Ser Ile Ala Gly Tyr
65                  70                  75                  80

Arg Gln Gly Phe Asn Asp Glu Gln Gly Arg Gly Asn Leu Phe Phe Glu
                85                  90                  95

Leu Val Arg Ile Leu Glu Thr Lys Lys Pro Arg Val Ala Phe Phe Glu
            100                 105                 110

Asn Val Lys Asn Leu Val Ser His Asp Ser Gly Asn Thr Phe Arg Val
        115                 120                 125

Ile Cys Ser Glu Leu Glu Arg Leu Gly Tyr Lys Tyr Leu Phe Gln Val
    130                 135                 140

Phe Asn Ala Ser Glu Tyr Gly Asn Ile Pro Gln Asn Arg Glu Arg Ile
145                 150                 155                 160

Tyr Ile Val Ala Phe Lys Asn Lys Lys Asp Tyr Ala Asn Phe Glu Leu
                165                 170                 175

Pro Lys Ser Ile Pro Leu Lys Thr Thr Ile His Asp Val Ile Asp Phe
            180                 185                 190

Ser Lys Lys Gln Asp Asp Lys Phe Tyr Tyr Thr Ser Glu Lys Asn Lys
        195                 200                 205

Phe Phe Asp Glu Leu Lys Glu Asn Met Thr Asn His Asp Thr Thr Tyr
    210                 215                 220

Gln Trp Arg Arg Val Tyr Val Arg Glu Asn Lys Ser Asn Leu Val Pro
225                 230                 235                 240

Thr Leu Thr Ala Asn Met Gly Thr Gly Gly His Asn Val Pro Ile Ile
                245                 250                 255

Leu Thr Tyr Ser Gly Asp Ile Arg Lys Leu Thr Pro Arg Glu Cys Phe
            260                 265                 270

Asn Val Gln Gly Phe Pro Lys Glu Tyr Lys Leu Pro Asn Gln Ser Asn
        275                 280                 285

Gly Arg Leu Tyr Lys Gln Ala Gly Asn Ser Val Val Val Pro Val Ile
    290                 295                 300

Glu Arg Ile Ala Lys Asn Leu Ala Asp Thr Ile Val Glu
305                 310                 315
```

<210> SEQ ID NO 44
<211> LENGTH: 841
<212> TYPE: PRT
<213> ORGANISM: Bacillus licheniformis DSM 13

<400> SEQUENCE: 44

```
Met Leu Gly Ile Leu Asn Lys Val Phe Asp Pro Thr Lys Arg Thr Leu
1               5                   10                  15

Ser Arg Tyr Glu Lys Lys Ala Asn Glu Ile Asp Ala Leu Lys Ala Asp
            20                  25                  30

Ile Glu Lys Leu Ser Asp Glu Ala Leu Lys Gln Lys Thr Ile Glu Phe
        35                  40                  45

Lys Glu Arg Leu Glu Lys Gly Glu Thr Val Asp Asp Leu Leu Val Glu
    50                  55                  60

Ala Phe Ala Val Val Arg Glu Ala Ser Arg Arg Val Thr Gly Met Phe
65                  70                  75                  80

Pro Phe Lys Val Gln Leu Met Gly Gly Val Ala Leu His Glu Gly Asn
                85                  90                  95

Ile Ala Glu Met Lys Thr Gly Glu Gly Lys Thr Leu Thr Ser Thr Met
            100                 105                 110

Pro Val Tyr Leu Asn Ala Leu Ser Gly Lys Gly Val His Val Val Thr
        115                 120                 125

Val Asn Glu Tyr Leu Ala Ser Arg Asp Ala Glu Glu Met Gly Lys Ile
    130                 135                 140

Phe Glu Phe Leu Gly Leu Thr Val Gly Leu Asn Leu Asn Ser Leu Ser
145                 150                 155                 160

Lys Asp Glu Lys Arg Glu Ala Tyr Ala Ala Asp Ile Thr Tyr Ser Thr
                165                 170                 175

Asn Asn Glu Leu Gly Phe Asp Tyr Leu Arg Asp Asn Met Val Leu Tyr
            180                 185                 190

Lys Glu Gln Met Val Gln Arg Pro Leu His Phe Ala Val Ile Asp Glu
        195                 200                 205

Val Asp Ser Ile Leu Ile Asp Glu Ala Arg Thr Pro Leu Ile Ile Ser
    210                 215                 220

Gly Gln Ala Ala Lys Ser Thr Lys Leu Tyr Val Gln Ala Asn Ala Phe
225                 230                 235                 240

Val Arg Thr Leu Lys Ala Asp Gln Asp Tyr Thr Tyr Asp Val Lys Thr
                245                 250                 255

Lys Gly Val Gln Leu Thr Glu Glu Gly Met Thr Lys Ala Glu Lys Ala
            260                 265                 270

Phe Gly Ile Glu Asn Leu Phe Asp Val Arg His Val Ala Leu Asn His
        275                 280                 285

His Ile Ala Gln Ala Leu Lys Ala His Ala Ala Met His Lys Asp Val
    290                 295                 300

Asp Tyr Val Val Glu Asp Gly Gln Val Val Ile Val Asp Ser Phe Thr
305                 310                 315                 320

Gly Arg Leu Met Lys Gly Arg Arg Tyr Ser Asp Gly Leu His Gln Ala
                325                 330                 335

Ile Glu Ala Lys Glu Gly Leu Glu Ile Gln Asn Glu Ser Met Thr Leu
            340                 345                 350

Ala Thr Ile Thr Phe Gln Asn Tyr Phe Arg Met Tyr Glu Lys Leu Ala
        355                 360                 365

Gly Met Thr Gly Thr Ala Lys Thr Glu Glu Glu Glu Phe Arg Asn Ile
    370                 375                 380

Tyr Asn Met Gln Val Val Thr Ile Pro Thr Asn Lys Pro Ile Ala Arg
385                 390                 395                 400

Asp Asp Arg Pro Asp Leu Ile Tyr Arg Thr Met Glu Gly Lys Phe Lys
                405                 410                 415
```

```
Ala Val Ala Glu Asp Val Ala Gln Arg Tyr Met Val Gly Gln Pro Val
            420                 425                 430

Leu Val Gly Thr Val Ala Val Glu Thr Ser Glu Leu Ile Ser Arg Leu
        435                 440                 445

Leu Lys Asn Lys Gly Ile Pro His Gln Val Leu Asn Ala Lys Asn His
    450                 455                 460

Glu Arg Glu Ala Gln Ile Ile Glu Asp Ala Gly Gln Lys Gly Ala Val
465                 470                 475                 480

Thr Ile Ala Thr Asn Met Ala Gly Arg Gly Thr Asp Ile Lys Leu Gly
                485                 490                 495

Glu Gly Val Lys Glu Leu Gly Gly Leu Ala Val Ile Gly Thr Glu Arg
            500                 505                 510

His Glu Ser Arg Arg Ile Asp Asn Gln Leu Arg Gly Arg Ser Gly Arg
        515                 520                 525

Gln Gly Asp Pro Gly Ile Thr Gln Phe Tyr Leu Ser Met Glu Asp Glu
    530                 535                 540

Leu Met Lys Arg Phe Gly Ala Glu Arg Thr Met Ala Met Leu Asp Arg
545                 550                 555                 560

Phe Gly Met Asp Asp Ser Thr Pro Ile Gln Ser Lys Met Val Ser Arg
                565                 570                 575

Ala Val Glu Ser Ser Gln Lys Arg Val Glu Gly Asn Asn Phe Asp Ala
            580                 585                 590

Arg Lys Gln Leu Leu Gln Tyr Asp Asp Val Leu Arg Gln Gln Arg Glu
        595                 600                 605

Val Ile Tyr Lys Gln Arg Phe Glu Val Ile Asp Ser Asp Asn Leu Arg
    610                 615                 620

Ser Ile Val Glu Asn Met Ile Lys Ala Ser Leu Glu Arg Ala Val Ala
625                 630                 635                 640

Ser Tyr Thr Pro Lys Glu Asp Leu Pro Glu Glu Trp Asn Leu Asp Gly
                645                 650                 655

Leu Val Glu Leu Val Asn Ala Asn Phe Leu Asp Glu Gly Gly Val Glu
            660                 665                 670

Lys Ser Asp Ile Phe Gly Lys Glu Pro Glu Glu Ile Thr Glu Leu Ile
        675                 680                 685

Tyr Asp Arg Ile Lys Thr Lys Tyr Asp Glu Lys Glu Glu Arg Tyr Gly
    690                 695                 700

Ser Glu Gln Met Arg Glu Phe Glu Lys Val Ile Val Leu Arg Glu Val
705                 710                 715                 720

Asp Thr Lys Trp Met Asp His Ile Asp Ala Met Asp Gln Leu Arg Gln
                725                 730                 735

Gly Ile His Leu Arg Ala Tyr Ala Gln Thr Asn Pro Leu Arg Glu Tyr
            740                 745                 750

Gln Met Glu Gly Phe Ala Met Phe Glu Asn Met Ile Ala Ala Ile Glu
        755                 760                 765

Asp Asp Val Ala Lys Phe Val Met Lys Ala Glu Ile Glu Asn Asn Leu
    770                 775                 780

Glu Arg Glu Glu Val Ile Gln Gly Gln Thr Thr Ala His Gln Pro Lys
785                 790                 795                 800

Glu Gly Asp Glu Glu Lys Gln Ala Lys Lys Lys Pro Val Arg Lys Ala
                805                 810                 815
```

```
Val Asp Ile Gly Arg Asn Asp Pro Cys Tyr Cys Gly Ser Gly Lys Lys
            820                 825                 830

Tyr Lys Asn Cys Cys Gly Arg Thr Glu
        835                 840


<210> SEQ ID NO 45
<211> LENGTH: 901
<212> TYPE: PRT
<213> ORGANISM: Escherichia coli K12

<400> SEQUENCE: 45

Met Leu Ile Lys Leu Leu Thr Lys Val Phe Gly Ser Arg Asn Asp Arg
1               5                   10                  15

Thr Leu Arg Arg Met Arg Lys Val Val Asn Ile Ile Asn Ala Met Glu
            20                  25                  30

Pro Glu Met Glu Lys Leu Ser Asp Glu Glu Leu Lys Gly Lys Thr Ala
        35                  40                  45

Glu Phe Arg Ala Arg Leu Glu Lys Gly Glu Val Leu Glu Asn Leu Ile
    50                  55                  60

Pro Glu Ala Phe Ala Val Val Arg Glu Ala Ser Lys Arg Val Phe Gly
65                  70                  75                  80

Met Arg His Phe Asp Val Gln Leu Leu Gly Gly Met Val Leu Asn Glu
                85                  90                  95

Arg Cys Ile Ala Glu Met Arg Thr Gly Glu Gly Lys Thr Leu Thr Ala
            100                 105                 110

Thr Leu Pro Ala Tyr Leu Asn Ala Leu Thr Gly Lys Gly Val His Val
        115                 120                 125

Val Thr Val Asn Asp Tyr Leu Ala Gln Arg Asp Ala Glu Asn Asn Arg
    130                 135                 140

Pro Leu Phe Glu Phe Leu Gly Leu Thr Val Gly Ile Asn Leu Pro Gly
145                 150                 155                 160

Met Pro Ala Pro Ala Lys Arg Glu Ala Tyr Ala Ala Asp Ile Thr Tyr
                165                 170                 175

Gly Thr Asn Asn Glu Tyr Gly Phe Asp Tyr Leu Arg Asp Asn Met Ala
            180                 185                 190

Phe Ser Pro Glu Glu Arg Val Gln Arg Lys Leu His Tyr Ala Leu Val
        195                 200                 205

Asp Glu Val Asp Ser Ile Leu Ile Asp Glu Ala Arg Thr Pro Leu Ile
    210                 215                 220

Ile Ser Gly Pro Ala Glu Asp Ser Ser Glu Met Tyr Lys Arg Val Asn
225                 230                 235                 240

Lys Ile Ile Pro His Leu Ile Arg Gln Glu Lys Glu Asp Ser Glu Thr
                245                 250                 255

Phe Gln Gly Glu Gly His Phe Ser Val Asp Glu Lys Ser Arg Gln Val
            260                 265                 270

Asn Leu Thr Glu Arg Gly Leu Val Leu Ile Glu Glu Leu Leu Val Lys
        275                 280                 285

Glu Gly Ile Met Asp Glu Gly Glu Ser Leu Tyr Ser Pro Ala Asn Ile
    290                 295                 300

Met Leu Met His His Val Thr Ala Ala Leu Arg Ala His Ala Leu Phe
305                 310                 315                 320

Thr Arg Asp Val Asp Tyr Ile Val Lys Asp Gly Glu Val Ile Ile Val
                325                 330                 335

Asp Glu His Thr Gly Arg Thr Met Gln Gly Arg Arg Trp Ser Asp Gly
            340                 345                 350
```

```
Leu His Gln Ala Val Glu Ala Lys Glu Gly Val Gln Ile Gln Asn Glu
        355                 360                 365

Asn Gln Thr Leu Ala Ser Ile Thr Phe Gln Asn Tyr Phe Arg Leu Tyr
    370                 375                 380

Glu Lys Leu Ala Gly Met Thr Gly Thr Ala Asp Thr Glu Ala Phe Glu
385                 390                 395                 400

Phe Ser Ser Ile Tyr Lys Leu Asp Thr Val Val Val Pro Thr Asn Arg
                405                 410                 415

Pro Met Ile Arg Lys Asp Leu Pro Asp Leu Val Tyr Met Thr Glu Ala
            420                 425                 430

Glu Lys Ile Gln Ala Ile Ile Glu Asp Ile Lys Glu Arg Thr Ala Lys
        435                 440                 445

Gly Gln Pro Val Leu Val Gly Thr Ile Ser Ile Glu Lys Ser Glu Leu
    450                 455                 460

Val Ser Asn Glu Leu Thr Lys Ala Gly Ile Lys His Asn Val Leu Asn
465                 470                 475                 480

Ala Lys Phe His Ala Asn Glu Ala Ala Ile Val Ala Gln Ala Gly Tyr
                485                 490                 495

Pro Ala Ala Val Thr Ile Ala Thr Asn Met Ala Gly Arg Gly Thr Asp
            500                 505                 510

Ile Val Leu Gly Gly Ser Trp Gln Ala Glu Val Ala Ala Leu Glu Asn
        515                 520                 525

Pro Thr Ala Glu Gln Ile Glu Lys Ile Lys Ala Asp Trp Gln Val Arg
    530                 535                 540

His Asp Ala Val Leu Glu Ala Gly Gly Leu His Ile Ile Gly Thr Glu
545                 550                 555                 560

Arg His Glu Ser Arg Arg Ile Asp Asn Gln Leu Arg Gly Arg Ser Gly
                565                 570                 575

Arg Gln Gly Asp Ala Gly Ser Ser Arg Phe Tyr Leu Ser Met Glu Asp
            580                 585                 590

Ala Leu Met Arg Ile Phe Ala Ser Asp Arg Val Ser Gly Met Met Arg
        595                 600                 605

Lys Leu Gly Met Lys Pro Gly Glu Ala Ile Glu His Pro Trp Val Thr
    610                 615                 620

Lys Ala Ile Ala Asn Ala Gln Arg Lys Val Glu Ser Arg Asn Phe Asp
625                 630                 635                 640

Ile Arg Lys Gln Leu Leu Glu Tyr Asp Asp Val Ala Asn Asp Gln Arg
                645                 650                 655

Arg Ala Ile Tyr Ser Gln Arg Asn Glu Leu Leu Asp Val Ser Asp Val
            660                 665                 670

Ser Glu Thr Ile Asn Ser Ile Arg Glu Asp Val Phe Lys Ala Thr Ile
        675                 680                 685

Asp Ala Tyr Ile Pro Pro Gln Ser Leu Glu Glu Met Trp Asp Ile Pro
    690                 695                 700

Gly Leu Gln Glu Arg Leu Lys Asn Asp Phe Asp Leu Asp Leu Pro Ile
705                 710                 715                 720

Ala Glu Trp Leu Asp Lys Glu Pro Glu Leu His Glu Glu Thr Leu Arg
                725                 730                 735

Glu Arg Ile Leu Ala Gln Ser Ile Glu Val Tyr Gln Arg Lys Glu Glu
            740                 745                 750

Val Val Gly Ala Glu Met Met Arg His Phe Glu Lys Gly Val Met Leu
        755                 760                 765
```

```
Gln Thr Leu Asp Ser Leu Trp Lys Glu His Leu Ala Ala Met Asp Tyr
    770                 775                 780

Leu Arg Gln Gly Ile His Leu Arg Gly Tyr Ala Gln Lys Asp Pro Lys
785                 790                 795                 800

Gln Glu Tyr Lys Arg Glu Ser Phe Ser Met Phe Ala Ala Met Leu Glu
                805                 810                 815

Ser Leu Lys Tyr Glu Val Ile Ser Thr Leu Ser Lys Val Gln Val Arg
            820                 825                 830

Met Pro Glu Glu Val Glu Glu Leu Glu Gln Gln Arg Arg Met Glu Ala
        835                 840                 845

Glu Arg Leu Ala Gln Met Gln Gln Leu Ser His Gln Asp Asp Asp Ser
    850                 855                 860

Ala Ala Ala Ala Ala Leu Ala Ala Gln Thr Gly Glu Arg Lys Val Gly
865                 870                 875                 880

Arg Asn Asp Pro Cys Pro Cys Gly Ser Gly Lys Lys Tyr Lys Gln Cys
                885                 890                 895

His Gly Arg Leu Gln
            900


<210> SEQ ID NO 46
<211> LENGTH: 799
<212> TYPE: PRT
<213> ORGANISM: Lactobacillus acidophilus NCFM

<400> SEQUENCE: 46

Met Ala Asn Ile Leu Lys Lys Leu Tyr Asn Thr Asp Lys Arg Glu Leu
1               5                   10                  15

Lys Lys Phe Glu Lys Tyr Ala Thr Lys Val Glu Glu His Ala Asp Glu
            20                  25                  30

Met Ser Lys Leu Ser Asp Glu Gln Leu Gln Ala Lys Thr Pro Glu Phe
        35                  40                  45

Arg Glu Arg Ile Lys Asn Gly Glu Ser Leu Asp Asp Leu Leu Pro Glu
    50                  55                  60

Ala Phe Ala Val Ala Arg Glu Gly Ala Lys Arg Val Leu Gly Leu Tyr
65                  70                  75                  80

Pro Phe His Val Gln Ile Leu Gly Gly Ile Ala Leu His Phe Gly Asn
                85                  90                  95

Ile Ala Glu Met Met Thr Gly Glu Gly Lys Thr Leu Thr Ala Thr Met
            100                 105                 110

Pro Val Tyr Leu Asn Ala Leu Glu Gly Lys Gly Val His Val Val Thr
        115                 120                 125

Val Asn Glu Tyr Leu Ser Ser Arg Asp Glu Glu Glu Met Gly Gln Leu
    130                 135                 140

Tyr Arg Trp Leu Gly Leu Thr Val Gly Leu Asn Ile Asn Ser Met Ser
145                 150                 155                 160

Pro Asp Glu Lys Arg Glu Ala Tyr Asn Cys Asp Val Thr Tyr Ser Thr
                165                 170                 175

Asn Ser Glu Leu Gly Phe Asp Tyr Leu Arg Asp Asn Met Val Val Tyr
            180                 185                 190

Lys Glu Gln Met Val Gln Arg Pro Leu Asn Tyr Ala Ile Ile Asp Glu
        195                 200                 205

Val Asp Ser Ile Leu Ile Asp Glu Ala Arg Thr Pro Leu Ile Ile Ser
    210                 215                 220

Gly Glu Ala Glu Gln Ala Asn Ser Asp Tyr Ile Arg Ala Asp Arg Phe
225                 230                 235                 240
```

```
Val Lys Thr Leu Thr Glu Asp Lys Ser Asp Asp Asp Ala Asp Asp Asp
                245                 250                 255

Glu Asp His Gly Asp Tyr Lys Ile Asp Trp Pro Thr Lys Thr Ile Ser
            260                 265                 270

Leu Thr Arg Thr Gly Ile Glu Lys Ala Cys Glu His Phe Gly Leu Lys
        275                 280                 285

Asn Leu Tyr Asp Val Glu Asn Gln Lys Leu Val His His Ile Asp Gln
    290                 295                 300

Ala Leu Arg Ala Asn Tyr Ile Met Leu Lys Asp Ile Asp Tyr Val Val
305                 310                 315                 320

Gln Asp Gly Glu Val Leu Ile Val Asp Ser Phe Thr Gly Arg Val Met
                325                 330                 335

Glu Gly Arg Arg Tyr Ser Asp Gly Leu His Gln Ala Ile Glu Ala Lys
            340                 345                 350

Glu Gly Val Lys Ile Gln Glu Glu Ser Arg Thr Gln Ala Thr Ile Thr
        355                 360                 365

Tyr Gln Asn Phe Phe Arg Met Tyr Lys Lys Leu Ser Gly Met Thr Gly
    370                 375                 380

Thr Gly Lys Thr Glu Glu Glu Glu Phe Arg Glu Ile Tyr Asn Met Gln
385                 390                 395                 400

Val Ile Thr Ile Pro Thr Asn Arg Pro Ile Ala Arg Lys Asp Met Pro
                405                 410                 415

Asp Ile Leu Tyr Pro Thr Leu Asp Ser Lys Phe His Ala Val Ile Glu
            420                 425                 430

Glu Ile Lys Lys Arg His Ala Lys Gly Gln Pro Val Leu Val Gly Thr
        435                 440                 445

Val Ala Ile Glu Ser Ser Glu Arg Leu Ser His Leu Leu Asp Glu Ala
    450                 455                 460

Asn Ile Pro His Ala Val Leu Asn Ala Lys Asn His Ala Lys Glu Ala
465                 470                 475                 480

Gln Ile Ile Met Asn Ala Gly Gln Arg Gly Ala Val Thr Ile Ala Thr
                485                 490                 495

Asn Met Ala Gly Arg Gly Thr Asp Ile Lys Leu Gly Pro Gly Val Lys
            500                 505                 510

Glu Leu Gly Gly Leu Ala Val Ile Gly Thr Glu Arg His Glu Ser Arg
        515                 520                 525

Arg Ile Asp Asn Gln Leu Arg Gly Arg Ser Gly Arg Gln Gly Asp Pro
    530                 535                 540

Gly Tyr Thr Arg Phe Tyr Leu Ser Leu Glu Asp Asp Leu Met Lys Arg
545                 550                 555                 560

Phe Gly Gly Asp Arg Val Lys Asp Phe Leu Asp Arg Leu Ser Asp Asn
                565                 570                 575

Asp Asp Glu Lys Val Ile Glu Ser Arg Leu Ile Thr Arg Gln Val Glu
            580                 585                 590

Ser Ala Gln Lys Arg Val Glu Gly Asn Asn Tyr Asp Thr Arg Lys Gln
        595                 600                 605

Thr Leu Gln Tyr Asp Asp Val Met Arg Ile Gln Arg Glu Ile Ile Tyr
    610                 615                 620

Gly Glu Arg Met Gln Val Ile Glu Ala Asp Lys Ser Leu Lys Asn Val
625                 630                 635                 640

Leu Ile Pro Met Ile His Arg Thr Ile Asn Ser Gln Val Asp Met Phe
                645                 650                 655

Thr Gln Gly Asp Arg Ser Gln Trp Arg Leu Asp Ser Leu Arg Asp Phe
            660                 665                 670
```

```
Ile Ser Ser Ser Leu Ala Ser Glu Gln Val Thr Asp Ser Ile Asp Phe
        675                 680                 685

Lys Thr Ile Ser Val Glu Asp Leu Lys Lys Lys Leu Tyr Asp Ile Val
    690                 695                 700

Glu Lys Asn Phe Glu Asp Lys Glu Lys Ala Leu Gly Asp Pro Ser Gln
705                 710                 715                 720

Met Leu Glu Phe Glu Lys Val Val Ile Leu Arg Val Val Asp Asp Arg
                725                 730                 735

Trp Thr Asp His Ile Asp Ala Met Asp Gln Leu Arg Gln Ser Ile Gly
            740                 745                 750

Leu Arg Gly Tyr Gly Gln Leu Asn Pro Leu Val Glu Tyr Gln Asp Ser
        755                 760                 765

Gly Tyr Arg Met Phe Glu Glu Met Ile Ser Asn Ile Glu Phe Asp Val
    770                 775                 780

Thr Arg Leu Phe Met Lys Ala Glu Ile Arg Gln Asn Leu Ser Arg
785                 790                 795


<210> SEQ ID NO 47
<211> LENGTH: 843
<212> TYPE: PRT
<213> ORGANISM: Staphylococcus aureus MW2

<400> SEQUENCE: 47

Met Gly Phe Leu Ser Lys Ile Leu Asp Gly Asn Asn Lys Glu Ile Lys
1               5                   10                  15

Gln Leu Gly Lys Leu Ala Asp Lys Val Ile Ala Leu Glu Glu Lys Thr
            20                  25                  30

Ala Ile Leu Thr Asp Glu Glu Ile Arg Asn Lys Thr Lys Gln Phe Gln
        35                  40                  45

Thr Glu Leu Ala Asp Ile Asp Asn Val Lys Lys Gln Asn Asp Tyr Leu
    50                  55                  60

Asp Lys Ile Leu Pro Glu Ala Tyr Ala Leu Val Arg Glu Gly Ser Lys
65                  70                  75                  80

Arg Val Phe Asn Met Thr Pro Tyr Lys Val Gln Ile Met Gly Gly Ile
                85                  90                  95

Ala Ile His Lys Gly Asp Ile Ala Glu Met Arg Thr Gly Glu Gly Lys
            100                 105                 110

Thr Leu Thr Ala Thr Met Pro Thr Tyr Leu Asn Ala Leu Ala Gly Arg
        115                 120                 125

Gly Val His Val Ile Thr Val Asn Glu Tyr Leu Ser Ser Val Gln Ser
    130                 135                 140

Glu Glu Met Ala Glu Leu Tyr Asn Phe Leu Gly Leu Thr Val Gly Leu
145                 150                 155                 160

Asn Leu Asn Ser Lys Thr Thr Glu Glu Lys Arg Glu Ala Tyr Ala Gln
                165                 170                 175

Asp Ile Thr Tyr Ser Thr Asn Asn Glu Leu Gly Phe Asp Tyr Leu Arg
            180                 185                 190

Asp Asn Met Val Asn Tyr Ser Glu Asp Arg Val Met Arg Pro Leu His
        195                 200                 205

Phe Ala Ile Ile Asp Glu Val Asp Ser Ile Leu Ile Asp Glu Ala Arg
    210                 215                 220

Thr Pro Leu Ile Ile Ser Gly Glu Ala Glu Lys Ser Thr Ser Leu Tyr
225                 230                 235                 240

Thr Gln Ala Asn Val Phe Ala Lys Met Leu Lys Gln Asp Glu Asp Tyr
                245                 250                 255
```

```
Lys Tyr Asp Glu Lys Thr Lys Ala Val His Leu Thr Glu Gln Gly Ala
            260                 265                 270

Asp Lys Ala Glu Arg Met Phe Lys Val Glu Asn Leu Tyr Asp Val Gln
        275                 280                 285

Asn Val Asp Val Ile Ser His Ile Asn Thr Ala Leu Arg Ala His Val
    290                 295                 300

Thr Leu Gln Arg Asp Val Asp Tyr Met Val Val Asp Gly Glu Val Leu
305                 310                 315                 320

Ile Val Asp Gln Phe Thr Gly Arg Thr Met Pro Gly Arg Arg Phe Ser
                325                 330                 335

Glu Gly Leu His Gln Ala Ile Glu Ala Lys Glu Gly Val Gln Ile Gln
            340                 345                 350

Asn Glu Ser Lys Thr Met Ala Ser Ile Thr Phe Gln Asn Tyr Phe Arg
        355                 360                 365

Met Tyr Asn Lys Leu Ala Gly Met Thr Gly Thr Ala Lys Thr Glu Glu
    370                 375                 380

Glu Glu Phe Arg Asn Ile Tyr Asn Met Thr Val Thr Gln Ile Pro Thr
385                 390                 395                 400

Asn Lys Pro Val Gln Arg Asn Asp Lys Ser Asp Leu Ile Tyr Ile Ser
                405                 410                 415

Gln Lys Gly Lys Phe Asp Ala Val Val Glu Asp Val Val Glu Lys His
            420                 425                 430

Lys Ala Gly Gln Pro Val Leu Leu Gly Thr Val Ala Val Glu Thr Ser
        435                 440                 445

Glu Tyr Ile Ser Asn Leu Leu Lys Lys Arg Gly Ile Arg His Asp Val
    450                 455                 460

Leu Asn Ala Lys Asn His Glu Arg Glu Ala Glu Ile Val Ala Gly Ala
465                 470                 475                 480

Gly Gln Lys Gly Ala Val Thr Ile Ala Thr Asn Met Ala Gly Arg Gly
                485                 490                 495

Thr Asp Ile Lys Leu Gly Glu Gly Val Glu Glu Leu Gly Gly Leu Ala
            500                 505                 510

Val Ile Gly Thr Glu Arg His Glu Ser Arg Arg Ile Asp Asp Gln Leu
        515                 520                 525

Arg Gly Arg Ser Gly Arg Gln Gly Asp Lys Gly Asp Ser Arg Phe Tyr
    530                 535                 540

Leu Ser Leu Gln Asp Glu Leu Met Ile Arg Phe Gly Ser Glu Arg Leu
545                 550                 555                 560

Gln Lys Met Met Ser Arg Leu Gly Leu Asp Asp Ser Thr Pro Ile Glu
                565                 570                 575

Ser Lys Met Val Ser Arg Ala Val Glu Ser Ala Gln Lys Arg Val Glu
            580                 585                 590

Gly Asn Asn Phe Asp Ala Arg Lys Arg Ile Leu Glu Tyr Asp Glu Val
        595                 600                 605

Leu Arg Lys Gln Arg Glu Ile Ile Tyr Asn Glu Arg Asn Ser Ile Ile
    610                 615                 620

Asp Glu Glu Asp Ser Ser Gln Val Val Asp Ala Met Leu Arg Ser Thr
625                 630                 635                 640

Leu Gln Arg Ser Ile Asn Tyr Tyr Ile Asn Thr Ala Asp Asp Glu Pro
                645                 650                 655

Glu Tyr Gln Pro Phe Ile Asp Tyr Ile Asn Asp Ile Phe Leu Gln Glu
            660                 665                 670
```

```
Gly Asp Ile Thr Glu Asp Asp Ile Lys Gly Lys Asp Ala Glu Asp Ile
        675                 680                 685

Phe Glu Val Val Trp Ala Lys Ile Glu Ala Ala Tyr Gln Ser Gln Lys
    690                 695                 700

Asp Ile Leu Glu Glu Gln Met Asn Glu Phe Glu Arg Met Ile Leu Leu
705                 710                 715                 720

Arg Ser Ile Asp Ser His Trp Thr Asp His Ile Asp Thr Met Asp Gln
                725                 730                 735

Leu Arg Gln Gly Ile His Leu Arg Ser Tyr Ala Gln Gln Asn Pro Leu
            740                 745                 750

Arg Asp Tyr Gln Asn Glu Gly His Glu Leu Phe Asp Ile Met Met Gln
        755                 760                 765

Asn Ile Glu Glu Asp Thr Cys Lys Phe Ile Leu Lys Ser Val Val Gln
    770                 775                 780

Val Glu Asp Asn Ile Glu Arg Glu Lys Thr Thr Glu Phe Gly Glu Ala
785                 790                 795                 800

Lys His Val Ser Ala Glu Asp Gly Lys Glu Lys Val Lys Pro Lys Pro
                805                 810                 815

Ile Val Lys Gly Asp Gln Val Gly Arg Asn Asp Asp Cys Pro Cys Gly
            820                 825                 830

Ser Gly Lys Lys Phe Lys Asn Cys His Gly Lys
        835                 840


<210> SEQ ID NO 48
<211> LENGTH: 845
<212> TYPE: PRT
<213> ORGANISM: Corynebacterium glutamicum DSM 20300

<400> SEQUENCE: 48

Met Phe Gly Leu Ser Lys Val Leu Arg Val Gly Glu Gly Arg Ala Val
1               5                   10                  15

Lys Arg Leu His Lys Ile Ala Asp Gln Val Ile Ala Leu Glu Asp Lys
            20                  25                  30

Phe Ala Asn Leu Thr Asp Glu Glu Leu Lys Ala Lys Thr Ala Glu Phe
        35                  40                  45

Lys Glu Arg Ile Ala Gly Gly Glu Gly Leu Asp Glu Ile Phe Leu Glu
    50                  55                  60

Ala Phe Ala Thr Ala Arg Glu Ala Ala Trp Arg Val Leu Gly Gln Lys
65                  70                  75                  80

His Tyr His Val Gln Ile Met Gly Gly Ala Ala Leu His Phe Gly Asn
                85                  90                  95

Val Ala Glu Met Arg Thr Gly Glu Gly Lys Thr Leu Thr Cys Val Leu
            100                 105                 110

Pro Ala Tyr Leu Asn Ala Leu Glu Gly Lys Gly Val His Val Val Thr
        115                 120                 125

Val Asn Asp Tyr Leu Ala Lys Arg Asp Ala Glu Met Met Gly Arg Val
    130                 135                 140

His Arg Tyr Leu Gly Leu Glu Val Gly Val Ile Leu Ser Asp Met Arg
145                 150                 155                 160

Pro Asp Glu Arg Arg Glu Ala Tyr Ala Ala Asp Ile Thr Tyr Gly Thr
                165                 170                 175

Asn Asn Glu Leu Gly Phe Asp Tyr Leu Arg Asp Asn Met Ala Arg Ser
            180                 185                 190

Leu Ser Asp Leu Val Gln Arg Gly His Asn Tyr Ala Ile Val Asp Glu
        195                 200                 205
```

```
Val Asp Ser Ile Leu Ile Asp Glu Ala Arg Thr Pro Leu Ile Ile Ser
    210                 215                 220

Gly Pro Val Asp Gly Thr Ser Gln Phe Tyr Asn Val Phe Ala Gln Ile
225                 230                 235                 240

Val Pro Arg Met Thr Lys Asp Val His Tyr Glu Val Asp Glu Arg Lys
                245                 250                 255

Lys Thr Val Gly Val Lys Glu Glu Gly Val Glu Tyr Val Glu Asp Gln
            260                 265                 270

Leu Gly Ile Asp Asn Leu Tyr Ala Pro Glu His Ser Gln Leu Val Ser
        275                 280                 285

Tyr Leu Asn Asn Ala Ile Lys Ala Gln Glu Leu Phe Thr Arg Asp Lys
    290                 295                 300

Asp Tyr Ile Val Arg Asn Gly Glu Val Met Ile Val Asp Gly Phe Thr
305                 310                 315                 320

Gly Arg Val Leu Ala Gly Arg Arg Tyr Asn Glu Gly Met His Gln Ala
                325                 330                 335

Ile Glu Ala Lys Glu Arg Val Glu Ile Lys Asn Glu Asn Gln Thr Leu
            340                 345                 350

Ala Thr Val Thr Leu Gln Asn Tyr Phe Arg Leu Tyr Thr Lys Leu Ala
        355                 360                 365

Gly Met Thr Gly Thr Ala Glu Thr Glu Ala Ala Glu Leu Asn Gln Ile
    370                 375                 380

Tyr Lys Leu Asp Val Ile Ala Ile Pro Thr Asn Arg Pro Asn Gln Arg
385                 390                 395                 400

Glu Asp Leu Thr Asp Leu Val Tyr Lys Thr Gln Glu Ala Lys Phe Ala
                405                 410                 415

Ala Val Val Asp Asp Ile Ala Glu Arg Thr Glu Lys Gly Gln Pro Val
            420                 425                 430

Leu Val Gly Thr Val Ser Val Glu Arg Ser Glu Tyr Leu Ser Gln Leu
        435                 440                 445

Leu Thr Lys Arg Gly Ile Lys His Asn Val Leu Asn Ala Lys His His
    450                 455                 460

Glu Gln Glu Ala Gln Ile Val Ala Gln Ala Gly Leu Pro Gly Ala Val
465                 470                 475                 480

Thr Val Ala Thr Asn Met Ala Gly Arg Gly Thr Asp Ile Val Leu Gly
                485                 490                 495

Gly Asn Pro Glu Ile Leu Leu Asp Ile Lys Leu Arg Glu Arg Gly Leu
            500                 505                 510

Asp Pro Phe Glu Asp Glu Glu Ser Tyr Gln Glu Ala Trp Asp Ala Glu
        515                 520                 525

Leu Pro Ala Met Lys Gln Arg Cys Glu Glu Arg Gly Asp Lys Val Arg
    530                 535                 540

Glu Ala Gly Gly Leu Tyr Val Leu Gly Thr Glu Arg His Glu Ser Arg
545                 550                 555                 560

Arg Ile Asp Asn Gln Leu Arg Gly Arg Ser Ala Arg Gln Gly Asp Pro
                565                 570                 575

Gly Ser Thr Arg Phe Tyr Leu Ser Met Arg Asp Asp Leu Met Val Arg
            580                 585                 590

Phe Val Gly Pro Thr Met Glu Asn Met Met Asn Arg Leu Asn Val Pro
        595                 600                 605

Asp Asp Val Pro Ile Glu Ser Lys Thr Val Thr Asn Ser Ile Lys Gly
    610                 615                 620
```

```
Ala Gln Ala Gln Val Glu Asn Gln Asn Phe Glu Met Arg Lys Asn Val
625                 630                 635                 640

Leu Lys Tyr Asp Glu Val Met Asn Glu Gln Arg Lys Val Ile Tyr Ser
                645                 650                 655

Glu Arg Arg Glu Ile Leu Glu Ser Ala Asp Ile Ser Arg Tyr Ile Gln
            660                 665                 670

Asn Met Ile Glu Glu Thr Val Ser Ala Tyr Val Asp Gly Ala Thr Ala
        675                 680                 685

Asn Gly Tyr Val Glu Asp Trp Asp Leu Asp Lys Leu Trp Asn Ala Leu
    690                 695                 700

Glu Ala Leu Tyr Asp Pro Ser Ile Asn Trp Thr Asp Leu Val Glu Gly
705                 710                 715                 720

Ser Glu Tyr Gly Lys Pro Gly Glu Leu Ser Ala Glu Asp Leu Arg Thr
                725                 730                 735

Ala Leu Val Asn Asp Ala His Ala Glu Tyr Ala Lys Leu Glu Glu Ala
            740                 745                 750

Val Ser Ala Ile Gly Gly Glu Ala Gln Ile Arg Asn Ile Glu Arg Met
        755                 760                 765

Val Leu Met Pro Val Ile Asp Thr Lys Trp Arg Glu His Leu Tyr Glu
    770                 775                 780

Met Asp Tyr Leu Lys Glu Gly Ile Gly Leu Arg Ala Met Ala Gln Arg
785                 790                 795                 800

Asp Pro Leu Val Glu Tyr Gln Lys Glu Gly Gly Asp Met Phe Asn Gly
                805                 810                 815

Met Lys Asp Gly Ile Lys Glu Glu Thr Val Arg Gln Leu Phe Leu Leu
            820                 825                 830

Arg Lys Gln Phe Ile Lys Gln Asp Ala Glu Val Ala Asp
        835                 840                 845


<210> SEQ ID NO 49
<211> LENGTH: 911
<212> TYPE: PRT
<213> ORGANISM: Pseudomonas putida GB-1

<400> SEQUENCE: 49

Met Phe Ala Pro Leu Leu Lys Lys Leu Phe Gly Ser Lys Asn Glu Arg
1               5                   10                  15

Glu Val Lys Arg Met Leu Lys Thr Val Ser Ile Val Asn Ala Phe Glu
            20                  25                  30

Glu Lys Met Val Ala Leu Ser Asp Glu Gln Leu Arg Gly Lys Thr Ala
        35                  40                  45

Glu Phe Lys Glu Arg Leu Ala Lys Gly Glu Thr Leu Asp Gln Leu Leu
    50                  55                  60

Pro Glu Ala Phe Ala Val Ala Arg Glu Ala Gly Lys Arg Val Met Gly
65                  70                  75                  80

Met Arg His Phe Asp Val Gln Leu Ile Gly Gly Met Thr Leu His Glu
                85                  90                  95

Gly Met Ile Ala Glu Met Arg Thr Gly Glu Gly Lys Thr Leu Val Gly
            100                 105                 110

Thr Leu Ala Val Tyr Leu Asn Ala Leu Ser Gly Lys Gly Val His Val
        115                 120                 125

Val Thr Val Asn Asp Tyr Leu Ala Arg Arg Asp Ala Asn Trp Met Arg
    130                 135                 140

Pro Leu Tyr Glu Phe Leu Gly Leu Ser Val Gly Ile Val Ser Ala Phe
145                 150                 155                 160
```

-continued

```
Gln Pro Pro Glu Glu Lys Arg Ala Ala Tyr Ala Ser Asp Ile Thr Tyr
                165                 170                 175

Gly Thr Asn Asn Glu Phe Gly Phe Asp Tyr Leu Arg Asp Asn Met Ala
            180                 185                 190

Phe Ser Gln Glu Glu Lys Phe Gln Arg Glu Leu Asn Phe Ala Val Ile
        195                 200                 205

Asp Glu Val Asp Ser Ile Leu Ile Asp Glu Ala Arg Thr Pro Leu Ile
    210                 215                 220

Ile Ser Gly Gln Ala Glu Asp Ser Ser Lys Leu Tyr Ile Glu Ile Asn
225                 230                 235                 240

Arg Leu Ile Pro Arg Leu Thr Gln His Ile Glu Glu Val Glu Gly Gln
                245                 250                 255

Val Thr Gln Glu Gly His Phe Thr Ile Asp Glu Lys Ser Arg Gln Val
            260                 265                 270

Glu Leu Asn Glu Ala Gly His Gln Phe Ile Glu Glu Met Leu Thr Gln
        275                 280                 285

Ala Gly Leu Leu Ala Glu Gly Glu Ser Leu Tyr Ser Ala His Asn Leu
    290                 295                 300

Gly Leu Leu Thr His Val Tyr Ala Gly Leu Arg Ala His Lys Leu Phe
305                 310                 315                 320

His Arg Asn Val Glu Tyr Ile Val Gln Asp Gly Gln Val Leu Leu Ile
                325                 330                 335

Asp Glu His Thr Gly Arg Thr Met Pro Gly Arg Arg Leu Ser Glu Gly
            340                 345                 350

Leu His Gln Ala Ile Glu Ala Lys Glu Asn Leu Asn Ile Gln Ala Glu
        355                 360                 365

Ser Gln Thr Leu Ala Ser Thr Thr Phe Gln Asn Tyr Phe Arg Leu Tyr
    370                 375                 380

Thr Lys Leu Ser Gly Met Thr Gly Thr Ala Asp Thr Glu Ala Phe Glu
385                 390                 395                 400

Phe Gln Ser Ile Tyr Ala Leu Asn Val Met Val Ile Pro Pro Asn Lys
                405                 410                 415

Pro Leu Ala Arg Lys Asp Phe Asn Asp Leu Val Tyr Leu Thr Ala Asp
            420                 425                 430

Glu Lys Tyr Ala Ala Ile Ile Ala Asp Ile Lys Glu Ser Met Thr Lys
        435                 440                 445

Gly Arg Pro Ile Leu Val Gly Thr Ala Thr Ile Glu Thr Ser Glu His
    450                 455                 460

Met Ser Asn Leu Leu Lys Lys Glu Gly Ile Asp His Lys Val Leu Asn
465                 470                 475                 480

Ala Lys Tyr His Glu Lys Glu Ala Glu Ile Ile Ala Gln Ala Gly Ala
                485                 490                 495

Pro Gly Ala Leu Thr Ile Ala Thr Asn Met Ala Gly Arg Gly Thr Asp
            500                 505                 510

Ile Leu Leu Gly Gly Asn Trp Glu Ala Glu Val Ala Ala Leu Glu Asn
        515                 520                 525

Pro Ser Ala Glu Gln Ile Ala Gln Ile Lys Ala Asp Trp Gln Lys Arg
    530                 535                 540

His Gln Gln Val Ile Glu Ala Gly Gly Leu His Val Ile Ala Ser Glu
545                 550                 555                 560

Arg His Glu Ser Arg Arg Ile Asp Asn Gln Leu Arg Gly Arg Ser Gly
                565                 570                 575
```

```
Arg Gln Gly Asp Pro Gly Ser Ser Arg Phe Tyr Leu Ser Leu Glu Asp
            580                 585                 590

Ser Leu Met Arg Ile Phe Ala Ser Asp Arg Val Lys Asn Phe Met Lys
        595                 600                 605

Ala Leu Gly Met Gln Ser Gly Glu Ala Ile Glu His Arg Met Val Thr
    610                 615                 620

Asn Ala Ile Glu Lys Ala Gln Arg Lys Val Glu Gly Arg Asn Phe Asp
625                 630                 635                 640

Ile Arg Lys Gln Leu Leu Glu Tyr Asp Asp Val Ala Asn Glu Gln Arg
                645                 650                 655

Lys Val Ile Tyr His Met Arg Asn Ser Leu Leu Ala Ala Glu Asn Ile
            660                 665                 670

Gly Asp Thr Ile Val Glu Phe Arg Gln Glu Val Leu Asp Ala Thr Ile
        675                 680                 685

Ser Gln His Ile Pro Pro Gln Ser Leu Pro Glu Gln Trp Asp Val Ala
    690                 695                 700

Gly Leu Glu Ala Ser Leu Ala Ser Asp Phe Ala Met Lys Leu Pro Ile
705                 710                 715                 720

Gln Gln Trp Leu Asp Glu Asp Asp His Leu Tyr Glu Glu Thr Leu Arg
                725                 730                 735

Glu Lys Leu Leu Asn Glu Ile Thr Thr Ala Tyr Thr Glu Lys Glu Asp
            740                 745                 750

Gln Ala Gly Ile Glu Ala Leu Arg Thr Phe Glu Lys Gln Ile Leu Leu
        755                 760                 765

Arg Val Leu Asp Asp Leu Trp Lys Asp His Leu Ser Thr Met Asp His
    770                 775                 780

Leu Arg His Gly Ile His Leu Arg Gly Tyr Ala Gln Lys Asn Pro Lys
785                 790                 795                 800

Gln Glu Tyr Lys Arg Glu Ser Phe Ser Leu Phe Gln Glu Leu Leu Glu
                805                 810                 815

Ser Ile Lys Arg Asp Thr Ile Arg Val Leu Ser His Val Gln Val Arg
            820                 825                 830

Arg Glu Asp Pro Ile Glu Glu Glu Ala Arg Leu Arg Arg Glu Ala Glu
        835                 840                 845

Glu Leu Ala Ser Arg Met Gln Phe Gln His Ala Ala Ala Pro Gly Leu
    850                 855                 860

Glu Ser Glu Gln Leu Ser Glu Glu Gly Ala Glu Val Ala Val Ala Ala
865                 870                 875                 880

Ala Pro Val Arg Asn Asp Gln Lys Leu Gly Arg Asn Glu Pro Cys Trp
                885                 890                 895

Cys Gly Ser Gly Lys Lys Phe Lys His Cys His Gly Gln Ile Glu
            900                 905                 910


<210> SEQ ID NO 50
<211> LENGTH: 947
<212> TYPE: PRT
<213> ORGANISM: Streptomyces coelicolor A3(2)

<400> SEQUENCE: 50

Met Ser Val Leu Ser Lys Leu Met Arg Ala Gly Glu Gly Lys Ile Leu
1               5                   10                  15

Arg Lys Leu His Arg Ile Ala Asp Gln Val Asn Ser Ile Glu Glu Asp
            20                  25                  30

Phe Ala Asp Leu Ser Asp Ala Glu Leu Arg Ala Leu Thr Asp Glu Tyr
        35                  40                  45
```

```
Lys Gln Arg Tyr Ala Asp Gly Glu Ser Leu Asp Asp Leu Leu Pro Glu
    50                  55                  60

Ala Phe Ala Thr Val Arg Glu Ala Ala Lys Arg Val Leu Gly Gln Arg
65                  70                  75                  80

His Tyr Asp Val Gln Ile Met Gly Gly Ala Ala Leu His Met Gly Tyr
                85                  90                  95

Val Ala Glu Met Lys Thr Gly Glu Gly Lys Thr Leu Val Gly Thr Leu
            100                 105                 110

Pro Ala Tyr Leu Asn Ala Leu Ser Gly Glu Gly Val His Ile Val Thr
        115                 120                 125

Val Asn Asp Tyr Leu Ala Glu Arg Asp Ser Glu Leu Met Gly Arg Val
    130                 135                 140

His Lys Phe Leu Gly Leu Asn Val Gly Cys Ile Leu Ala Asn Gln Thr
145                 150                 155                 160

Pro Ala Gln Arg Arg Glu Met Tyr Ala Cys Asp Ile Thr Tyr Gly Thr
                165                 170                 175

Asn Asn Glu Phe Gly Phe Asp Tyr Leu Arg Asp Asn Met Ala Trp Ser
            180                 185                 190

Lys Asp Glu Leu Val Gln Arg Gly His Asn Phe Ala Ile Val Asp Glu
        195                 200                 205

Val Asp Ser Ile Leu Val Asp Glu Ala Arg Thr Pro Leu Ile Ile Ser
    210                 215                 220

Gly Pro Ala Asp Gln Ala Thr Lys Trp Tyr Gly Asp Phe Ala Lys Leu
225                 230                 235                 240

Val Thr Arg Leu Lys Lys Gly Glu Ala Gly Asn Thr Leu Lys Gly Ile
                245                 250                 255

Glu Glu Thr Gly Asp Tyr Glu Val Asp Glu Lys Lys Arg Thr Val Ala
            260                 265                 270

Ile His Glu Ser Gly Val Ala Lys Val Glu Asp Trp Leu Gly Ile Asp
        275                 280                 285

Asn Leu Tyr Glu Ser Val Asn Thr Pro Leu Val Gly Tyr Leu Asn Asn
    290                 295                 300

Ala Ile Lys Ala Lys Glu Leu Phe Lys Lys Asp Lys Asp Tyr Val Val
305                 310                 315                 320

Leu Asp Gly Glu Val Met Ile Val Asp Glu His Thr Gly Arg Ile Leu
                325                 330                 335

Ala Gly Arg Arg Tyr Asn Glu Gly Met His Gln Ala Ile Glu Ala Lys
            340                 345                 350

Glu Gly Val Asp Ile Lys Asp Glu Asn Gln Thr Leu Ala Thr Ile Thr
        355                 360                 365

Leu Gln Asn Phe Phe Arg Leu Tyr Lys Arg His Asp His Asp Gly Lys
    370                 375                 380

Glu Gln Pro Gly Leu Ser Gly Met Thr Gly Thr Ala Met Thr Glu Ala
385                 390                 395                 400

Ala Glu Phe His Gln Ile Tyr Lys Leu Gly Val Val Pro Ile Pro Thr
                405                 410                 415

Asn Arg Pro Met Val Arg Lys Asp Gln Ser Asp Leu Ile Tyr Arg Thr
            420                 425                 430

Glu Val Ala Lys Phe Glu Ala Val Val Asp Asp Ile Glu Glu Lys His
        435                 440                 445

Arg Lys Gly Gln Pro Ile Leu Val Gly Thr Thr Ser Val Glu Lys Ser
    450                 455                 460
```

```
Glu Tyr Leu Ser Gln Gln Leu Ser Lys Arg Gly Val Gln His Glu Val
465                 470                 475                 480

Leu Asn Ala Lys Gln His Asp Arg Glu Ala Thr Ile Val Ala Gln Ala
                485                 490                 495

Gly Arg Lys Gly Ser Val Thr Val Ala Thr Asn Met Ala Gly Arg Gly
            500                 505                 510

Thr Asp Ile Lys Leu Gly Gly Asn Pro Glu Asp Leu Ala Glu Ala Glu
        515                 520                 525

Leu Arg Gln Arg Gly Leu Asp Pro Glu Glu His Ile Glu Glu Trp Ala
    530                 535                 540

Ala Ala Leu Pro Ala Ala Leu Glu Arg Ala Glu Gln Ala Val Lys Ala
545                 550                 555                 560

Glu Phe Glu Glu Val Lys Glu Leu Gly Gly Leu Tyr Val Leu Gly Thr
                565                 570                 575

Glu Arg His Glu Ser Arg Arg Ile Asp Asn Gln Leu Arg Gly Arg Ser
            580                 585                 590

Gly Arg Gln Gly Asp Pro Gly Glu Ser Arg Phe Tyr Leu Ser Leu Gly
        595                 600                 605

Asp Asp Leu Met Arg Leu Phe Lys Ala Gln Met Val Glu Arg Val Met
    610                 615                 620

Ser Met Ala Asn Val Pro Asp Asp Val Pro Ile Glu Asn Lys Met Val
625                 630                 635                 640

Thr Arg Ala Ile Ala Ser Ala Gln Ser Gln Val Glu Thr Gln Asn Phe
                645                 650                 655

Glu Thr Arg Lys Asn Val Leu Lys Tyr Asp Glu Val Leu Asn Arg Gln
            660                 665                 670

Arg Glu Val Ile Tyr Gly Glu Arg Arg Arg Val Leu Glu Gly Glu Asp
        675                 680                 685

Leu Gln Glu Gln Ile Gln His Phe Thr Asn Asp Thr Ile Asp Ala Tyr
    690                 695                 700

Val Gln Ala Glu Thr Ala Glu Gly Phe Pro Glu Asp Trp Asp Leu Asp
705                 710                 715                 720

Arg Leu Trp Gly Ala Phe Lys Gln Leu Tyr Pro Val Lys Val Thr Val
                725                 730                 735

Glu Glu Leu Glu Glu Ala Ala Gly Asp Arg Ala Gly Leu Thr Ala Asp
            740                 745                 750

Tyr Ile Ala Glu Ser Ile Lys Asp Asp Val Arg Glu Gln Tyr Glu Ala
        755                 760                 765

Arg Glu Lys Gln Leu Gly Ser Glu Ile Met Arg Glu Leu Glu Arg Arg
    770                 775                 780

Val Val Leu Ser Val Leu Asp Arg Lys Trp Arg Glu His Leu Tyr Glu
785                 790                 795                 800

Met Asp Tyr Leu Gln Glu Gly Ile Gly Leu Arg Ala Met Ala Gln Lys
                805                 810                 815

Asp Pro Leu Val Glu Tyr Gln Arg Glu Gly Phe Asp Met Phe Gln Ala
            820                 825                 830

Met Met Asp Gly Ile Lys Glu Glu Ser Val Gly Tyr Leu Phe Asn Leu
        835                 840                 845

Glu Val Gln Val Glu Gln Gln Val Glu Glu Val Pro Val Glu Asp Ala
    850                 855                 860

Ala Pro Ser Leu Asp Lys Gly Ala Gln Asp Ala Val Pro Ala Gln Ala
865                 870                 875                 880
```

```
Gly Ala Arg Pro Glu Ile Arg Ala Lys Gly Leu Asp Ala Pro Gln Arg
                885                 890                 895

Arg Asp Leu His Phe Ser Ala Pro Thr Val Asp Gly Glu Gly Gly Val
            900                 905                 910

Val Glu Gly Glu Phe Thr Asp Gly Glu Pro Ala Gln Ala Gln Ser Asp
        915                 920                 925

Gly Leu Thr Arg Ala Glu Arg Arg Lys Gln Ala Lys Gly Gly Arg Arg
    930                 935                 940

Arg Lys Lys
945


<210> SEQ ID NO 51
<211> LENGTH: 921
<212> TYPE: PRT
<213> ORGANISM: Gluconobacter oxydans 621H

<400> SEQUENCE: 51

Met Phe Ala Arg Leu Ala Arg Ala Leu Phe Gly Ser Ala Asn Asp Arg
1               5                   10                  15

Thr Leu Lys Ala Tyr Gln Arg Arg Val Pro Glu Ile Asn Ala Leu Glu
            20                  25                  30

Pro Ala Val Gln Ala Leu Ser Asp Glu Gln Leu Arg His Lys Thr Thr
        35                  40                  45

Glu Phe Lys Glu Arg Leu Glu Lys Gly Glu Thr Leu Asp Gly Leu Leu
    50                  55                  60

Pro Glu Ala Phe Ala Val Cys Arg Glu Ala Ser Arg Arg Val Leu Gly
65                  70                  75                  80

Lys Arg His Phe Asp Val Gln Leu Ile Gly Gly Met Val Leu His Ala
                85                  90                  95

Gly Arg Ile Ala Glu Met Arg Thr Gly Glu Gly Lys Thr Leu Val Ala
            100                 105                 110

Thr Leu Ala Val Tyr Leu Asn Ala Leu Ser Gly Lys Gly Val His Val
        115                 120                 125

Val Thr Val Asn Asp Tyr Leu Ala Arg Arg Asp Ala Glu Glu Met Ser
    130                 135                 140

Ile Leu Tyr Ser Phe Leu Gly Leu Thr Thr Gly Val Ile Val Pro Asn
145                 150                 155                 160

Leu Ser Asp Gly Glu Arg Arg Glu Ala Tyr Ala Ala Asp Ile Thr Tyr
                165                 170                 175

Gly Thr Asn Asn Glu Phe Gly Phe Asp Tyr Leu Arg Asp Asn Met Lys
            180                 185                 190

Tyr Ser Leu Ala Asp Met Val Gln Arg Pro Phe Asn His Ala Ile Val
        195                 200                 205

Asp Glu Val Asp Ser Ile Leu Ile Asp Glu Ala Arg Thr Pro Leu Ile
    210                 215                 220

Ile Ser Gly Pro Ala Asp Asp Ser Ser Asp Leu Tyr Arg Ser Val Asp
225                 230                 235                 240

Asp Val Val Val Lys Leu Val Gln Glu Pro Asp Val Tyr Asp Lys Asp
                245                 250                 255

Glu Lys Leu Arg Ser Val Thr Leu Thr Glu His Gly Ser His Arg Val
            260                 265                 270

Glu Glu Leu Leu Ala Glu Ala Gly Val Leu Gln Asp Gly Gly Leu Tyr
        275                 280                 285

Asp Ile His Asn Val Ala Val Val His His Val Gln Gln Ser Leu Arg
    290                 295                 300
```

```
Ala His Thr Leu Phe Thr Arg Asp Val Asp Tyr Ile Val Arg Asp Gly
305                 310                 315                 320

Lys Val Val Ile Ile Asp Glu Phe Thr Gly Arg Met Met Asp Gly Arg
                325                 330                 335

Arg Tyr Ser Asp Gly Leu His Gln Ala Leu Glu Ala Lys Glu His Val
            340                 345                 350

Glu Ile Gln Gln Glu Asn Gln Thr Leu Ala Ser Ile Thr Phe Gln Asn
        355                 360                 365

Tyr Phe Arg Leu Tyr Pro Lys Leu Ser Gly Met Thr Gly Thr Ala Met
    370                 375                 380

Thr Glu Ala Asp Glu Phe Ala Glu Ile Tyr His Leu Asp Val Val Glu
385                 390                 395                 400

Ile Pro Thr Asn Leu Pro Val Arg Arg Ile Asp Thr Asp Asp Glu Val
                405                 410                 415

Tyr Leu Thr Ala Ala Glu Lys Phe Ser Ala Val Ala Asp Leu Ile Lys
            420                 425                 430

Glu Ile His Glu Thr Gly Gln Pro Ile Leu Val Gly Thr Thr Ser Ile
        435                 440                 445

Glu Lys Ser Glu Tyr Leu Ser His Ile Leu Thr Gln Arg Gly Ile Pro
    450                 455                 460

His Asn Val Leu Asn Ala Arg Gln His Glu Lys Glu Ala Ile Ile Val
465                 470                 475                 480

Ala Gln Ala Gly Ala Pro Gly Ala Ile Thr Ile Ala Thr Asn Met Ala
                485                 490                 495

Gly Arg Gly Thr Asp Ile Lys Leu Gly Gly Asn Ile Glu Met Leu Val
            500                 505                 510

Lys Ala Ser Thr Glu Gly Val Glu Asp Glu Ala Gln Arg Glu Ser Val
        515                 520                 525

Glu Gln Asn Ile Arg Ala Ile Val Glu Glu His His Glu Glu Val His
    530                 535                 540

Lys Ala Gly Gly Leu Tyr Val Ile Gly Thr Glu Arg His Glu Ser Arg
545                 550                 555                 560

Arg Val Asp Asn Gln Leu Arg Gly Arg Ser Gly Arg Gln Gly Asp Pro
                565                 570                 575

Gly Asn Ser Arg Phe Phe Leu Ser Leu Glu Asp Asp Leu Ile Arg Ile
            580                 585                 590

Phe Ala Ser Asp Arg Met Gly Ala Met Met Gln Lys Met Gly Leu Lys
        595                 600                 605

Glu Gly Glu Ala Ile Val His Pro Trp Leu Asn Lys Ala Leu Glu Lys
    610                 615                 620

Ala Gln Lys Arg Val Glu Ala Arg Asn Phe Asp Met Arg Lys Asn Thr
625                 630                 635                 640

Leu Lys Tyr Asp Asp Val Met Asn Asp Gln Arg Lys Glu Val Tyr Ala
                645                 650                 655

Gln Arg Arg Glu Tyr Met Ala Thr Asp Asp Leu Ser Gly Val Ile Ala
            660                 665                 670

Glu Leu Arg Glu His Thr Ile Glu Asp Leu Val His Ala His Ile Pro
        675                 680                 685

Glu Lys Ser Phe Ala Glu Ala Trp Asp Thr Glu Gly Leu Thr Lys Glu
    690                 695                 700

Val Ser Arg Ile Leu Asn Leu Asp Leu Pro Ile Ala Asp Trp Ala Lys
705                 710                 715                 720
```

```
Glu Asp Gly Met Asp Ser Glu Gly Val Ile Glu Arg Ile Glu Ala Glu
                725                 730                 735

Ala Ala Lys Ala Gln Ala Ala Arg Thr Ala Asn Met Gly Pro Glu Leu
                740                 745                 750

Met Arg Leu Ile Glu Lys Gln Val Val Leu Thr Thr Phe Asp Ala Val
        755                 760                 765

Trp Lys Glu Tyr Leu His Gly Leu Asp Gln Leu Arg Gln Gly Ile Gly
    770                 775                 780

Leu Arg Ala Tyr Gly Gln Arg Asp Pro Leu Asn Glu Tyr Lys Gln Glu
785                 790                 795                 800

Ala Phe Gln Met Phe Thr Ala Met Leu Asp Asp Met Arg Ile Arg Val
                805                 810                 815

Thr Glu Thr Met Cys Arg Ile Gln Ala Val Ser Glu Pro Pro Pro Phe
                820                 825                 830

Pro Val Ile Asn Thr Glu Thr Ser Gly Pro Ser Glu Glu Pro Ala Gly
        835                 840                 845

Leu Phe Ser Gln Gly Thr Thr Gly Gly Asp Ile Pro Ala Pro Gln Pro
    850                 855                 860

Met Ala Gly Phe Pro Ser Ala Ala Pro Met Pro Pro Arg Pro Gln Pro
865                 870                 875                 880

Val Pro Thr Gly Ala Glu Pro Asp Ala Ala Thr Leu Gln Arg Trp Tyr
                885                 890                 895

Ala Glu Thr Pro Arg Asn Ala Leu Cys Pro Cys Gly Ser Gly Leu Lys
                900                 905                 910

Phe Lys His Cys His Gly Arg Leu Ala
        915                 920


<210> SEQ ID NO 52
<211> LENGTH: 839
<212> TYPE: PRT
<213> ORGANISM: Clostridium acetobutylicum DSM 792

<400> SEQUENCE: 52

Met Gly Leu Leu Glu Lys Ile Phe Gly Thr Tyr Ser Asp Arg Glu Val
1               5                   10                  15

Lys Arg Ile Ile Pro Leu Val Asp Lys Ile Asp Ala Leu Asp Gly Ser
            20                  25                  30

Met Gln Ala Leu Ser Glu Asp Glu Leu Lys Ala Lys Thr Ala Glu Phe
        35                  40                  45

Lys Gln Arg Tyr Glu Asn Gly Glu Thr Leu Asp Asp Leu Leu Val Glu
    50                  55                  60

Ala Phe Ala Val Val Arg Glu Ala Ser Ser Arg Ile Leu Gly Leu Lys
65                  70                  75                  80

His Phe Arg Glu Gln Ile Ile Gly Gly Ile Val Leu His Gln Gly Arg
                85                  90                  95

Ile Ser Glu Met Lys Thr Gly Glu Gly Lys Thr Leu Val Ala Thr Leu
            100                 105                 110

Pro Ser Tyr Leu Asn Ala Ile Thr Gly Lys Gly Val His Val Val Thr
        115                 120                 125

Val Asn Asp Tyr Leu Ala Lys Arg Asp Met Glu Trp Met Gly Gln Leu
    130                 135                 140

Tyr Gln Tyr Leu Gly Leu Thr Thr Gly Val Ile Val His Asp Leu Asp
145                 150                 155                 160

Gln Lys Gln Arg Gln Glu Ala Tyr Ala Ala Asp Ile Thr Tyr Gly Thr
                165                 170                 175
```

-continued

```
Asn Asn Glu Phe Gly Phe Asp Tyr Leu Arg Asp Asn Met Val Ile Tyr
            180                 185                 190

Lys Glu Glu Arg Val Gln Arg Pro Leu His Phe Cys Ile Val Asp Glu
        195                 200                 205

Val Asp Ser Ile Leu Ile Asp Glu Ala Arg Thr Pro Leu Ile Ile Ser
    210                 215                 220

Gly Glu Gly Glu Lys Ser Thr Glu Phe Tyr Lys Val Ala Asp Asn Phe
225                 230                 235                 240

Ala Lys Met Leu Arg Lys Glu Lys Asp Phe Thr Ile Asp Glu Lys Thr
                245                 250                 255

Asn Ser Ala Ile Leu Thr Asp Glu Gly Val Glu Lys Ala Glu Lys Tyr
            260                 265                 270

Tyr His Ile Asp Asn Tyr Ala Asp Pro Gln Asn Met Glu Ile Gln His
        275                 280                 285

His Thr Ser Gln Ala Leu Lys Ala Asn Tyr Leu Met Lys Arg Asp Lys
    290                 295                 300

Asp Tyr Met Val Lys Glu Asp Glu Val Val Ile Val Asp Glu Phe Thr
305                 310                 315                 320

Gly Arg Leu Met Glu Gly Arg Arg Tyr Ser Asp Gly Leu His Gln Ala
                325                 330                 335

Ile Glu Ala Lys Glu Gly Val Lys Val Gln Lys Glu Ser Lys Thr Leu
            340                 345                 350

Ala Thr Ile Thr Phe Gln Asn Tyr Phe Arg Met Tyr Glu Lys Leu Ser
        355                 360                 365

Gly Met Thr Gly Thr Ala Leu Thr Glu Glu Val Glu Phe Arg Glu Ile
    370                 375                 380

Tyr Gly Leu Asp Val Val Val Ile Pro Thr His Arg Pro Ile Ala Arg
385                 390                 395                 400

Ile Asp Ala Pro Asp Ile Val Tyr Lys Thr Glu Leu Gly Lys Phe Lys
                405                 410                 415

Ala Val Val Glu Asp Ile Val Glu Thr Asn Lys Asn Gly Gln Pro Val
            420                 425                 430

Leu Val Gly Thr Val Ser Ile Glu Lys Ser Glu Leu Leu Ser Ser Leu
        435                 440                 445

Leu Lys Lys Arg Gly Val Arg His Gln Val Leu Asn Ala Lys Tyr His
    450                 455                 460

Glu Gln Glu Ala Glu Ile Ile Ser His Ala Gly Glu Lys Gly Met Val
465                 470                 475                 480

Thr Ile Ala Thr Asn Met Ala Gly Arg Gly Thr Asp Ile Lys Leu Gly
                485                 490                 495

Glu Gly Val Thr Asp Val Gly Gly Leu Lys Ile Ile Gly Thr Glu Arg
            500                 505                 510

His Glu Ser Arg Arg Ile Asp Asn Gln Leu Arg Gly Arg Ala Gly Arg
        515                 520                 525

Gln Gly Asp Lys Gly Tyr Ser Arg Phe Tyr Val Ser Leu Glu Asp Asp
    530                 535                 540

Leu Met Arg Ile Phe Gly Ser Asp Lys Leu Lys Asn Met Val Glu Lys
545                 550                 555                 560

Leu Gly Leu Gly Asp Asp Asp Ala Ile Glu Ser Lys Met Val Ser Ser
                565                 570                 575

Ala Ile Glu Asn Ala Gln Lys Lys Val Glu Gly Asn Asn Phe Asp Ile
            580                 585                 590
```

```
Arg Lys Thr Leu Ile Gln Tyr Asp Asp Val Met Asn Lys Gln Arg Glu
        595                 600                 605

Ile Ile Tyr Lys Gln Arg Ser Glu Val Leu Glu Gly Glu Asn Leu Lys
    610                 615                 620

Asp Gln Ile Glu Gly Met Ile Lys Asp Leu Ile Tyr Asn Ala Val Asn
625                 630                 635                 640

Ser His Ile Ser Gly Val Asp Glu Glu Leu Glu Ser Asp Ile Glu Ala
                645                 650                 655

Ile Leu Asn Tyr Leu Asp Asp Ile Cys Leu Pro Arg Gly Ile Val Glu
            660                 665                 670

Val Glu Glu Leu Ala Thr Met Ser Asn Asp Glu Ile Lys Glu Lys Leu
        675                 680                 685

Tyr Ser Leu Ala Lys Glu Ile Tyr Glu Arg Lys Glu Glu Glu Phe Ser
    690                 695                 700

Ser Asp Gln Met Arg Glu Leu Glu Arg Val Ile Leu Leu Arg Val Val
705                 710                 715                 720

Asp Thr Lys Trp Met Asp His Ile Asp Ser Met Glu His Leu Lys Gln
                725                 730                 735

Gly Ile Gly Leu Arg Ala Tyr Lys Gln Gln Asp Pro Thr Gln Ala Tyr
            740                 745                 750

Gln Met Glu Gly Ser Asp Met Phe Glu Glu Met Val Glu Asn Ile Lys
        755                 760                 765

Val Glu Thr Val Arg Tyr Leu Phe His Val Gln Ala Glu Arg Ala Pro
    770                 775                 780

Glu Arg Gln Arg Val Val Lys Glu Thr Glu Ile Asn Tyr Ser Gly Pro
785                 790                 795                 800

Asp Ala Gly Asp Thr Lys Lys Glu Pro Val Arg Arg Lys Glu Lys Lys
                805                 810                 815

Ile Gly Arg Asn Asp Leu Cys Pro Cys Gly Ser Gly Lys Lys Tyr Lys
            820                 825                 830

Asp Cys Cys Gly Arg Arg Ala
        835


<210> SEQ ID NO 53
<211> LENGTH: 37
<212> TYPE: DNA
<213> ORGANISM: Bacillus atrophaeus

<400> SEQUENCE: 53

aaattctttg gaaataacag aaggtatgat atgataa                              37


<210> SEQ ID NO 54
<211> LENGTH: 37
<212> TYPE: DNA
<213> ORGANISM: Bacillus subtilis

<400> SEQUENCE: 54

aaattctttg gaaatggcaa aaggtatgtt atgataa                              37


<210> SEQ ID NO 55
<211> LENGTH: 37
<212> TYPE: DNA
<213> ORGANISM: Bacillus sp.

<400> SEQUENCE: 55

aaattctttg gaaatagcaa aaggtatgtt atgataa                              37
```

<210> SEQ ID NO 56
<211> LENGTH: 37
<212> TYPE: DNA
<213> ORGANISM: Bacillus siamensis

<400> SEQUENCE: 56
aaattctttg gaaataacca aaggtatgtt atgataa 37

<210> SEQ ID NO 57
<211> LENGTH: 37
<212> TYPE: DNA
<213> ORGANISM: Bacillus sp.

<400> SEQUENCE: 57
aaattctttg gaaatgaaag aaggtatggt atgataa 37

<210> SEQ ID NO 58
<211> LENGTH: 37
<212> TYPE: DNA
<213> ORGANISM: Bacillus pumilus

<400> SEQUENCE: 58
aaattctttg gaaatgaagg aaggtatggt atgataa 37

<210> SEQ ID NO 59
<211> LENGTH: 37
<212> TYPE: DNA
<213> ORGANISM: Bacillus mojavensis

<400> SEQUENCE: 59
aaattctttg gaaattagag aaggtatgat atgataa 37

<210> SEQ ID NO 60
<211> LENGTH: 37
<212> TYPE: DNA
<213> ORGANISM: Bacillus subtilis

<400> SEQUENCE: 60
aaattctttg gaaataagag aaggtatgat atgataa 37

<210> SEQ ID NO 61
<211> LENGTH: 37
<212> TYPE: DNA
<213> ORGANISM: Bacillus sp.

<400> SEQUENCE: 61
aaattctttg gaaataacaa aaggtgtgat atgataa 37

<210> SEQ ID NO 62
<211> LENGTH: 37
<212> TYPE: DNA
<213> ORGANISM: Bacillus subtilis

<400> SEQUENCE: 62
aaattctttg gaaataacaa aaggtatgat atgataa 37

<210> SEQ ID NO 63
<211> LENGTH: 37
<212> TYPE: DNA
<213> ORGANISM: Bacillus amyloliquefaciens

<400> SEQUENCE: 63
aaattctttg gaaataacaa aaggtatgtt atgataa 37

<210> SEQ ID NO 64
<211> LENGTH: 37
<212> TYPE: DNA
<213> ORGANISM: Bacillus sp.

<400> SEQUENCE: 64
atatggtttg gaaatatcat aagatgtgat aaaataa 37

<210> SEQ ID NO 65
<211> LENGTH: 37
<212> TYPE: DNA
<213> ORGANISM: Bacillus sp.

<400> SEQUENCE: 65
aaattctttg gaaatcaagg aaggtatggt atgataa 37

<210> SEQ ID NO 66
<211> LENGTH: 37
<212> TYPE: DNA
<213> ORGANISM: Bacillus paralicheniformis

<400> SEQUENCE: 66
aaattgtttg gaaatgacaa aaggtatgat atgatat 37

<210> SEQ ID NO 67
<211> LENGTH: 37
<212> TYPE: DNA
<213> ORGANISM: Bacillus glycinifermentans

<400> SEQUENCE: 67
aaattgtttg gaaatgacaa aaggtgtgat atgatat 37

<210> SEQ ID NO 68
<211> LENGTH: 37
<212> TYPE: DNA
<213> ORGANISM: Bacillus vallismortis

<400> SEQUENCE: 68
aaattctttg gaaataaccc aaggtatgat atgataa 37

<210> SEQ ID NO 69
<211> LENGTH: 43
<212> TYPE: DNA
<213> ORGANISM: Shigella flexneri

<400> SEQUENCE: 69
tcattactgc tgtggagtgc gcgctttaat gataagattt gtg 43

<210> SEQ ID NO 70
<211> LENGTH: 43
<212> TYPE: DNA
<213> ORGANISM: Citrobacter sp.

<400> SEQUENCE: 70
tcattactgc tgtggtgcga acgcattaat ggtaatattt gtg 43

<210> SEQ ID NO 71
<211> LENGTH: 43
<212> TYPE: DNA
<213> ORGANISM: Salmonella bongori

<400> SEQUENCE: 71
tcattactgc tgttgcgtgt acgctttaat gataagattt gtg 43

<210> SEQ ID NO 72
<211> LENGTH: 43
<212> TYPE: DNA
<213> ORGANISM: Salmonella enterica

<400> SEQUENCE: 72
tcattactgc tgtagcgcgt acgctttaat gataagattt gtg 43

<210> SEQ ID NO 73
<211> LENGTH: 43
<212> TYPE: DNA
<213> ORGANISM: Citrobacter amalonaticus

<400> SEQUENCE: 73
tcaatactgc tgtagtgcct gcgcattaat gataagattt gtg 43

<210> SEQ ID NO 74
<211> LENGTH: 43
<212> TYPE: DNA
<213> ORGANISM: Escherichia albertii

<400> SEQUENCE: 74
tcattcctgc tgtggatttc aggctttaat gataagattt gtg 43

<210> SEQ ID NO 75
<211> LENGTH: 43
<212> TYPE: DNA
<213> ORGANISM: Escherichia sp.

<400> SEQUENCE: 75
tcattcctgc tgtggacttc gggctttaat gataagattt gtg 43

<210> SEQ ID NO 76
<211> LENGTH: 43
<212> TYPE: DNA
<213> ORGANISM: Escherichia sp.

<400> SEQUENCE: 76
tcattcgtgc tgtggactgc aggctttaat ggtaagattt gtg 43

<210> SEQ ID NO 77
<211> LENGTH: 43
<212> TYPE: DNA
<213> ORGANISM: Escherichia sp.

<400> SEQUENCE: 77
tcattcgtgc tgtggactgt aggctttaat gataagattt gtg 43

<210> SEQ ID NO 78
<211> LENGTH: 43
<212> TYPE: DNA
<213> ORGANISM: Escherichia sp.

<400> SEQUENCE: 78
tcattcgtgc tgtggactgc aggctttaat gataagattt ttg 43

<210> SEQ ID NO 79
<211> LENGTH: 43
<212> TYPE: DNA
<213> ORGANISM: Escherichia sp.

<400> SEQUENCE: 79
tcattcgtgc tgtggaccgc aggctttaat gataagattt gtg 43

<210> SEQ ID NO 80
<211> LENGTH: 43
<212> TYPE: DNA
<213> ORGANISM: Escherichia sp.

<400> SEQUENCE: 80
tcattcgtgc tgcggactgc aggctttaat gataagattt gtg 43

<210> SEQ ID NO 81
<211> LENGTH: 43
<212> TYPE: DNA
<213> ORGANISM: Escherichia sp.

<400> SEQUENCE: 81
tcattcgtgc tgtggactgc aggctttaat gataatattt gtg 43

<210> SEQ ID NO 82
<211> LENGTH: 43
<212> TYPE: DNA
<213> ORGANISM: Escherichia sp.

<400> SEQUENCE: 82
tcattcgtgc tgtggactgc aggctttaat gataagattt gtg 43

<210> SEQ ID NO 83
<211> LENGTH: 43
<212> TYPE: DNA
<213> ORGANISM: Shigella dysenteriae

<400> SEQUENCE: 83
tcattcatgc tgtgggcttc aggctttaat gataagattt gtg 43

<210> SEQ ID NO 84
<211> LENGTH: 43
<212> TYPE: DNA
<213> ORGANISM: Escherichia sp.

<400> SEQUENCE: 84
tcattcgtgc tgtggagttc aggctttaat gataagattt gtg 43

<210> SEQ ID NO 85
<211> LENGTH: 43
<212> TYPE: DNA
<213> ORGANISM: Escherichia sp.

<400> SEQUENCE: 85
tcattcatgc tgtggacttc aggctttaat gataagattt gtg 43

<210> SEQ ID NO 86
<211> LENGTH: 43
<212> TYPE: DNA
<213> ORGANISM: Escherichia sp.

<400> SEQUENCE: 86
tcattcgtgc tgtggacttc aggctttaat gataaaattt gtg 43

<210> SEQ ID NO 87
<211> LENGTH: 43
<212> TYPE: DNA
<213> ORGANISM: Escherichia sp.

<400> SEQUENCE: 87
tcattcgtgc tgtgggcttc aggctttaat gataagattt gtg 43

<210> SEQ ID NO 88
<211> LENGTH: 43
<212> TYPE: DNA
<213> ORGANISM: Escherichia sp.

<400> SEQUENCE: 88
tcattcgtgc tgtggacttc aggctttaat gataagattt gtg 43

<210> SEQ ID NO 89
<211> LENGTH: 43
<212> TYPE: DNA
<213> ORGANISM: Escherichia sp.

<400> SEQUENCE: 89
tcattcctgc tgtggacttc ggcctttaat gataagattt gtg 43

<210> SEQ ID NO 90
<211> LENGTH: 43
<212> TYPE: DNA
<213> ORGANISM: Escherichia sp.

<400> SEQUENCE: 90
tcattcctgc tgtggacttc aggctttaat gataagattt gtg 43

<210> SEQ ID NO 91
<211> LENGTH: 43
<212> TYPE: DNA
<213> ORGANISM: Escherichia sp.

<400> SEQUENCE: 91
tcattcctgc tgtggacttc aggctttaat ggtaagattt gtg 43

<210> SEQ ID NO 92
<211> LENGTH: 43
<212> TYPE: DNA
<213> ORGANISM: Citrobacter freundii

<400> SEQUENCE: 92
tcattactgc tgtggagcgt acgctttaat gataagattc gtg 43

<210> SEQ ID NO 93
<211> LENGTH: 43
<212> TYPE: DNA
<213> ORGANISM: Citrobacter sp.

<400> SEQUENCE: 93
tcattactgc tgtggagcgt acgctttaat ggtaatattt atg 43

<210> SEQ ID NO 94
<211> LENGTH: 43
<212> TYPE: DNA
<213> ORGANISM: Citrobacter freundii

<400> SEQUENCE: 94
tcattactgc tgtggtgcga acgcattaat ggtaagattt gtg 43

<210> SEQ ID NO 95
<211> LENGTH: 43
<212> TYPE: DNA
<213> ORGANISM: Citrobacter koseri

<400> SEQUENCE: 95
tcattactgc tgtagagcgt acgctttaat ggtaagattt gtg 43

<210> SEQ ID NO 96
<211> LENGTH: 43
<212> TYPE: DNA
<213> ORGANISM: Citrobacter sp.

<400> SEQUENCE: 96
tcattactgc tgtagagcgt acgctttaat ggtaatattt gtg 43

<210> SEQ ID NO 97
<211> LENGTH: 43
<212> TYPE: DNA
<213> ORGANISM: Citrobacter youngae

<400> SEQUENCE: 97
tcattactgc tgtggagcgt acgctttaat ggtaatattt gtg 43

<210> SEQ ID NO 98
<211> LENGTH: 43
<212> TYPE: DNA
<213> ORGANISM: Escherichia fergusonii

<400> SEQUENCE: 98
tcattactgc tgtggaatac gggctttaat gataagattt gtt 43

<210> SEQ ID NO 99
<211> LENGTH: 65
<212> TYPE: DNA
<213> ORGANISM: Bacillus pumilus

<400> SEQUENCE: 99
aaatatggac ctgtcaaact tttggacatg ccgaaaaatt gcatgaaata gaggagcgtt 60
attat 65

<210> SEQ ID NO 100
<211> LENGTH: 69
<212> TYPE: DNA
<213> ORGANISM: Bacillus subtilis

<400> SEQUENCE: 100
atacatgggc tagtaaatta tttatacatg cctgcacatc aggcatgtga agatagagga 60
gcgttataa 69

<210> SEQ ID NO 101
<211> LENGTH: 57
<212> TYPE: DNA
<213> ORGANISM: Bacillus glycinifermentans

<400> SEQUENCE: 101
gaaaattact gtttgcctgg ctaataaaca aggaaattta cagaggagcg ttattct 57

<210> SEQ ID NO 102
<211> LENGTH: 39
<212> TYPE: DNA
<213> ORGANISM: Corynebacterium glutamicum

<400> SEQUENCE: 102
atcatctttc cgtatcgcta tttataagga cgactactc 39

<210> SEQ ID NO 103
<211> LENGTH: 52
<212> TYPE: DNA
<213> ORGANISM: Citrobacter freundii

<400> SEQUENCE: 103
aatggttttg catttgtaac cccaaacgca gggtatatca ggtggcaata ac 52

<210> SEQ ID NO 104
<211> LENGTH: 46
<212> TYPE: DNA
<213> ORGANISM: Salmonella enterica

<400> SEQUENCE: 104
gttttgattc cgtaagccca tgaagggcat atcaggtggc aatgac 46

<210> SEQ ID NO 105
<211> LENGTH: 29
<212> TYPE: DNA
<213> ORGANISM: Escherichia albertii

<400> SEQUENCE: 105
acgttgaata cgatcgggat ggcaataac 29

<210> SEQ ID NO 106
<211> LENGTH: 37
<212> TYPE: DNA
<213> ORGANISM: Staphylococcus saprophyticus

<400> SEQUENCE: 106
gtaagcgaag agttaaaaag ctaaaggagc gaacaga 37

<210> SEQ ID NO 107
<211> LENGTH: 40
<212> TYPE: DNA
<213> ORGANISM: Staphylococcus epidermidis

<400> SEQUENCE: 107
gtaagccaaa cagtttttag ttaaaggagc gacgcgtgca 40

<210> SEQ ID NO 108
<211> LENGTH: 50
<212> TYPE: DNA
<213> ORGANISM: Bacillus megaterium

<400> SEQUENCE: 108
gatagttgat ggataaactt gttcacttaa atcaaagggg gaaatgtaat 50

<210> SEQ ID NO 109
<211> LENGTH: 50
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 109
atcaagcaaa gggcaaggtg tcctagtaag gtcgacaagg aggtctaatt 50

<210> SEQ ID NO 110
<211> LENGTH: 75
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 110
agttactagt agcggccgct gcagtccggc aaaaaagggc aaggtgtcct agtaaggtcg 60
acaggaggac tctct 75

<210> SEQ ID NO 111
<211> LENGTH: 48
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 111
gtggaattgt gagcggataa caattcccaa ttaaaggagg aaggatca 48

<210> SEQ ID NO 112
<211> LENGTH: 42
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 112
aattgtgagc ggataacaat taagcttaag gaggtgtatc ta 42

<210> SEQ ID NO 113
<211> LENGTH: 25
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 113
actagagaaa ggtggtgaat actag 25

<210> SEQ ID NO 114
<211> LENGTH: 47
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 114
aatttgaaaa ttatgtatta tgtgaataaa gaggaggaga gtgagat 47

<210> SEQ ID NO 115
<211> LENGTH: 23
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 115
aaaattagct agggggaata att 23

<210> SEQ ID NO 116
<211> LENGTH: 45
<212> TYPE: DNA
<213> ORGANISM: Artificial Sequence
<220> FEATURE:
<223> OTHER INFORMATION: Artificial 5'UTR including a RBS/Shine Dalgarno sequence

<400> SEQUENCE: 116
aacggcattg ctagacggtt acaagaagga ggacgaataa ttata 45

<210> SEQ ID NO 117
<211> LENGTH: 44
<212> TYPE: DNA
<213> ORGANISM: Artificial Sequence
<220> FEATURE:
<223> OTHER INFORMATION: Consensus sequence for SecA promoter from Bacillus
<220> FEATURE:
<221> NAME/KEY: unsure
<222> LOCATION: (2)..(2)
<223> OTHER INFORMATION: All occurrences of k indicate one of the following nucleotides: G, T
<220> FEATURE:
<221> NAME/KEY: unsure
<222> LOCATION: (3)..(3)
<223> OTHER INFORMATION: All occurrences of n indicate one of the following nucleotides: A, C, G, T
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: unsure
<222> LOCATION: (13)..(24)
<223> OTHER INFORMATION: All occurrences of n indicate one of the following nucleotides: A, C, G, T; this sequence segment can be from 8 to 12 nucleotides long
<220> FEATURE:
<221> NAME/KEY: misc_feature
<222> LOCATION: (13)..(24)
<223> OTHER INFORMATION: n is a, c, g, or t
<220> FEATURE:
<221> NAME/KEY: unsure
<222> LOCATION: (25)..(25)
<223> OTHER INFORMATION: All occurrences of r indicate one of the following nucleotides: A, G
<220> FEATURE:
<221> NAME/KEY: unsure
<222> LOCATION: (27)..(27)
<223> OTHER INFORMATION: All occurrences of r indicate one of the following nucleotides: A, G
<220> FEATURE:
<221> NAME/KEY: unsure
<222> LOCATION: (30)..(30)
<223> OTHER INFORMATION: All occurrences of n indicate one of the following nucleotides: A, C, G, T
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: unsure
<222> LOCATION: (33)..(33)
<223> OTHER INFORMATION: All occurrences of w indicate one of the following nucleotides: A, T
<220> FEATURE:
<221> NAME/KEY: unsure
<222> LOCATION: (34)..(34)
<223> OTHER INFORMATION: All occurrences of r indicate one of the following nucleotides: A, G
<220> FEATURE:
<221> NAME/KEY: unsure
<222> LOCATION: (38)..(38)
<223> OTHER INFORMATION: All occurrences of w indicate one of the following nucleotides: A, T
<220> FEATURE:
<221> NAME/KEY: unsure
<222> LOCATION: (39)..(44)
<223> OTHER INFORMATION: All occurrences of n indicate one of the following nucleotides: A, C, G, T; this sequence segment can be from 4 to 6 nucleotides long

```
<220> FEATURE:
<221> NAME/KEY: misc_feature
<222> LOCATION: (39)..(44)
<223> OTHER INFORMATION: n is a, c, g, or t

<400> SEQUENCE: 117

tkntttggaa atnnnnnnnn nnnnrtrtgn tawratawnn nnnn                    44


<210> SEQ ID NO 118
<211> LENGTH: 48
<212> TYPE: DNA
<213> ORGANISM: Artificial Sequence
<220> FEATURE:
<223> OTHER INFORMATION: Consensus sequence for SecA promoter from
      Enterobacter
<220> FEATURE:
<221> NAME/KEY: unsure
<222> LOCATION: (4)..(4)
<223> OTHER INFORMATION: All occurrences of w indicate one of the
      following nucleotides: A, T
<220> FEATURE:
<221> NAME/KEY: unsure
<222> LOCATION: (6)..(6)
<223> OTHER INFORMATION: All occurrences of m indicate one of the
      following nucleotides: A, C
<220> FEATURE:
<221> NAME/KEY: unsure
<222> LOCATION: (7)..(7)
<223> OTHER INFORMATION: All occurrences of n indicate one of the
      following nucleotides: A, C, G, T
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: unsure
<222> LOCATION: (13)..(13)
<223> OTHER INFORMATION: All occurrences of y indicate one of the
      following nucleotides: C, T
<220> FEATURE:
<221> NAME/KEY: unsure
<222> LOCATION: (14)..(26)
<223> OTHER INFORMATION: All occurrences of n indicate one of the
      following nucleotides: A, C, G, T; this sequence segment can be
      from 11 to 13 nucleotides long
<220> FEATURE:
<221> NAME/KEY: misc_feature
<222> LOCATION: (14)..(26)
<223> OTHER INFORMATION: n is a, c, g, or t
<220> FEATURE:
<221> NAME/KEY: unsure
<222> LOCATION: (33)..(33)
<223> OTHER INFORMATION: All occurrences of r indicate one of the
      following nucleotides: A, G
<220> FEATURE:
<221> NAME/KEY: unsure
<222> LOCATION: (37)..(37)
<223> OTHER INFORMATION: All occurrences of d indicate one of the
      following nucleotides: A, G, T
<220> FEATURE:
<221> NAME/KEY: unsure
<222> LOCATION: (41)..(41)
<223> OTHER INFORMATION: All occurrences of y indicate one of the
      following nucleotides: C, T
<220> FEATURE:
<221> NAME/KEY: unsure
<222> LOCATION: (42)..(42)
<223> OTHER INFORMATION: All occurrences of d indicate one of the
      following nucleotides: A, G, T
<220> FEATURE:
<221> NAME/KEY: unsure
<222> LOCATION: (44)..(48)
<223> OTHER INFORMATION: All occurrences of n indicate one of the
      following nucleotides: A, C, G, T; this sequence segment can be
      from 4 to 5 nucleotides long
```

```
<220> FEATURE:
<221> NAME/KEY: misc_feature
<222> LOCATION: (44)..(48)
<223> OTHER INFORMATION: n is a, c, g, or t

<400> SEQUENCE: 118

tcawtmntgc tgynnnnnnn nnnnnnttaa tgrtaadatt ydtnnnnn            48
```

METHOD OF TRANSFORMING BACTERIAL CELLS

This application is a National Stage application of International Application No. PCT/EP2018/068846, filed Jul. 11, 2018, which claims priority to European Patent Application No. 17182610.0, filed Jul. 21, 2017.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "161253_Seqlisting.txt", which was created on Dec. 10, 2019 and is 147,254 bytes in size. The subject matter of the Sequence Listing is incorporated herein in its entirety by reference.

FIELD OF THE INVENTION

The present invention relates to methods of expressing methyltransferases and the use of methyltransferases for producing methylated DNA. Moreover, the present invention relates to increasing the efficiency of introducing DNA into bacterial host cells.

BACKGROUND OF THE INVENTION

The efficiency of introducing of DNA into a bacterial host cells is often the limiting step for the genetic manipulation of the bacterial host or the introduction of DNA that allows for the production of proteins, e.g., enzymes, peptides, and low and high molecular weight chemical compounds, e.g., antibiotics, sugars, poly-gamma-glutamate. Besides various optimized DNA transformation methods and technologies for many different bacterial host cells, such as protoplast transformation, electroporation, chemical transformation, natural and induced competency, DNA uptake and transfer into the bacterial host is limited by the host cell specific restriction-modification-system (RMS) that recognizes non- or differentially methylated DNA as foreign leading to restriction and degradation of the DNA within the bacterial host cell. The host cell's own DNA is protected from the activity of the restrictase (RE) by the cognate DNA-methyltransferase (MTase) with the same DNA binding specificity methylating potential RE target sites in the host genome and thus protects them from cleavage (Blow, M. J. et al. (2016). The Epigenomic Landscape of Prokaryotes. PLoS. Genet. 12, e1005854). The REBASE database comprises a comprehensive database of information about the components of bacterial restriction-modification (RM) systems (Roberts, R. J., Vincze, T., Posfai, J., and Macelis, D. (2015). REBASE—a database for DNA restriction and modification: enzymes, genes and genomes. Nucleic Acids Res. 43, D298-D299).

Heat inactivation of the RM-systems prior to DNA transformation to increase transformation efficiency has been successfully shown for gram-positive bacterial hosts *Bacillus megaterium* (Richhardt, J., Larsen, M., and Meinhardt, F. (2010). An improved transconjugation protocol for *Bacillus megaterium* facilitating a direct genetic knockout. Appl. Microbiol. Biotechnol. 86, 1959-1965) and *Corynebacterium glutamicum* (Schafer, A., Kalinowski, J., Simon, R., Seep-Feldhaus, A. H., and Puhler, A. (1990). High-frequency conjugal plasmid transfer from gram-negative *Escherichia coli* to various gram-positive coryneform bacteria. J. Bacteriol. 172, 1663-1666).

Patent DE4005025 and references therein describe the use of a bacterial host whole cell extract for in vitro methylation of the target DNA for subsequent transfer into the bacterial host, e.g., *Bacillus licheniformis* and *Bacillus amyloliquefaciens.*

The identification of the bacterial host RMS in general is well described in the U.S. Pat. No. 6,689,573 and more specifically in patent EP20895163 for *Bacillus* lichenformis and by De Feyter et al for *Xantomonas campestris* (De Feyter, R. and Gabriel, D. W. (1991). Use of cloned DNA methylase genes to increase the frequency of transfer of foreign genes into *Xanthomonas campestris* pv. *malvacearum*. J. Bacteriol. 173, 6421-6427). Moreover, the methods for expression of the target bacterial host MTase in a bacterial cloning host such as *E. coli* are described in EP618295 and in EP2089516 for in vivo methylation of DNA which is protected from degradation by the RE in the target bacterial host after transfer into the target bacterial host. EP2089516 also describes that the recombinant expressed and purified target host MTase can well be applied for in vitro methylation of DNA.

Lubys et al. ((1995) Gene 157: 25-29) and Madsen et al. ((1995) Applied and Environmental Microbiology, 64(7): 2424-2431) describe DNA sequences encoding for DNA methyltransferases with GCNGC as recognition sequence (NCBI accession numbers X81638, positions 1112-2056 and Y12707, positions 1392-2342, respectively) with sequence identity greater than 74% to SEQ ID NO: 3 disclosed in EP2089516 (sequence identity here determined according to EP2089516 by using the NEEDLE program with the output "longest identity").

Surprisingly it was found by the present inventors that using a methyltransferase that produces the same methylation modification in the same DNA-sequence context of the target bacterial cells that comprises certain structural characteristics shows improved transformation efficiency compared to using the endogenous methyltransferase.

BRIEF SUMMARY OF THE INVENTION

The present invention is directed to a method of producing a DNA methyltransferase, comprising the steps of (a) providing a recombinant host cell comprising a heterologous polynucleotide encoding a DNA methyltransferase wherein the DNA methyltransferase methylates DNA resulting in a DNA containing 5-methylcytosine within the recognition sequence GCNGC, wherein the DNA methyltransferase comprises less than 35 amino acid residues between amino acid residue 72 and amino acid residue 106 according to the numbering of SEQ ID NO: 33;
(b) cultivating the recombinant host cell of step (a) under conditions conductive for the production of the DNA methyltransferase; and
(c) optionally, recovering the DNA methyltransferase.

The present invention is also directed to a method of producing bacterial transformants, comprising:

(a) introducing into a first bacterial host cell a polynucleotide comprising a polynucleotide sequence encoding a DNA methyltransferase comprising a methylation recognition sequence GCNGC to produce a methylated DNA containing 5-methylcytosine within the recognition sequence GCNGC, wherein the DNA methyltransferase comprises less than 35 amino acid residues between amino acid residue 72 and amino acid residue 106 according to the numbering of SEQ ID NO: 33;

(b) transferring the methylated DNA from the first bacterial host cell into a second bacterial host cell, wherein the second bacterial host cell comprises a restriction endonuclease able to degrade the DNA but unable to degrade the methylated DNA; and (c) isolating transformants of the second bacterial host cell comprising the methylated DNA.

Furthermore, the present invention is directed to a method of producing bacterial transformants, comprising the steps of (a) methylating in vitro a DNA with a DNA methyltransferase comprising a methylation recognition sequence GCNGC to produce a methylated DNA containing 5-methylcytosine within the recognition sequence GCNGC, wherein the DNA methyltransferase comprises less than 35 amino acid residues between amino acid residue 72 and amino acid residue 106 according to the numbering of SEQ ID NO: 33;

(b) introducing the methylated DNA into a bacterial host cell, wherein the bacterial host cell comprises a restriction endonuclease able to degrade the DNA but unable to degrade the methylated DNA; and (c) isolating transformants of the bacterial host cell comprising the methylated DNA.

As with the method of the present invention improved transformation efficiencies were observed, the present invention is also directed to the use of a methylated DNA obtained by the method of the present invention for improving the transformation efficiency of the DNA in a bacterial host cell.

DETAILED DESCRIPTION OF THE INVENTION

Figure 1:
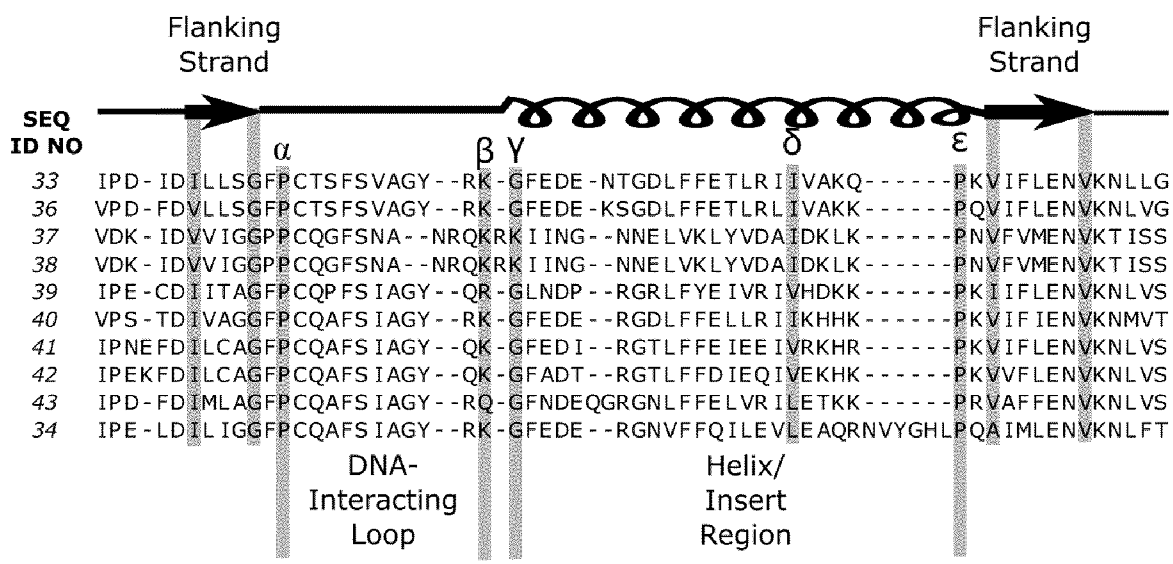
FIG. 1 shows relevant sections from a structure-based multiple sequence alignment of predicted structures of the methyltransferases disclosed herein, which can be created using standard homology modelling programs such as the SWISS-MODEL webserver (Biasini M., Bienert S., Waterhouse A., Arnold K., Studer G., Schmidt T., Kiefer F., Cassarino T. G., Bertoni M., Bordoli L., Schwede T. (2014). SWISS-MODEL: modelling protein tertiary and quaternary structure using evolutionary information Nucleic Acids Research 2014 (1 Jul. 2014) 42 (W1): W252-W258) using default parameters and the following structural templates from the RCSB PDB database (Berman H. M., Westbrook J., Feng Z., Gilliland G., Bhat T. N., Weissig H., Shindyalov I. N., Bourne P. E. (2000) The Protein Data Bank Nucleic Acids Research, 28: 235-242): 2uyc_A (used for SEQ ID NO: 33 (M.Fnu4HI), SEQ ID NO: 34 (M.RBH3250), SEQ ID NO: 41 (M.CocII)), 2i9k_C (used for SEQ ID NO: 36 (M.Bsp6I), SEQ ID NO: 43 (M.LlaDII)), 3swr_A (used for SEQ ID NO: 37 (M.Cdi13307II), SEQ ID NO: 38 (M.Cdi630IV)), 1mht_C (used for SEQ ID NO: 39 (M.Ckr177III)), 2z6u_A (used for SEQ ID NO: 40 (M.CmaLM2II)) and 9mht_C (used for SEQ ID NO: 42 (M.Fsp4HI)). Predicted structures were structurally aligned to the predicted structure of SEQ ID NO: 33 (M.Fnu4HI) with TMalign, version 20160521 (Y. Zhang, J. Skolnick (2005), TM-align: A protein structure alignment algorithm based on TM-score, Nucleic Acids Research, 33: 2302-2309) using the default parameters. Pairwise structural alignments were combined into a multiple sequence alignment using MAFFT, version 7.221 (Katoh, S. (2013) MAFFT multiple sequence alignment software version 7: improvements in performance and usability. Molecular Biology and Evolution 30:772-780) using default parameters of the merge mode. Secondary structure annotation was added to the figure as a consensus of structural predictions. Important conserved positions are highlighted as grey columns and identified by greek letters.

The present invention may be understood more readily by reference to the following detailed description of the embodiments of the invention and the examples included herein.

Definitions

Unless otherwise noted, the terms used herein are to be understood according to conventional usage by those of ordinary skill in the relevant art.

It is to be understood that as used in the specification and in the claims, "a" or "an" can mean one or more, depending upon the context in which it is used. Thus, reference to "a cell" can mean that at least one cell can be utilized.

Throughout this application, various publications are referenced. The disclosures of all of these publications and those references cited within those publications in their entireties are hereby incorporated by reference into this application in order to more fully describe the state of the art to which this invention pertains.

"Parent" sequence (e.g., "parent enzyme" or "parent protein") is the starting sequences for introduction of changes (e.g. by introducing one or more amino acid substitutions) of the sequence resulting in "variants" of the parent sequences. Thus, the term "enzyme variant" or "sequence variant" or "protein variant" are used in reference to parent enzymes that are the origin for the respective variant enzymes. Therefore, parent enzymes include wild type enzymes and variants of wild-type enzymes which are used for development of further variants. Variant enzymes differ from parent enzymes in their amino acid sequence to a certain extent; however, variants at least maintain the enzyme properties of the respective parent enzyme. In one embodiment, enzyme properties are improved in variant enzymes when compared to the respective parent enzyme. In one embodiment, variant enzymes have at least the same enzymatic activity when compared to the respective parent enzyme or variant enzymes have increased enzymatic activity when compared to the respective parent enzyme.

In describing the protein variants, the abbreviations for single amino acids used according to the accepted IUPAC single letter or three letter amino acid abbreviation is used.

"Substitutions" are described by providing the original amino acid followed by the number of the position within the amino acid sequence, followed by the substituted amino acid. For example, the substitution of histidine at position 120 with alanine is designated as "His120Ala" or "H120A".

"Deletions" are described by providing the original amino acid followed by the number of the position within the amino acid sequence, followed by *. Accordingly, the deletion of glycine at position 150 is designated as "Gly150*" or G150*". Alternatively, deletions are indicated by e.g. "deletion of D183 and G184".

"Insertions" are described by providing the original amino acid followed by the number of the position within the amino acid sequence, followed by the original amino acid and the additional amino acid. For example, an insertion at position 180 of lysine next to glycine is designated as "Gly180GlyLys" or "G180GK". When more than one amino acid residue is inserted, such as e.g. a Lys and Ala after Gly180 this may be indicated as: Gly180GlyLysAla or G195GKA.

In cases where a substitution and an insertion occur at the same position, this may be indicated as S99SD+S99A or in short S99AD. In cases where an amino acid residue identical to the existing amino acid residue is inserted, it is clear that degeneracy in the nomenclature arises. If for example a glycine is inserted after the glycine in the above example this would be indicated by G180GG. Variants comprising multiple alterations are separated by "+", e.g., "Arg170Tyr+Gly195Glu" or "R170Y+G195E" representing a substitution of arginine and glycine at positions 170 and 195 with tyrosine and glutamic acid, respectively. Alternatively, multiple alterations may be separated by space or a comma e.g. R170Y G195E or R170Y, G195E respectively. Where different alterations can be introduced at a position, the different alterations are separated by a comma, e.g. "Arg170Tyr, Glu" and R170T, E, respectively, represents a substitution of arginine at position 170 with tyrosine or glutamic acid. Alternatively, different alterations or optional substitutions may be indicated in brackets, e.g., Arg170[Tyr, Gly] or Arg170{Tyr, Gly} or in short R170 [Y, G] or R170 {Y, G}.

The numbering of the amino acid residues of the DNA methyltransferase described herein is according to the numbering of the Fnu4HI DNA methyltransferase from *Fusobacterium nucleatum* 4H as shown in SEQ ID NO: 33 (i.e., according to the numbering of SEQ ID NO: 33).

Variants of the parent enzyme molecules may have an amino acid sequence which is at least n percent identical to the amino acid sequence of the respective parent enzyme having enzymatic activity with n being an integer between 50 and 100, preferably 50, 55, 60, 65, 70, 75, 80, 85, 90, 91, 92, 93, 94, 95, 96, 97, 98 or 99 compared to the full length polypeptide sequence. Variant enzymes described herein which are n percent identical when compared to a parent enzyme, have enzymatic activity.

Enzyme variants may be defined by their sequence identity when compared to a parent enzyme. Sequence identity usually is provided as "% sequence identity" or "% identity". To determine the percent-identity between two amino acid sequences in a first step a pairwise sequence alignment is generated between those two sequences, wherein the two sequences are aligned over their complete length (i.e., a pairwise global alignment). The alignment is generated with a program implementing the Needleman and Wunsch algorithm (J. Mol. Biol. (1979) 48, p. 443-453), preferably by using the program "NEEDLE" (The European Molecular Biology Open Software Suite (EMBOSS)) with the programs default parameters (gapopen=10.0, gapextend=0.5 and matrix=EBLOSUM62). The preferred alignment for the purpose of this invention is that alignment, from which the highest sequence identity can be determined.

After aligning the two sequences, in a second step, an identity value shall be determined from the alignment. Therefore, according to the present invention the following calculation of percent-identity applies:

%-identity=(identical residues/length of the alignment region which is showing the respective sequence of this invention over its complete length)*100. Thus sequence identity in relation to comparison of two amino acid sequences according to this embodiment is calculated by dividing the number of identical residues by the length of the alignment region which is showing the respective sequence of this invention over its complete length. This value is multiplied with 100 to give "%-identity".

For calculating the percent identity of two DNA sequences the same applies as for the calculation of percent identity of two amino acid sequences with some specifications. For DNA sequences encoding for a protein the pairwise alignment shall be made over the complete length of the coding region from start to stop codon excluding introns. For non-protein-coding DNA sequences the pairwise alignment shall be made over the complete length of the sequence of this invention, so the complete sequence of this invention is compared to another sequence, or regions out of another sequence. Moreover, the preferred alignment program implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNA-FULL).

The following example is meant to illustrate the embodiments of the invention, which is on two nucleotide sequences, but same calculations apply to protein sequences:

Seq A: AAGATACTG length: 9 bases

Seq B: GATCTGA length: 7 bases

Hence, the shorter sequence is sequence B.

Producing a pairwise global alignment which is showing both sequences over their complete lengths results in

```
Seq A: AAGATACTG-
         ||| |||
Seq B: --GAT-CTGA
```

The "|" symbol in the alignment indicates identical residues (which means bases for DNA or amino acids for proteins). The number of identical residues is 6.

The "-" symbol in the alignment indicates gaps. The number of gaps introduced by alignment within the Seq B is 1. The number of gaps introduced by alignment at borders of Seq B is 2, and at borders of Seq A is 1.

The alignment length showing the aligned sequences over their complete length is 10.

Producing a pairwise alignment which is showing the shorter sequence over its complete length according to the invention consequently results in:

```
Seq A: GATACTG-
       ||| |||
Seq B: GAT-CTGA
```

Producing a pairwise alignment which is showing sequence A over its complete length according to the invention consequently results in:

```
Seq A: AAGATACTG
         ||| |||
Seq B: --GAT-CTG
```

Producing a pairwise alignment which is showing sequence B over its complete length according to the invention consequently results in:

```
Seq A: GATACTG-
       ||| |||
Seq B: GAT-CTGA
```

The alignment length showing the shorter sequence over its complete length is 8 (one gap is present which is factored in the alignment length of the shorter sequence).

Accordingly, the alignment length showing Seq A over its complete length would be 9 (meaning Seq A is the sequence of the invention).

Accordingly, the alignment length showing Seq B over its complete length would be 8 (meaning Seq B is the sequence of the invention).

According to the example provided above, %-identity is: for Seq A being the sequence of the invention (6/9)*100=66.7%; for Seq B being the sequence of the invention (6/8)*100=75%.

Enzyme variants may be defined by their sequence similarity when compared to a parent enzyme. Sequence similarity usually is provided as "% sequence similarity" or "%-similarity". For calculating sequence similarity in a first step a sequence alignment has to be generated as described above. In a second step, the percent-similarity has to be calculated, whereas percent sequence similarity takes into account that defined sets of amino acids share similar properties, e.g., by their size, by their hydrophobicity, by their charge, or by other characteristics. Herein, the exchange of one amino acid with a similar amino acid is referred to as "conservative mutation". Enzyme variants comprising conservative mutations appear to have a minimal effect on protein folding resulting in certain enzyme properties being substantially maintained when compared to the enzyme properties of the parent enzyme.

For determination of %-similarity according to this invention the following applies, which is also in accordance with the BLOSUM62 matrix, which is one of the most used amino acids similarity matrix for database searching and sequence alignments Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W.

Conservative amino acid substitutions may occur over the full length of the sequence of a polypeptide sequence of a functional protein such as an enzyme. In one embodiment, such mutations are not pertaining the functional domains of an enzyme. In another embodiment conservative mutations are not pertaining the catalytic centers of an enzyme.

Therefore, according to the present invention the following calculation of percent-similarity applies:

%-similarity=[(identical residues+similar residues)/length of the alignment region which is showing the respective sequence of this invention over its complete length]*100. Thus sequence similarity in relation to comparison of two amino acid sequences herein is calculated by dividing the number of identical residues plus the number of similar residues by the length of the alignment region which is showing the respective sequence of this invention over its complete length. This value is multiplied with 100 to give "%-similarity".

Especially, variant enzymes comprising conservative mutations which are at least m percent similar to the respective parent sequences with m being an integer between 50 and 100, preferably 50, 55, 60, 65, 70, 75, 80, 85, 90, 91, 92, 93, 94, 95, 96, 97, 98 or 99 compared to the full length polypeptide sequence, are expected to have essentially unchanged enzyme properties. Variant enzymes described herein with m percent-similarity when compared to a parent enzyme, have enzymatic activity.

The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, sepharose beads or any other resin. The hybridisation process can furthermore occur with one of the complementary nucleic acids immobilised to a solid support such as a nitro-cellulose or nylon membrane or immobilised by e.g. photolithography to a carrier, including, but not limited to a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

This formation or melting of hybrids is dependent on various parameters, including but not limited thereto the temperature. An increase in temperature favours melting, while a decrease in temperature favours hybridisation. However, this hybrid forming process is not following an applied change in temperature in a linear fashion: the hybridisation process is dynamic, and already formed nucleotide pairs are supporting the pairing of adjacent nucleotides as well. So, with good approximation, hybridisation is a yes-or-no process, and there is a temperature, which basically defines the border between hybridisation and no hybridisation. This temperature is the melting temperature (Tm). Tm is the temperature in degrees Celsius, at which 50% of all molecules of a given nucleotide sequence are hybridised into a double strand, and 50% are present as single strands.

The melting temperature (Tm) is dependent from the physical properties of the analysed nucleic acid sequence and hence can indicate the relationship between two distinct sequences. However, the melting temperature (Tm) is also influenced by various other parameters, which are not directly related with the sequences, and the applied conditions of the hybridization experiment must be taken into account. For example, an increase of salts (e.g. monovalent cations) is resulting in a higher Tm.

Tm for a given hybridisation condition can be determined by doing a physical hybridisation experiment, but Tm can also be estimated in silico for a given pair of DNA sequences. In this embodiment, the equation of Meinkoth and Wahl (Anal. Biochem., 138:267-284, 1984) is used for stretches having a length of 50 or more bases: Tm=81.5° C.+16.6 (log M)+0.41 (% GC)−0.61 (% form)−500/L.

M is the molarity of monovalent cations, % GC is the percentage of guanosine and cytosine nucleotides in the DNA stretch, % form is the percentage of formamide in the hybridisation solution, and L is the length of the hybrid in base pairs. The equation is for salt ranges of 0.01 to 0.4 M and % GC in ranges of 30% to 75%.

While above Tm is the temperature for a perfectly matched probe, Tm is reduced by about 1° C. for each 1% of mismatching (Bonner et al., J. Mol. Biol. 81: 123-135, 1973): Tm=[81.5° C.+16.6 (log M)+0.41 (% GC)−0.61 (% formamide)−500/L]−% non-identity.

This equation is useful for probes having 35 or more nucleotides and is widely referenced in scientific method literature (e.g. in: "Recombinant DNA Principles and Methodologies", James Greene, Chapter "Biochemistry of Nucleic acids", Paul S. Miller, page 55; 1998, CRC Press), in many patent applications (e.g. in: U.S. Pat. No. 7,026,149), and also in data sheets of commercial companies (e.g. "Equations for Calculating Tm" from www.genomics.agilent.com).

Other formulas for Tm calculations, which are less preferred in this embodiment, might be only used for the indicated cases:

For DNA-RNA hybrids (Casey, J. and Davidson, N. (1977) Nucleic Acids Res., 4:1539): Tm=79.8° C.+18.5 (log M)+0.58 (% GC)+11.8 (% GC*% GC)−0.5 (% form)−820/L.

For RNA-RNA hybrids (Bodkin, D. K. and Knudson, D. L. (1985) J. Virol. Methods, 10: 45): Tm=79.8° C.+18.5 (log M)+0.58 (% GC)+11.8 (% GC*% GC)−0.35 (% form)−820/L.

For oligonucleotide probes of less than 20 bases (Wallace, R. B., et al. (1979) Nucleic Acid Res. 6: 3535): Tm=2×n (A+T)+4×n(G+C), with n being the number of respective bases in the probe forming a hybrid.

For oligonucleotide probes of 20-35 nucleotides, a modified Wallace calculation could be be applied: Tm=22+1.46 n(A+T)+2.92 n(G+C), with n being the number of respective bases in the probe forming a hybrid.

For other oligonucleotides, the nearest-neighbour model for melting temperature calculation should be used, together with appropriate thermodynamic data:

$$Tm=(\Sigma(\Delta Hd)+\Delta Hi)/(\Sigma(\Delta Sd)+\Delta Si+\Delta S\text{self}+R\times\ln(cT/b))+16.6\log[Na+]-273.15$$

(Breslauer, K. J., Frank, R., Blöcker, H., Marky, L. A. 1986 Predicting DNA duplex stability from the base sequence. Proc. Natl Acad. Sci. USA 833746-3750; Alejandro Panjkovich, Francisco Melo, 2005. Comparison of different melting temperature calculation methods for short DNA sequences. Bioinformatics, 21 (6): 711-722)

where:

Tm is the melting temperature in degrees Celsius;

Σ(ΔHd) and τ(ΔSd) are sums of enthalpy and entropy (correspondingly), calculated over all internal nearest-neighbor doublets;

ΔSself is the entropic penalty for self-complementary sequences;

ΔHi and ΔSi are the sums of initiation enthalpies and entropies, respectively;

R is the gas constant (fixed at 1.987 cal/K·mol);

cT is the total strand concentration in molar units;

constant b adopts the value of 4 for non-self-complementary sequences or equal to 1 for duplexes of self-complementary strands or for duplexes when one of the strands is in significant excess.

The thermodynamic calculations assume that the annealing occurs in a buffered solution at pH near 7.0 and that a two-state transition occurs.

Thermodynamic values for the calculation can be obtained from Table 1 in (Alejandro Panjkovich, Francisco Melo, 2005. Comparison of different melting temperature calculation methods for short DNA sequences. Bioinformatics, 21 (6): 711-722), or from the original research papers (Breslauer, K. J., Frank, R., Blöcker, H., Marky, L. A. 1986 Predicting DNA duplex stability from the base sequence. Proc. Natl Acad. Sci. USA 833746-3750; SantaLucia, J., Jr, Allawi, H. T., Seneviratne, P. A. 1996 Improved nearest-neighbor parameters for predicting DNA duplex stability. Biochemistry 353555-3562; Sugimoto, N., Nakano, S., Yoneyama, M., Honda, K. 1996 Improved thermodynamic parameters and helix initiation factor to predict stability of DNA duplexes. Nucleic Acids Res. 244501-4505).

For an in silico estimation of Tm according to this embodiment, first a set of bioinformatic sequence alignments between the two sequences are generated. Such alignments can be generated by various tools known to a person skilled in the art, like programs "Blast" (NCBI), "Water" (EMBOSS) or "Matcher" (EMBOSS), which are producing local alignments, or "Needle" (EMBOSS), which is producing global alignments. Those tools should be applied with their default parameter setting, but also with some parameter variations. For example, program "MATCHER" can be applied with various parameter for gapopen/gapextend (like 14/4; 14/2; 14/5; 14/8; 14/10; 20/2; 20/5; 20/8; 20/10; 30/2; 30/5; 30/8; 30/10; 40/2; 40/5; 40/8; 40/10; 10/2; 10/5; 10/8; 10/10; 8/2; 8/5; 8/8; 8/10; 6/2; 6/5; 6/8; 6/10) and program "WATER" can be applied with various parameter for gapopen/gapextend (like 10/0,5; 10/1; 10/2; 10/3; 10/4; 10/6; 15/1; 15/2; 15/3; 15/4; 15/6; 20/1; 20/2; 20/3; 20/4; 20/6; 30/1; 30/2; 30/3; 30/4; 30/6; 45/1; 45/2; 45/3; 45/4; 45/6; 60/1; 60/2; 60/3; 60/4; 60/6), and also these programs shall be applied by using both nucleotide sequences as given, but also with one of the sequences in its reverse complement form. For example, BlastN (NCBI) can be applied with an increased e-value cut-off (e.g. e+1 or even e+10) to also identify very short alignments, especially in data bases of small sizes.

Important is that local alignments are considered, since hybridisation may not necessarily occur over the complete length of the two sequences, but may be best at distinct regions, which then are determining the actual melting temperature. Therefore, from all created alignments, the alignment length, the alignment % GC content (in a more accurate manner, the % GC content of the bases which are matching within the alignment), and the alignment identity has to be determined. Then the predicted melting temperature (Tm) for each alignment has to be calculated. The highest calculated Tm is used to predict the actual melting temperature.

The term "hybridisation over the complete sequence of the invention" as defined herein means that for sequences longer than 300 bases when the sequence of the invention is fragmented into pieces of about 300 to 500 bases length, every fragment must hybridise. For example, a DNA can be fragmented into pieces by using one or a combination of restriction enzymes. A bioinformatic in silico calculation of Tm is then performed by the same procedure as described above, just done for every fragment. The physical hybridisation of individual fragments can be analysed by standard Southern analysis, or comparable methods, which are known to a person skilled in the art.

The term "stringency" as defined herein is describing the ease by which hybrid formation between two nucleotide sequences can take place. Conditions of a "higher stringency" require more bases of one sequence to be paired with the other sequence (the melting temperature Tm is lowered in conditions of "higher stringency"), conditions of "lower stringency" allow some more bases to be unpaired. Hence the degree of relationship between two sequences can be estimated by the actual stringency conditions at which they are still able to form hybrids. An increase in stringency can be achieved by keeping the experimental hybridisation temperature constant and lowering the salts concentrations, or by keeping the salts constant and increasing the experimental hybridisation temperature, or a combination of these parameter. Also an increase of formamide will increase the stringency. The skilled artisan is aware of additional parameters which may be altered during hybridisation and which will either maintain or change the stringency conditions (Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

A typical hybridisation experiment is done by an initial hybridisation step, which is followed by one to several washing steps. The solutions used for these steps may contain additional components, which are preventing the degradation of the analyzed sequences and/or prevent unspecific background binding of the probe, like EDTA, SDS, fragmented sperm DNA or similar reagents, which are known to a person skilled in the art (Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

A typical probe for a hybridisation experiment is generated by the random-primed-labelling method, which was initially developed by Feinberg and Vogelstein (Anal. Biochem., 132 (1), 6-13 (1983); Anal. Biochem., 137 (1), 266-7 (1984) and is based on the hybridisation of a mixture of all possible hexanucleotides to the DNA to be labelled. The labelled probe product will actually be a collection of fragments of variable length, typically ranging in sizes of 100-1000 nucleotides in length, with the highest fragment concentration typically around 200 to 400 bp. The actual size range of the probe fragments, which are finally used as probes for the hybridisation experiment, can also be influenced by the used labelling method parameter, subsequent purification of the generated probe (e.g. agarose gel), and the size of the used template DNA which is used for labelling (large templates can e.g. be restriction digested using a 4 bp cutter, e.g. HaeIII, prior labeling).

For the present invention, the sequence described herein is analysed by a hybridisation experiment, in which the probe is generated from the other sequence, and this probe is generated by a standard random-primed-labelling method. For the present invention, the probe is consisting of a set of labelled oligonucleotides having sizes of about 200-400 nucleotides. A hybridisation between the sequence of this invention and the other sequence means, that hybridisation of the probe occurs over the complete sequence of this invention, as defined above. The hybridisation experiment is done by achieving the highest stringency by the stringency of the final wash step. The final wash step has stringency conditions comparable to the stringency conditions of at least Wash condition 1: 1.06×SSC, 0.1% SDS, 0 formamide at 50° C., in another embodiment of at least Wash condition 2: 1.06×SSC, 0.1 SDS, 0% formamide at 55° C., in another embodiment of at least Wash condition 3: 1.06×SSC, 0.1% SDS, 0% formamide at 60° C., in another embodiment of at least Wash condition 4: 1.06×SSC, 0.1% SDS, 0% formamide at 65° C., in another embodiment of at least Wash condition 5: 0.52×SSC, 0.1% SDS, 0% formamide at 65° C., in another embodiment of at least Wash condition 6: 0.25×SSC, 0.1% SDS, 0% formamide at 65° C., in another embodiment of at least Wash condition 7: 0.12×SSC, 0.1% SDS, 0% formamide at 65° C., in another embodiment of at least Wash condition 8: 0.07×SSC, 0.1% SDS, 0% formamide at 65° C.

A "low stringent wash" has stringency conditions comparable to the stringency conditions of at least Wash condition 1, but not more stringent than Wash condition 3, wherein the wash conditions are as described above.

A "high stringent wash" has stringency conditions comparable to the stringency conditions of at least Wash condition 4, in another embodiment of at least Wash condition 5, in another embodiment of at least Wash condition 6, in another embodiment of at least Wash condition 7, in another embodiment of at least Wash condition 8, wherein the wash conditions are as described above.

The term "heterologous" (or exogenous or foreign or recombinant or non-native) polypeptide is defined herein as a polypeptide that is not native to the host cell, a polypeptide native to the host cell in which structural modifications, e.g., deletions, substitutions, and/or insertions, have been made by recombinant DNA techniques to alter the native polypeptide, or a polypeptide native to the host cell whose expression is quantitatively altered or whose expression is directed from a genomic location different from the native host cell as a result of manipulation of the DNA of the host cell by recombinant DNA techniques, e.g., a stronger promoter. Similarly, the term "heterologous" (or exogenous or foreign or recombinant or non-native) polynucleotide refers to a polynucleotide that is not native to the host cell, a polynucleotide native to the host cell in which structural modifications, e.g., deletions, substitutions, and/or insertions, have been made by recombinant DNA techniques to alter the native polynucleotide, or a polynucleotide native to the host cell whose expression is quantitatively altered as a result of manipulation of the regulatory elements of the polynucleotide by recombinant DNA techniques, e.g., a stronger promoter, or a polynucleotide native to the host cell, but integrated not within its natural genetic environment as a result of genetic manipulation by recombinant DNA techniques.

With respect to two or more polynucleotide sequences or two or more amino acid sequences, the term "heterologous" is used to characterized that the two or more polynucleotide sequences or two or more amino acid sequences are naturally not occurring in the specific combination with each other.

For the purposes of the invention, "recombinant" (or transgenic) with regard to a cell or an organism means that the cell or organism contains a heterologous polynucleotide which is introduced by man by gene technology and with regard to a polynucleotide includes all those constructions brought about by man by gene technology/recombinant DNA techniques in which either (a) the sequence of the polynucleotide or a part thereof, or (b) one or more genetic control sequences which are operably linked with the polynucleotide, including but not limited thereto a promoter, or (c) both a) and b)

are not located in their wildtype genetic environment or have been modified.

The term "native" (or wildtype or endogenous) cell or organism and "native" (or wildtype or endogenous) polynucleotide or polypeptide refers to the cell or organism as found in nature and to the polynucleotide or polypeptide in question as found in a cell in its natural form and genetic environment, respectively (i.e., without there being any human intervention).

A "DNA with methylation pattern foreign to a cell" refers to a DNA comprising a methylation pattern not naturally occurring in the cell and thus can be recognized and cleaved by one or more restriction enzymes of the cell.

The terms "polynucleotide", "nucleic acid sequence", "nucleotide sequence", "nucleic acid", "nucleic acid molecule" are used interchangeably herein and refer to nucleotides, either ribonucleotides or deoxyribonucleotides or a combination of both, in a polymeric unbranched form of any length. "Polynucleotides" are composed of monomers, which are "nucleotides" made of three components: a pentose sugar, a phosphate group, and a nitrogenous base.

The term "nucleic acid construct" as used herein refers to a nucleic acid molecule, either single- or double-stranded, which is isolated from a naturally occurring gene or is modified to contain segments of nucleic acids in a manner that would not otherwise exist in nature or is synthetic. The term "nucleic acid construct" is synonymous with the term "expression cassette" when the nucleic acid construct contains the control sequences required for expression of a polynucleotide.

The term "control sequence" is defined herein to include all sequences affecting the expression of a polynucleotide, including but not limited thereto, the expression of a polynucleotide encoding a polypeptide. Each control sequence may be native or foreign to the polynucleotide or native or foreign to each other. Such control sequences include, but are not limited to, promoter sequence, 5'-UTR (also called leader sequence), ribosomal binding site (RBS, shine dalgarno sequence), 3'-UTR, and transcription start and stop sites.

The term "functional linkage" or "operably linked" with respect to regulatory elements, is to be understood as meaning the sequential arrangement of a regulatory element (including but not limited thereto a promoter) with a nucleic acid sequence to be expressed and, if appropriate, further regulatory elements (including but not limited thereto a terminator) in such a way that each of the regulatory elements can fulfil its intended function to allow, modify, facilitate or otherwise influence expression of said nucleic acid sequence. For example, a control sequence is placed at an appropriate position relative to the coding sequence of the polynucleotide sequence such that the control sequence directs the expression of the coding sequence of a polypeptide. Preferred arrangements are those in which the nucleic acid sequence to be expressed recombinantly is positioned behind the sequence acting as promoter, so that the two sequences are linked covalently to each other. In one embodiment, the nucleic acid sequence to be transcribed is located behind the promoter in such a way that the transcription start is identical with the desired beginning of the RNA. Functional linkage, and an expression construct, can be generated by means of customary recombination and cloning techniques as described (e.g., Sambrook, J. and Russell, D. W. Molecular cloning. A laboratory manual, 3rd ed, Cold Spring Harbor Laboratory Press, Cold Spring Harbor, NY. 2001); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands; Plant Molecular Biology Labfax (1993) by R. D. D. Croy, published by BIOS Scientific Publications Ltd (UK) and Blackwell Scientific Publications (UK)). However, further sequences, including but not limited thereto a sequence, which acts as a linker with specific cleavage sites for restriction enzymes, or as a signal peptide, may also be positioned between the two sequences. The insertion of sequences may also lead to the expression of fusion proteins.

A "promoter" or "promoter sequence" is a nucleotide sequence located upstream of a gene on the same strand as the gene that enables that gene's transcription. Promoter is followed by the transcription start site of the gene. Promoter is recognized by RNA polymerase (together with any required transcription factors), which initiates transcription. A functional fragment or functional variant of a promoter is a nucleotide sequence which is recognizable by RNA polymerase, and capable of initiating transcription.

The term "promoter sequence comprising a consensus sequence and wherein the consensus sequence is immediately followed by a transcription start site" or the term "promoter sequence comprising a consensus sequence immediately followed by a transcription start site" are meant herein as the transcription start site being directly adjacent to the consensus sequence, i.e., without any linking additional nucleotides between consensus sequence and transcription start site.

The term "transcription start site" or "transcriptional start site" shall be understood as the location where the transcription starts at the 5' end of a gene sequence. In prokaryotes the first nucleotide, referred to as +1 is in general an adenosine (A) or guanosine (G) nucleotide. In this context, the terms "sites" and "signal" can be used interchangeably herein.

When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG, CTG or TTG and ends with a stop codon such as TAA, TAG, or TGA. The coding sequence may be a DNA, cDNA, synthetic, or recombinant nucleotide sequence. The start codon can also be named herein as "translational start signal" or "translational start site". The stop codon can also be named herein as "translational stop signal" or "translational stop site".

The term "expression" or "gene expression" means the transcription of a specific gene or specific genes or specific nucleic acid construct. The term "expression" or "gene expression" in particular means the transcription of a gene or genes or genetic construct into structural RNA (e.g., rRNA, tRNA) or mRNA with or without subsequent translation of the latter into a protein. The process includes transcription of DNA and processing of the resulting mRNA product.

The term "expression vector" is defined herein as a linear or circular DNA molecule that comprises a polynucleotide that is operably linked to one or more control sequences that provides for the expression of the polynucleotide.

The term "moderate expression" of a gene is defined herein as an expression level of a given gene that does not impair cellular growth or viability and allows continuous cultivation of the host cell.

The term "host cell", as used herein, includes any cell type that is susceptible to transformation, transfection, transduction, conjugation, and the like with a nucleic acid construct or expression vector.

The term "introduction" and variations thereof are defined herein as the transfer of a DNA into a host cell. The introduction of a DNA into a host cell can be accomplished by any method known in the art, including, the not limited to, transformation, transfection, transduction, conjugation, and the like.

The term "donor cell" is defined herein as a cell that is the source of DNA introduced by any means to another cell.

The term "recipient cell" is defined herein as a cell into which DNA is introduced.

The term "fermentation in industrial scale" (also called large-scale fermentation) refers to fermentation processes with fermenter volumes of greater than or equal to 20 liters.

The term "DNA methyltransferase that methylates DNA resulting in a DNA containing 5-methylcytosine within the recognition sequence GCNGC" is defined herein as a DNA (cytosine-5)-methyltransferase (EC 2.1.1.37) that catalyzes the transfer of a methyl group from S-adenosyl-L-methionine to cytosine within the sequence GCNGC, resulting in S-adenosyl-L-homocysteine and DNA containing 5-methylcytosine. For purposes of the present invention, DNA methyltransferase activity is determined according to the procedure described by Pfeifer et al., 1983, Biochim. Biophys. Acta 740: 323-30. One unit of DNA methyltransferase activity is the amount required to protect 1 μg of lambda DNA in 1 hour in a total reaction volume of 20 μl against cleavage by the corresponding restriction endonuclease.

The term "restriction-modification system" is defined herein as a restriction endonuclease, a corresponding DNA methyltransferase that protects DNA from cleavage by the restriction endonuclease, and the genes encoding at least these two enzymes.

The term "operon" is understood herein as a unit of genomic DNA, containing a single promoter, and one or more genes, all of which are transcribed from that single promoter. The genes in the operon may overlap, or may have untranslated regions (UTRs) between each other. These UTRs may optionally have additional control elements, affecting translational efficiency. Without being limited thereto, an example of a secA-containing operon is a construct consisting of a promoter, a 5'UTR, a secM gene (secretion monitor, SecA regulator SecM), a UTR, and secA gene.

The SecA protein is a multi-functional protein involved in the process of protein secretion (protein translocation) across the bacterial inner cell membrane (Green, Erin R., and Joan Mecsas. "Bacterial Secretion Systems—An Overview." Microbiology spectrum 4.1 (2016)). The secA gene, coding the SecA protein, is usually annotated as "translocase subunit SecA", "preprotein translocase subunit SecA", "protein translocase subunit SecA", "translocase binding subunit (ATPase)", or "preprotein translocase; secretion protein". Some organisms have two SecA protein homologs, one of which is essential and the other one is not (Braunstein M, Brown A M, Kurtz S, Jacobs W R Jr. "Two nonredundant SecA homologues function in mycobacteria." Journal of Bacteriology, 1 Dec. 2001, 183(24):6979-6990; Feltcher M E, Braunstein M. "Emerging themes in SecA2-mediated protein export." Nature Reviews Microbiology, 24 Sep. 2012, 10(11):779-789). In organisms, which have two SecA-like translocase proteins, the annotation of the protein translocase subunit SecA gene pertinent to this patent application is usually marked by an additional index 1, e.g. "protein translocase subunit SecA1", and denotes the essential translocase.

DETAILED DESCRIPTION

DNA Methyltransferases

FIG. 1 shows a structure-based multiple sequence alignment of the amino acid sequences of various DNA methyltransferases comprising these structural features. It can be derived from FIG. 1 that between amino acid residue 72 and amino acid residue 106 according to the numbering of SEQ ID NO: 33 there are 33 amino acids in SEQ ID NOs: 33, 36, 37, and 38, there are 32 amino acids in SEQ ID NOs: 39-42 and there are 34 amino acids in SEQ ID NO: 43. However, there are 38 amino acids between amino acid residue 72 and amino acid residue 106 according to the numbering of SEQ ID NO: 33 in SEQ ID NO: 34. Thus, compared to SEQ ID NO: 34 there is a deletion in SEQ ID NO: 33 and SEQ ID NO: 36-43.

Hence, the DNA methyltransferase described herein and used in the methods of the present invention methylates DNA within the recognition sequence GCNGC resulting in DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33.

In one embodiment, the DNA methyltransferase described herein and used in the methods of the present invention methylates DNA within the recognition sequence GCNGC resulting in DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33, wherein the DNA methyltransferase comprises at least 22, preferably at least 28 amino acid residues between amino acid residue 72 and amino acid residue 106 according to the numbering of SEQ ID NO: 33. Hence, preferably, the DNA methyltransferase comprises between amino acid residue 72 and amino acid residue 106 according to the numbering of SEQ ID NO: 33 22-34, preferably 28-34, more preferably 22-33, even more preferably 28-33, most preferably 30-34 or 30-33 amino acid residues. Most preferred, there are 33 amino acids residues between amino acid residue 72 and amino acid residue 106 according to the numbering of SEQ ID NO: 33.

In another embodiment, the DNA methyltransferase used in these methods of the present comprises less than 23 amino acid residues between amino acid residue 84 and amino acid residue 106 according to the numbering of SEQ ID NO: 33.

In another embodiment, the DNA methyltransferase comprises less than 23 amino acid residues between amino acid residue 84 and amino acid residue 106 according to the numbering of SEQ ID NO: 33, wherein the DNA methyltransferase comprises at least 12, preferably at least 18 amino acid residues between amino acid residue 84 and amino acid residue 106 according to the numbering of SEQ ID NO: 33. Hence, preferably, the DNA methyltransferase comprises between amino acid residue 84 and amino acid residue 106 according to the numbering of SEQ ID NO: 33 12-22, preferably 18-22, more preferably 12-21, even more preferably 18-21 amino acid residues.

In another embodiment the DNA methyltransferase used in the methods of the present invention methylates DNA within the recognition sequence GCNGC resulting in DNA containing 5-methylcytosine within the recognition sequence GCNGC and comprises less than 5 amino acid residues between amino acid residue 101 and amino acid residue 106 according to the numbering of SEQ ID NO: 33.

In preferred embodiment the DNA methyltransferase described herein and used in the methods of the present invention methylates DNA within the recognition sequence GCNGC resulting in DNA containing 5-methylcytosine within the recognition sequence GCNGC and comprises less than 5 amino acid residues between amino acid residue 101 and amino acid residue 106 according to the numbering of SEQ ID NO: 33, wherein the DNA methyltransferase comprises 0-4, preferably 2-4, more preferably 3-4, 0, 1, 2, 3, 4, preferably 4, amino acid residues between amino acid residue 101 and amino acid residue 106 according to the numbering of SEQ ID NO: 33.

In another embodiment, the DNA methyltransferase comprises less than 11 amino acid residues between amino acid residue 72 and amino acid residue 83 according to the numbering of SEQ ID NO: 33.

In another embodiment, the DNA methyltransferase comprises less than 11 amino acid residues between amino acid residue 72 and amino acid residue 83 according to the numbering of SEQ ID NO: 33, wherein the DNA methyltransferase comprises at least 7, preferably at least 8 amino acid residues between amino acid residue 72 and amino acid residue 83 according to the numbering of SEQ ID NO: 33. Hence, preferably, the DNA methyltransferase comprises between amino acid residue 72 and amino acid residue 83 according to the numbering of SEQ ID NO: 33 7-10, preferably 8-10, more preferably 9-10 amino acid residues.

In another embodiment the DNA methyltransferase used in the methods of the present invention methylates DNA within the recognition sequence GCNGC resulting in DNA containing 5-methylcytosine within the recognition sequence GCNGC and comprises less than 35 amino acid residues between amino acid residue 72 and amino acid residue 106 according to the numbering of SEQ ID NO: 33 and further comprises less than 23 amino acid residues between amino acid residue 84 and amino acid residue 106 according to the numbering of SEQ ID NO: 33.

In another embodiment the DNA methyltransferase used in the methods of the present invention methylates DNA within the recognition sequence GCNGC resulting in DNA containing 5-methylcytosine within the recognition sequence GCNGC and comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33.

In another embodiment, the DNA methyltransferase further comprises less than 11 amino acid residues between amino acid residue 72 and amino acid residue 83 according to the numbering of SEQ ID NO: 33.

In a preferred embodiment the DNA methyltransferase described herein and used in the methods of the present invention methylates DNA within the recognition sequence GCNGC resulting in DNA containing 5-methylcytosine within the recognition sequence GCNGC and comprises less than 5 amino acid residues between amino acid residue 101 and amino acid residue 106 according to the numbering of SEQ ID NO: 33. Preferably, the DNA methyltransferase described herein and used in the methods of the present invention comprises 0-4, preferably 2-4, more preferably 3-4 amino acid residues between amino acid residue 101 and amino acid residue 106 according to the numbering of SEQ ID NO: 33. Preferably, the DNA methyltransferase described herein and used in the methods of the present invention comprises 0, 1, 2, 3, or 4, preferably 4 amino acid residues between amino acid residue 101 and amino acid residue 106 according to the numbering of SEQ ID NO: 33.

As shown in FIG. 1, the DNA methyltransferase described herein and used in the methods of the present invention comprises in one embodiment the following structural features with respect to the indicated amino acid positions corresponding to SEQ ID NO: 33.

| Identifier | | | α | β | γ | δ | ε | | |
|---|---|---|---|---|---|---|---|---|---|
| Position in SEQ ID NO: 33 | I66 | G70 | P72 | K83 | G84 | I101 | P106 | V108 | V114 |
| Comment | start of sheet | end of sheet | start of DNA-interacting loop | end of DNA-interacting loop | beginning of helix | beginning of insert region | end of helix/ end of insert region | start of sheet | end of sheet |

Thus, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 comprises between amino acid residue 72 and amino acid residue 106 according to the numbering of SEQ ID NO: 33 a DNA interacting loop region and an alpha helix region. Preferably, the DNA interacting loop region is between amino acid residue 72 and amino acid residue 83 according to the numbering of SEQ ID NO: 33 and the alpha helix region is between residue 84 and 106 according to the numbering of SEQ ID NO: 33.

In one embodiment, the DNA methyltransferase described herein and used in the methods of the present invention that methylates DNA resulting in a DNA containing 5-methylcytosine within the recognition sequence GCNGC comprises at least 70%, at least 80%, at least 90%, or at least 95% sequence identity to SEQ ID NO: 34 and comprises a deletion between amino acid residue 72 and amino acid residue 106 according to the numbering of SEQ ID NO: 33 so that there are less than 35 amino acid residues between amino acid residue 72 and amino acid residue 106 according to the numbering of SEQ ID NO: 33. In one embodiment, the deletion is in the alpha helix region between amino acid residue 84 and 106 according to the numbering of SEQ ID NO: 33. Preferably, there is a deletion between amino acid residue 72 and amino acid residue 106 according to the numbering of SEQ ID NO: 33 of 1-20 amino acids, preferably 3-12, more preferably 4-8. Preferably, the deletion in the helix region between amino acid residue 84 and 106 according to the numbering of SEQ ID NO: 33 is a deletion of 1-15, preferably 2-10, more preferably 4-8 amino acid residues. In another embodiment, the deletion is in the DNA interacting loop region between amino acid residue 72 and 83 according to the numbering of SEQ ID NO: 33. Preferably, the deletion in the DNA interacting loop region between amino acid residue 72 and 83 according to the numbering of SEQ ID NO: 33 is a deletion of 1-6, preferably 2-4, most preferably 1-2 amino acid residues. In one embodiment, the deletion is in the alpha helix region between amino acid residue 84 and 106 according to the numbering of SEQ ID NO: 33 and in the DNA interacting loop region between amino acid residue 72 and 83 according to the numbering of SEQ ID NO: 33. Preferably, the deletion is in the alpha helix region between amino acid residue 84 and 106 according to the numbering of SEQ ID NO: 33 and in the DNA interacting loop region between amino acid residue 72 and 83 according to the numbering of SEQ ID NO: 33 is a deletion of 1-20, preferably 2-12, more preferably 4-10, most preferably 4-8 amino acid residues. Preferably, the deletion between amino acid residue 72 and amino acid residue 106 according to the numbering of SEQ ID NO: 33 does not abolish the function of the DNA interacting loop region between amino acid residue 72 and 83 according to the numbering of SEQ ID NO: 33 and does not completely remove the alpha helix region between amino acid residue 84 and 106 according to the numbering of SEQ ID NO: 33.

The DNA methyltransferase variant of SEQ ID NO: 34 comprises a DNA interacting loop region and an alpha helix region between amino acid residue 72 and amino acid residue 106 according to the numbering of SEQ ID NO: 33.

The DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is in one embodiment selected from the group consisting of:

(a) a DNA methyltransferase having at least 55% identity with SEQ ID NO: 33, 36, or 43;
(b) a DNA methyltransferase encoded by a polynucleotide having at least 70% identity with SEQ ID NO: 19, 25, or 27;
(c) a DNA methyltransferase encoded by a polynucleotide that hybridizes under high stringency conditions with (i) a polynucleotide comprising SEQ ID NO: 19, 25, or 27, or (ii) the full-length complement of (i);
(d) a variant of the DNA methyltransferase of SEQ ID NO: 33, 36, or 43 comprising a substitution, in one embodiment a conservative substitution, deletion, and/or insertion at one or more positions and having DNA methyltransferase activity;
(e) a DNA methyltransferase encoded by a polynucleotide that differs from SEQ ID NO: 19, 25, or 27 due to the degeneracy of the genetic code; and
(f) a fragment of the DNA methyltransferase of (a), (b), (c), (d) or (e) that has DNA methyltransferase activity.

In one embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 selected from the group consisting of:

(a) a DNA methyltransferase having at least 55% identity with SEQ ID NO: 33;
(b) a DNA methyltransferase encoded by a polynucleotide having at least 70% identity with SEQ ID NO: 19;
(c) a DNA methyltransferase encoded by a polynucleotide that hybridizes under high stringency conditions with (i) a polynucleotide comprising SEQ ID NO: 19, or (ii) the full-length complement of (i);
(d) a variant of the DNA methyltransferase of SEQ ID NO: 33 comprising a substitution, in one embodiment a conservative substitution, deletion, and/or insertion at one or more positions and having DNA methyltransferase activity;
(e) a DNA methyltransferase encoded by a polynucleotide that differs from SEQ ID NO: 19 due to the degeneracy of the genetic code; and
(f) a fragment of the DNA methyltransferase of (a), (b), (c), (d) or (e) that has DNA methyltransferase activity.

In one embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is selected from the group consisting of:

(a) a DNA methyltransferase having at least 90% identity with SEQ ID NO: 33, 35, 36, 37, 38, 39, 40, 41, 42, or 43;
(b) a DNA methyltransferase encoded by a polynucleotide having at least 80% identity with SEQ ID NO: 18, 19, 20, 21, 24, 25, 26, 27, 28, 29, 30, 31, or 32;
(c) a DNA methyltransferase encoded by a polynucleotide that hybridizes under high stringency conditions with (i) a polynucleotide comprising SEQ ID NO: 18, 19, 20, 21, 24, 25, 26, 27, 28, 29, 30, 31, or 32, or (ii) the full-length complement of (i);
(d) a variant of the DNA methyltransferase of SEQ ID NO: 33, 35, 36, 37, 38, 39, 40, 41, 42, or 43 comprising a substitution, deletion, and/or insertion at one or more positions and having DNA methyltransferase activity;
(e) a DNA methyltransferase encoded by a polynucleotide that differs from SEQ ID NO: 18, 19, 20, 21, 24, 25, 26, 27, 28, 29, 30, 31, or 32 due to the degeneracy of the genetic code; and
(f) a fragment of the DNA methyltransferase of (a), (b), (c), (d) or (e) that has DNA methyltransferase activity.

In one embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is selected from the group consisting of:

(a) a DNA methyltransferase having at least 80%, at least 90%, at least 95%, at least 98%, or 100% identity with SEQ ID NO: 33; and
(b) a DNA methyltransferase encoded by a polynucleotide having at least 90%, at least 95%, at least 98%, or 100% identity with SEQ ID NO: 18.

In a preferred embodiment, the DNA methyltransferase described herein and used in the methods of the present invention that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is selected from the group consisting of:

(a) a DNA methyltransferase having at least 80%, at least 90%, at least 95%, at least 98%, or 100% identity with SEQ ID NO: 33; and
(b) a DNA methyltransferase encoded by a polynucleotide having at least 90%, at least 95%, at least 98%, or 100% identity with SEQ ID NO: 18;

wherein the DNA methyltransferase comprise between amino acid residue 72 and amino acid residue 106 according to the numbering of SEQ ID NO: 33 a DNA interacting loop region and an alpha helix region. Preferably, the DNA interacting loop region is between amino acid residue 72 and amino acid residue 83 according to the numbering of SEQ ID NO: 33 and the alpha helix region is between residue 84 and 106 according to the numbering of SEQ ID NO: 33.

In one embodiment, the DNA methyltransferase described herein and used in the methods of the present invention that methylates DNA resulting in a DNA containing 5-methylcytosine within the recognition sequence GCNGC and comprises less than 23 amino acid residues between amino acid residue 84 and amino acid residue 106 according to the numbering of SEQ ID NO: 33 is selected from the group consisting of:

(a) a DNA methyltransferase having at least 90%, at least 95%, at least 98%, or 100% identity with SEQ ID NO: 33; and
(b) a DNA methyltransferase encoded by a polynucleotide having at least 90%, at least 95%, at least 98%, or 100% identity with SEQ ID NO: 18.

In a further preferred embodiment, the DNA methyltransferase described herein and used in the methods of the present invention that methylates DNA resulting in a DNA containing 5-methylcytosine within the recognition sequence GCNGC and comprises less than 23 amino acid residues between amino acid residue 84 and amino acid residue 106 according to the numbering of SEQ ID NO: 33 is selected from the group consisting of:

(a) a DNA methyltransferase having at least 90%, at least 95%, at least 98% identity, or 100% with SEQ ID NO: 33; and
(b) a DNA methyltransferase encoded by a polynucleotide having at least 90%, at least 95%, at least 98%, or 100% identity with SEQ ID NO: 18;

wherein the DNA methyltransferase comprise between amino acid residue 84 and amino acid residue 106 according to the numbering of SEQ ID NO: 33 an alpha helix region.

In a most preferred embodiment, the DNA methyltransferase described herein and used in the methods of the present invention that methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33 is selected from the group consisting of:

(a) a DNA methyltransferase having at least 90%, at least 95%, at least 98%, or 100% identity with SEQ ID NO: 33; and
(b) a DNA methyltransferase encoded by a polynucleotide having at least 90%, at least 95%, at least 98%, or 100% identity with SEQ ID NO: 18.

In one embodiment, the DNA methyltransferase described herein and used in the methods of the present invention that methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33 is selected from the group consisting of:

(a) a DNA methyltransferase having at least 90%, at least 95%, at least 98% identity, or 100% with SEQ ID NO: 33; and
(b) a DNA methyltransferase encoded by a polynucleotide having at least 90%, at least 95%, at least 98%, or 100% identity with SEQ ID NO: 18;

wherein the DNA methyltransferase comprise between amino acid residue 72 and amino acid residue 106 according to the numbering of SEQ ID NO: 33 a DNA interacting loop region and an alpha helix region. Preferably, the DNA interacting loop region is between amino acid residue 72 and amino acid residue 83 according to the numbering of SEQ ID NO: 33 and the alpha helix region is between residue 84 and 106 according to the numbering of SEQ ID NO: 33.

In one embodiment, the variant of the DNA methyltransferase of SEQ ID NO: 33, 35, 36, 37, 38, 39, 40, 41, 42, or 43 comprising a substitution at one or more positions and having DNA methyltransferase activity comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 substitutions. In another embodiment, the variant of the DNA methyltransferase of SEQ ID NO: 33, 35, 36, 37, 38, 39, 40, 41, 42, or 43 comprising a substitution at one or more positions and having DNA methyltransferase activity comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 conservative substitutions.

In one embodiment, the DNA methyltransferase that methylates DNA within the recognition sequence GCNGC resulting in a DNA containing 5-methylcytosine within the recognition sequence GCNGC and comprises less than 35 amino acid residues between amino acid residue 72 and amino acid residue 106 according to the numbering of SEQ ID NO: 33, comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33 and in another embodiment comprises less than 11 amino acid residues between amino acid residue 72 and amino acid residue 83 according to the numbering of SEQ ID NO: 33 used in the methods of the present invention is selected from the group consisting of:

(a) a DNA methyltransferase having at least 55% identity with SEQ ID NO: 33, 36, or 43;
(b) a DNA methyltransferase encoded by a polynucleotide having at least 70% identity with SEQ ID NO: 19, 25, or 27;

(c) a DNA methyltransferase encoded by a polynucleotide that hybridizes under high stringency conditions with (i) a polynucleotide comprising SEQ ID NO: 19, 25, or 27, or (ii) the full-length complement of (i);

(d) a variant of the DNA methyltransferase of SEQ ID NO: 33, 36, or 43 comprising a substitution, in one embodiment a conservative substitution, deletion, and/or insertion at one or more positions and having DNA methyltransferase activity;

(e) a DNA methyltransferase encoded by a polynucleotide that differs from SEQ ID NO: 19, 25, or 27 due to the degeneracy of the genetic code; and (f) a fragment of the DNA methyltransferase of (a), (b), (c), (d) or (e) that has DNA methyltransferase activity.

The DNA methyltransferase described herein and used in the methods of the present invention is in one embodiment a DNA methyltransferase having at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 33, 35, 36, 37, 38, 39, 40, 41, 42, or 43, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention is a DNA methyltransferase having at least at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 33, 35, 36, or 43, wherein the DNA methyltransferase methylates DNA within the recognition sequence GCNGC resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention is a DNA methyltransferase having at least 80%, at least 85%, at least 90%, at least 91%, at least 92%, at least 93%, at least 94%, at least 95%, at least 96%, at least 97%, at least 98%, at least 99% or even 100% sequence identity to an amino acid sequence displayed in SEQ ID NO: 33, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention methylates DNA resulting in a DNA containing 5-methylcytosine within the recognition sequence GCNGC and further comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33.

In one embodiment, the DNA methyltransferase described herein and used in the methods of the present invention methylates DNA resulting in a DNA containing 5-methylcytosine within the recognition sequence GCNGC and further comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, wherein the DNA methyltransferase comprises 0-4, preferably 2-4, more preferably 3-4, 0, 1, 2, 3, or 4, preferably 4 amino acid residues between amino acid residue 101 and amino acid residue 106 according to the numbering of SEQ ID NO: 33.

In one embodiment, the DNA methyltransferase described herein and used in the methods of the present invention further comprises less than 5 amino acid residues between amino acid residue 101 and amino acid residue 106 according to the numbering of SEQ ID NO: 33 and in another embodiment comprises less than 11 amino acid residues between amino acid residue 72 and amino acid residue 83 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or even 100% sequence identity to an amino acid sequence displayed in SEQ ID NO: 33.

In one embodiment, the DNA methyltransferase described herein and used in the methods of the present invention comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33 and comprises less than 11 amino acid residues between amino acid residue 72 and amino acid residue 83 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33.

In one embodiment, the DNA methyltransferase described herein and used in the methods of the present invention comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33 and comprises less than 11 amino acid residues between amino acid residue 72 and amino acid residue 83 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, wherein the DNA methyltransferase methylates DNA resulting in a DNA containing 5-methylcytosine within the recognition sequence GCNGC.

In another embodiment, the DNA methyltransferase used in the present invention is defined as above, whereas the indicated sequence identity is exchanged to sequence similarity as defined herein.

In another embodiment, the DNA methyltransferase is a variant of the DNA methyltransferase of SEQ ID NO: 33, 35, 36, 37, 38, 39, 40, 41, 42, or 43 comprising a conservative substitution at one or more positions and having DNA methyltransferase activity. In another embodiment, the DNA methyltransferase is a variant of the DNA methyltransferase of SEQ ID NO: 33, 35, 36, 37, 38, 39, 40, 41, 42, or 43 comprising compared to the parent sequence only conservative substitution at one or more positions and having DNA methyltransferase activity.

In another embodiment, the DNA methyltransferase is a fragment of a DNA methyltransferase that has DNA methyltransferase activity. In one embodiment, the DNA methyltransferase is a fragment of SEQ ID NO: 33, 35, 36, 37, 38, 39, 40, 41, 42, or 43, that has DNA methyltransferase activity.

In another embodiment, the fragment of the DNA methyltransferase described herein and used in the method of the present invention has one or more amino acids deleted from the amino and/or carboxyl terminus of SEQ ID NO: 33, 35, 36, 37, 38, 39, 40, 41, 42, or 43, wherein the fragment methylates DNA within the recognition sequence GCNGC resulting in a DNA containing 5-methylcytosine within the recognition sequence GCNGC and comprises less than 35 amino acid residues between amino acid residue 72 and amino acid residue 106 according to the numbering of SEQ ID NO: 33. In another embodiment, the fragment of the DNA methyltransferase described herein and used in the method of the present invention has 1, 2, 3, 4, 5, 6, 7, 8, 9, 10, 11, 12, 13, 14, 15, 16, 17, 18, 19, or 20 amino acids deleted from the amino and/or carboxyl terminus and/or truncations of loop regions in-between. In one embodiment, a fragment of SEQ ID NO: 33, 35, 36, 37, 38, 39, 40, 41, 42, or 43 contains at least 300 amino acid residues.

In another embodiment, the DNA methyltransferase is a fusion protein in which another polypeptide is fused at the N-terminus or the C-terminus of the DNA methyltransferase described herein or fragment thereof. A fusion protein is produced by fusing a nucleotide sequence (or a portion thereof) encoding one polypeptide to a nucleotide sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

In one embodiment, the DNA methyltransferase described herein is from a *Fusobacterium* species, in another embodiment from *Fusobacterium nucleatum* (Barker, H. A., Kahn, J. M., & Hedrick, L. (1982). Pathway of lysine degradation in *Fusobacterium nucleatum*. Journal of Bacteriology, 152 (1), 201-207), in another embodiment from *Fusobacterium nucleatum* 4HI (Vaisvila, R. and Morgan, R. D. (2011) New England Biolabs—Accession number JF323048, *Fusobacterium nucleatum* strain 4H Fnu4HI restriction-modification system gene cluster with M.Fnu4HI (accession number ADX97301)). In one embodiment, the DNA methyltransferase described herein comprises the amino acid sequence as shown in SEQ ID NO: 33. In a further embodiment, the DNA methyltransferase described herein consists of the amino acid sequence as shown in SEQ ID NO: 33.

The DNA methyltransferase described herein and used in the methods of the present invention is in one embodiment encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 18, 19, 20, 21, 24, 25, 26, 27, 28, 29, 30, 31, or 32, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention is encoded by a polynucleotide having at least 70%, at least 75%, at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 19, 24, 25 or 27, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention is encoded by a polynucleotide having at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 19, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In one embodiment, the DNA methyltransferase described herein and used in the methods of the present invention further comprises less than 5 amino acid residues between amino acid residue 101 and amino acid residue 106 according to the numbering of SEQ ID NO: 33 and in one embodiment comprises less than 11 amino acid residues between amino acid residue 72 and amino acid residue 83 according to the numbering of SEQ ID NO: 33 and is encoded by a polynucleotide having at least 80%, at least 85%, at least 90%, at least 91%, at least 92%, at least 93%, at least 94%, at least 95%, at least 96%, at least 97%, at least 98%, at least 99% or even 100% sequence identity with SEQ ID NO: 19.

In another embodiment, the DNA methyltransferase is encoded by a polynucleotide that hybridizes with (i) a polynucleotide comprising SEQ ID NO: 19, 24, 25 or 27, or (ii) the full-length complement of (i). In one embodiment, the DNA methyltransferase is encoded by a polynucleotide that hybridizes under high stringent conditions with (i) a polynucleotide comprising SEQ ID NO: 19, 24, 25 or 27, or (ii) the full-length complement of (i). In another embodiment, the stringency conditions are as described above.

In another embodiment, the DNA methyltransferase is encoded by a polynucleotide that differs from SEQ ID NO: 19, 24, 25 or 27 due to the degeneracy of the genetic code. In one embodiment, the DNA methyltransferase is encoded by a polynucleotide that differs from SEQ ID NO: 19 only due to the degeneracy of the genetic code.

Nucleic Acid Constructs

The DNA methyltransferase described herein and used in the method of the present invention is encoded by a polynucleotide comprised in a nucleic acid construct, in one embodiment an expression construct, suitable to express the polynucleotide encoding the DNA methyltransferase. This expression construct can be extra-chromosomal to the genomic DNA of the host cell or can be integrated in the genomic DNA of the host cell. In another embodiment, the DNA methyltransferase described herein is encoded on an expression vector, in one embodiment a plasmid. In yet another embodiment, the polynucleotide encoding the DNA methyltransferase described herein is integrated in the genomic DNA.

A polynucleotide encoding a DNA methyltransferase can be manipulated in a variety of ways to provide for expression of the polynucleotide in a suitable host cell. Manipulation of the polynucleotide's nucleotide sequence prior to its insertion into a nucleic acid construct or vector may be desirable or necessary depending on the nucleic acid construct or vector or host cell. The techniques for modifying nucleotide sequences utilizing cloning methods are well known in the art.

In one embodiment, the polynucleotide encoding the DNA methyltransferase is operably linked to one or more control sequences that directs the production of the DNA methyltransferase in a host cell.

Each control sequence may be native or foreign to the nucleotide sequence encoding the DNA methyltransferase. Such control sequences include, but are not limited to, a leader, a promoter, a signal sequence, and a transcription terminator. At a minimum for protein expression, the control sequences include a promoter, a transcriptional and a translational start site and a transcriptional and a translational stop signal. The control sequences may be provided with linkers for the purpose of introducing specific restriction sites facilitating ligation of the control sequences with the coding region of the nucleotide sequence.

The control sequence may be an appropriate promoter sequence, a nucleotide sequence that is recognized by a host cell for expression of the nucleotide sequence. The promoter sequence contains transcription control sequences that mediate the expression of the coding sequence of interest. The promoter sequence comprises a nucleotide sequence that is recognized by a bacterial host cell for expression of the polynucleotide encoding a polypeptide. The promoter may be any nucleotide sequence that shows transcriptional activity in the host cell of choice and may be obtained from genes directing synthesis of extracellular or intracellular polypeptides having biological activity either wildtype or heterologous to the host cell. The promoter comprises nucleotide sequences that interact specifically with RNA polymerase of the host cell and allow for initiation of messenger RNA synthesis, i.e., the synthesis of RNA transcript (Browning, D. F. and Busby, S. J. W. (2004). The regulation of bacterial transcription initiation. Nat Rev Micro 2, 57-65). Suitable promoters for directing the transcription of the nucleic acid constructs in a bacterial host cell include but are not limited to the promoters obtained from the *E. coli* lac operon, the *Streptomyces coelicolor* agarose gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Komaroff et al., 1978, Proceedings of the National Academy of Sciences USA 75:3727-3731), as well as the tac promoter (DeBoer et al., 1983, Proceedings of the National Academy of Sciences USA 80:21-25).

In one embodiment, at least one control sequence comprises a promoter sequence of an operon comprising a secA gene (herein also called "secA promoter") or a functional fragment or functional variant thereof and wherein said promoter sequence is heterologous to the polynucleotide. In one embodiment, the promoter sequence of an operon comprising a secA gene or the functional fragment or functional variant thereof confers a moderate expression level.

In a further embodiment, the promoter sequence comprises the consensus sequence TKNTTTGGAAATN(8-12) RTRTGNTAWRATAWN(4-6) (SEQ ID NO: 117) and wherein the consensus sequence is immediately followed by a transcription start site.

In a further embodiment, the promoter sequence comprises the consensus sequence TKNTTTGGAAATNNNNNNNNNRTRTGNTAWRATAWNNNN and wherein the consensus sequence is immediately followed by a transcription start site.

In yet another embodiment, the promoter sequence (a) has at least 70% sequence identity with SEQ ID NO: 9, 53, 54, 55, 56, 57, 58, 59, 60, 61, 62, 63, 64, 65, 66, 67, or 68;

(b) hybridizes under high stringency conditions with (i) a polynucleotide comprising SEQ ID NO: 9, 53, 54, 55, 56, 57, 58, 59, 60, 61, 62, 63, 64, 65, 66, 67, or 68, or (ii) the full-length complement of (i); or (c) is a variant of the promoter sequence of SEQ ID NO: 9, 53, 54, 55, 56, 57, 58, 59, 60, 61, 62, 63, 64, 65, 66, 67, or 68 comprising a substitution, in one embodiment a conservative substitution, deletion, and/or insertion at one or more positions and wherein the variant of the promoter sequence has promoter activity.

In yet another embodiment, the promoter sequence has at least 70% sequence identity with SEQ ID NO: 9, 53, 54, 55, 56, 57, 58, 59, 60, 61, 62, 63, 64, 65, 66, 67, or 68.

In a preferred embodiment, the promoter sequence has at least 70%, at least 75%, at least 80%, at least 85%, at least 90%, at least 92%, at least 95%, at least 98%, at least 99%, or even 100% sequence identity with SEQ ID NO: 9. Preferably, the promoter sequence has at least 90% or at least 95% sequence identity with SEQ ID NO: 9.

In another embodiment, the promoter sequence of an operon comprising a secA gene is from a *Bacillus* species. The *Bacillus* species may be, but is not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus, Bacillus cereus Bacillus paralicheniformis, Bacillus subtilis*, and *Bacillus thuringiensis* cells. In one embodiment, the *Bacillus* species is *Bacillus amyloliquefaciens, Bacillus lentus, Bacillus licheniformis, Bacillus stearothermophilus* or *Bacillus subtilis*. In another embodiment, the *Bacillus* species is *Bacillus licheniformis* or *Bacillus subtilis*. In another embodiment, the *Bacillus* species is *Bacillus licheniformis*. Preferably, the *Bacillus* species is *Bacillus licheniformis.*

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 9, 53, 54, 55, 56, 57, 58, 59, 60, 61, 62, 63, 64, 65, 66, 67, or 68 and wherein the promoter sequence is from a *Bacillus* species.

In a further embodiment, the promoter sequence has at least 70%, at least 75%, at least 80%, at least 85%, at least 90%, at least 92%, at least 95%, at least 98%, at least 99%, or even 100% sequence identity with SEQ ID NO: 9 and wherein the promoter sequence is from a *Bacillus* species, in a specific embodiment from *Bacillus licheniformis.*

In another embodiment, the promoter sequence comprises the consensus sequence TCAWTMNTGCTGYN(11-13)

TTAATGRTAADATTYDTN(4-5) (SEQ ID NO: 118) and wherein the consensus sequence is immediately followed by a transcription start site.

In another embodiment, the promoter sequence comprises the consensus sequence TCAWTMNTGCTGY-NNNNNNNNNNNNTTAATGRTAADATTYDTNNNN and wherein the consensus sequence is immediately followed by a transcription start site.

In yet another embodiment, the promoter sequence (a) has at least 70% sequence identity with SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98;

(b) hybridizes under high stringency conditions with (i) a polynucleotide comprising SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98, or (ii) the full-length complement of (i); or (c) is a variant of the promoter sequence of SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98 comprising a substitution, in one embodiment a conservative substitution, deletion, and/or insertion at one or more positions and wherein the variant of the promoter sequence has promoter activity.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 82.

In a further embodiment, the promoter sequence of an operon comprising a secA gene is from an Enterobacteria species. In another embodiment, the promoter sequence is from an Enterobacteriaceae species. In yet another embodiment, the promoter sequence is from *Escherichia coli.*

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98 and wherein the promoter sequence is from an Enterobacteria species.

In yet another embodiment, the promoter sequence has at least 70%, at least 75%, at least 80%, at least 85%, at least 90%, at least 92%, at least 95%, at least 98%, at least 99%, or even 100% sequence identity with SEQ ID NO: 82 and wherein the promoter sequence is from an Enterobacteria species, in a specific embodiment from *Escherichia coli.*

In one embodiment, the promoter sequence is from an operon comprising a secA gene from a microorganism selected from the group consisting of Bacillaceae, Lactobacillaceae, Enterobacteriaceae, Staphylococcaceae, Corynebacteriaceae, Brevibacteriaceae, Pseudomonadaceae, Streptomycetaceae, Acetobacteraceae, and Clostridiaceae.

In another embodiment, the promoter sequence is from an operon comprising a secA gene from a microorganism selected from the group consisting of *Bacillus licheniformis, Lactobacillus acidophilus, Escherichia coli, Staphylococcus aureus, Corynebacterium glutamicum, Pseudomonas putida, Streptomyces coelicolor, Gluconobacter oxydans*, and *Clostridium acetobutylicum.*

In one embodiment, the promoter sequence is from an operon comprising a secA gene which encodes for a SecA protein having at least 60% sequence identity to the amino acid sequence displayed in SEQ ID NO: 44, 45, 46, 47, 48, 49, 50, 51, or 52.

In one embodiment, the promoter sequence is from an operon comprising a secA gene which encodes for a SecA protein having at least 60%, at least 65%, at least 70%, at least 75%, at least 80%, at least 85%, at least 90%, at least 92%, at least 95%, at least 98%, at least 99%, or even 100% sequence identity with the amino acid sequence displayed in SEQ ID NO: 44, 45, 46, 47, 48, 49, 50, 51, or 52.

In a further one embodiment, the promoter sequence is from an operon comprising a secA gene which encodes for a SecA protein having at least 60%, at least 65%, at least 70%, at least 75%, at least 80%, at least 85%, at least 90%, at least 92%, at least 95%, at least 98%, at least 99%, or even 100% sequence identity with the amino acid sequence displayed in SEQ ID NO: 44.

In a further one embodiment, the promoter sequence is from an operon comprising a secA gene which encodes for a SecA protein having at least 60%, at least 65%, at least 70%, at least 75%, at least 80%, at least 85%, at least 90%, at least 92%, at least 95%, at least 98%, at least 99%, or even 100% sequence identity with the amino acid sequence displayed in SEQ ID NO: 45.

In one embodiment, the nucleic acid construct and/or the expression vector described herein comprises one or more further control sequences. Such control sequences include, but are not limited to promoter sequence, 5'-UTR (also called leader sequence), ribosomal binding site (RBS, shine dalgarno sequence), 3'-UTR, and transcription and translation terminator. In one embodiment, the control sequences may be provided with linkers for the purpose of introducing specific restriction sites facilitating ligation of the control sequences with the polynucleotide to be expressed.

The nucleic acid construct comprises a suitable transcription start and terminator sequence. Any transcription start or terminator that is functional in the host cell of choice may be used in the present invention.

In one embodiment the nucleic acid construct comprises a suitable UTR (untranslated region) sequence. In one embodiment, the nucleic acid construct described herein comprises a 5'UTR and/or a 3'UTR sequence. In one embodiment, the one or more control sequence of the nucleic acid construct comprises a 5'UTR, also referred to as leader sequence. In another one embodiment, the one or more control sequence of the nucleic acid construct comprises a 5'UTR sequence comprising a ribosome-binding site also referred to as a shine-dalgarno sequence. Any leader sequence that is functional in the host cell of choice may be used in the present invention. The UTR can be natural or artificial. In one embodiment, the 5'UTR has at least 90%, at least 92%, at least 95%, at least 98% or even 100% sequence identity to SEQ ID NO: 13 or to any of SEQ ID NO: 99 to 116.

The nucleic acid constructs described herein can be used for expression of a protein of interest. Hence, in one embodiment the polynucleotide of the nucleic acid construct operably linked to one or more control sequence that directs the expression of the polynucleotide in a host cell, wherein at least one control sequence comprises a promoter sequence of an operon comprising a secA gene or a functional fragment or functional variant thereof, is a polynucleotide encoding for a protein of interest. In one embodiment the protein of interest is selected from the group consisting of a methyltransferase, an endonuclease, a serine recombinase, a tyrosine recombinase, and a protein conferring antibiotic resistance.

The nucleic acid construct and/or the expression vector described herein can be used for providing a moderate expression level of a polynucleotide, preferably a polynucleotide encoding a protein of interest, in a host cell.

In one embodiment, the nucleic acid construct and/or the expression vector described herein can be used for expression of a polynucleotide, preferably a polynucleotide encoding a protein of interest in a host cell, providing an expression level of said polynucleotide allowing continuous cultivation of the host cell.

Further promoters are described in "Useful proteins from recombinant bacteria" in Scientific American, 1980, 242: 74-94; and in Sambrook et al. (Sambrook, J. and Russell, D. W. Molecular cloning. A laboratory manual, 3rd ed, Cold Spring Harbor Laboratory Press, Cold Spring Harbor, N Y. 2001).

The control sequence may also be a suitable transcription terminator sequence, a sequence recognized by a host cell to terminate transcription. The terminator sequence is operably linked to the 3' terminus of the nucleotide sequence encoding a DNA methyltransferase. Any terminator that is functional in the host cell of choice may be used in the present invention.

The control sequence may also be a suitable leader sequence, also referred to as UTR, a nontranslated region of a mRNA that is important for translation by the host cell. The leader sequence is operably linked to the 5' terminus of the nucleotide sequence directing synthesis of the polypeptide having biological activity. Any leader sequence that is functional in the host cell of choice may be used in the present invention.

The control sequence may also be a suitable UTR sequence, in one embodiment comprising a shine-dalgarno sequence for directing protein translation in a bacterial host cell.

For autonomous replication, the expression vector may further comprise an origin of replication enabling the vector to replicate autonomously in the host cell in question. Bacterial origins of replication include but are not limited to the origins of replication of plasmids pBR322, pUC19, pSC101, pACYC177, and pACYC184 permitting replication in *E. coli* (Sambrook, J. and Russell, D. W. Molecular cloning. A laboratory manual, 3rd ed, Cold Spring Harbor Laboratory Press, Cold Spring Harbor, N.Y. 2001; Cohen, S. N., Chang, A. C. Y., Boyer, H. W., & Helling, R. B. (1973). Construction of Biologically Functional Bacterial Plasmids In Vitro. Proceedings of the National Academy of Sciences of the United States of America, 70(11), 3240-3244), and pUB110, pC194, pTB19, pAMß1, and pTA1060 permitting replication in *Bacillus* (Janniere, L., Bruand, C., and Ehrlich, S. D. (1990). Structurally stable *Bacillus subtilis* cloning vectors. Gene 87, 53-6; Ehrlich, S. D., Bruand, C., Sozhamannan, S., Dabert, P., Gros, M. F., Janniere, L., and Gruss, A. (1991). Plasmid replication and structural stability in *Bacillus subtilis*. Res. Microbiol. 142, 869-873), and pE194 (Dempsey, L. A. and Dubnau, D. A. (1989). Localization of the replication origin of plasmid pE194. J. Bacteriol. 171, 2866-2869). The origin of replication may be one having a mutation to make its function temperature-sensitive in the host cell (see, e.g., Ehrlich, 1978, Proceedings of the National Academy of Sciences USA 75:1433-1436).

In one embodiment, the vectors contain one or more selectable markers that permit easy selection of transformed cells. A selectable marker is a gene encoding a product, which provides for biocide resistance, resistance to heavy metals, prototrophy to auxotrophs, and the like. Bacterial selectable markers include but are not limited to the dal genes from *Bacillus subtilis* or *Bacillus licheniformis*, or markers that confer antibiotic resistance such as ampicillin, kanamycin, erythromycin, chloramphenicol or tetracycline resistance. Furthermore, selection may be accomplished by co-transformation, e.g., as described in WO91/09129, where the selectable marker is on a separate vector.

The introduction of DNA into a host cell, in one embodiment a *Bacillus* cell, may, for instance, be effected by protoplast transformation (see, e.g., Chang and Cohen, 1979, Molecular General Genetics 168: 111-115), by using competent cells (see, e.g., Young and Spizizen, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278). Specific transformation protocols are known in the art for various types of host cells (see, e.g., for *E. coli* protoplast transformation see Hanahan, 1983, J. Mol. Biol. 166: 557-580).

Host Cells

Various host cells can be used for expressing the DNA methyltransferase described herein. Host cells comprising the genetic constructs described herein can be obtained by one of the methods described herein for introducing the polynucleotides into such host cells.

In one embodiment, the host cell is a prokaryote or a eukaryote. In another embodiment, the host cell is a bacteria, an archaea, a fungal cell, a yeast cell or a eukaryotic cell. In another embodiment, the host cell is a non-human host cell.

In one embodiment, the host cell is a bacterial cell. The bacterial host cell may be any gram-positive bacterium or a gram-negative bacterium. Gram-positive bacteria include, but are not limited to, *Bacillus, Brevibacterium, Corynebacterium, Streptococcus, Streptomyces, Staphylococcus, Enterococcus, Lactobacillus, Lactococcus, Clostridium, Geobacillus*, and *Oceanobacillus*. Gram-negative bacteria include, but are not limited to, *Escherichia, Pseudomonas, Salmonella, Campylobacter, Helicobacter, Acetobacter, Flavobacterium, Fusobacterium, Gluconobacter*. In a specific embodiment, the bacterial host cell is a *Escherichia coli* cell. In one embodiment, the host cell is a bacterial cell. In a specific embodiment the host cell is of the genus *Escherichia* or *Bacillus*.

In the methods of the present invention, the bacterial host cell may be any *Bacillus* cell. *Bacillus* cells useful in the practice of the present invention, include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus methylotrophicus, Bacillus cereus Bacillus paralicheniformis, Bacillus subtilis*, and *Bacillus thuringiensis* cells. In one embodiment, the bacterial host cell is a *Bacillus amyloliquefaciens, Bacillus lentus, Bacillus licheniformis, Bacillus stearothermophilus* or *Bacillus subtilis* cell. In another embodiment, the bacterial host cell is a *Bacillus licheniformis* cell or a *Bacillus subtilis* cell, in a specific embodiment a *Bacillus licheniformis* cell. Preferably, the bacterial host cell is a *Bacillus licheniformis* cell. More preferably, the host cell is a *Bacillus licheniformis* ATCC 53926 cell.

In the methods of the present invention, the bacterial host cell may be *Lactobacillus acidophilus, Lactobacillus plantarum, Lactobacillus gasseri, Lactobacillus bulgaricusk, Lactobacillus reuteri, Escherichia coli, Staphylococcus aureus, Corynebacterium glutamicum, Corynebacterium acetoglu-*

*tamicum, Corynebacterium acetoacidophilum, Corynebacterium callunae, Corynebacterium ammoniagenes, Corynebacterium thermoaminogenes, Corynebacterium melassecola, Corynebacterium effiziens, Corynebacterium efficiens, Corynebacterium deserti, Brevibacterium flavum, Brevibacterium lactofermentum, Brevibacterium divarecatum, Pseudomonas putida, Pseudomonas syringae, Streptomyces coelicolor, Streptomyces lividans, Streptomyces albus, Streptomyces avermitilis, Gluconobacter oxydans, Gluconobacter morbifer, Gluconobacter thailandicus, Acetobacter aceti, Clostridium acetobutylicum, Clostridium saccharobutylicum, Clostridium beijerinckii, Streptococcus equisimilis, Streptococcus pyogenes, Streptococcus uberis, Streptococcus equi* subsp., *Zooepidemicus* or *Basfia succiniciproducens.*

In one embodiment, the host cell does not naturally express a DNA methyltransferase as shown in SEQ ID NO: 33, 35, 36, 37, 38, 39, 40, 41, 42, or 43. Thus, in one embodiment, the DNA methyltransferase described herein is heterologous for the host cell.

In another embodiment, the bacterial host cell may additionally contain modifications, e.g., deletions or disruptions, of other genes that may be detrimental to the production, recovery or application of a polypeptide of interest. In one embodiment, a bacterial host cell is a protease-deficient cell. In another embodiment, the bacterial host cell, e.g., *Bacillus* cell, comprises a disruption or deletion of extracellular protease genes including but not limited to aprE, mpr, vpr, bpr, and/or epr. In one embodiment, the bacterial host cell does not produce spores. In another embodiment, the bacterial host cell, e.g., *Bacillus* cell, comprises a disruption or deletion of spoIIAC, sigE, and/or sigG. In one embodiment, the bacterial host cell, e.g., *Bacillus* cell, comprises a disruption or deletion of one of the genes involved in the biosynthesis of surfactin, e.g., srfA, srfB, srfC, and/or srfD. See, for example, U.S. Pat. No. 5,958,728. In another embodiment, the bacterial host cell comprises a disruption or deletion of one of the genes involved in the biosynthesis of polyglutamic acid. Other genes, including but not limited to the amyE gene, which are detrimental to the production, recovery or application of a polypeptide of interest may also be disrupted or deleted.

Methods of the Invention

In one embodiment, the present invention is directed to a method of producing a DNA methyltransferase, comprising the steps of (a) providing a recombinant host cell comprising a heterologous polynucleotide encoding a DNA methyltransferase wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33, as further described herein, preferably by introducing the polynucleotide into the host cell;
(b) cultivating the recombinant host cell of step (a) under conditions conductive for the production of the DNA methyltransferase; and
(b) optionally, recovering the DNA methyltransferase.

Cultivation of the recombinant host cell and recovering the methyltransferase can be accomplished by standard prior art methods, which are further described herein.

In one embodiment, the DNA methyltransferase recombinantly expressed in the host cell is further characterized as described above. In one embodiment, the expression construct encoding the DNA methyltransferase and the host cell for expressing the DNA methyltransferase are as described above.

In another embodiment, the present invention is directed to a method of producing bacterial transformants, comprising:

(a) introducing into a first bacterial host cell a polynucleotide comprising a polynucleotide sequence encoding a DNA methyltransferase to produce a methylated DNA containing 5-methylcytosine within the recognition sequence GCNGC, wherein the DNA methyltransferase comprises less than 35 amino acid residues between amino acid residue 72 and amino acid residue 106 according to the numbering of SEQ ID NO: 33, as further described herein;
(b) transferring the methylated DNA from the first bacterial host cell into a second bacterial host cell, wherein the second bacterial host cell comprises a restriction endonuclease able to degrade the DNA but unable to degrade the methylated DNA; and
(c) isolating transformants of the second bacterial host cell comprising the methylated DNA.

In one embodiment, the method of producing bacterial transformants comprises the step of introducing a DNA into the first bacterial host cell that shall be methylated by the DNA methyltransferase described herein in the first bacterial host cell. In one embodiment, the method of producing bacterial transformants comprises the step of introducing a DNA into the first bacterial host cell that shall be methylated by the DNA methyltransferase described herein in the first bacterial host cell in order to generate a methylation pattern in the DNA that is not recognized as foreign in the second bacterial host cell.

In one embodiment, the DNA methyltransferase recombinantly expressed in the host cell is further characterized as described above. In one embodiment, the expression construct encoding the DNA methyltransferase and the first and second bacterial host cell are as described above.

In one embodiment, the DNA methyltransferase used in these methods of the present invention methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

In another embodiment, the DNA methyltransferase used in the methods of the present comprises less than 23 amino acid residues between amino acid residue 84 and amino acid residue 106 according to the numbering of SEQ ID NO: 33.

In one embodiment the DNA methyltransferase used in the methods of the present invention methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33.

In one embodiment, the DNA methyltransferase used in the methods of the present comprises less than 11 amino acid residues between amino acid residue 72 and amino acid residue 83 according to the numbering of SEQ ID NO: 33.

Preferably, the DNA methyltransferase used in the methods of the present comprises less than 23 amino acid residues between amino acid residue 84 and amino acid residue 106 according to the numbering of SEQ ID NO: 33.

More preferably, the DNA methyltransferase used in the methods of the present invention methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33.

In one embodiment the DNA methyltransferase used in the methods of the present invention methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 and further comprises less than 23 amino acid residues between amino acid residue 84 and amino acid residue 106 according to the numbering of SEQ ID NO: 33.

In one embodiment the DNA methyltransferase used in the methods of the present invention methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 and further comprises less than 5 amino acid residues between amino acid residue 101 and amino acid residue 106 according to the numbering of SEQ ID NO: 33.

In one embodiment, the DNA methyltransferase further comprises less than 11 amino acid residues between amino acid residue 72 and amino acid residue 83 according to the numbering of SEQ ID NO: 33.

In one embodiment, the DNA methyltransferase used in these methods that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is in one embodiment selected as described in more detail above from the group consisting of:

(a) a DNA methyltransferase having at least 55% identity with SEQ ID NO: 33, 36 or 43;
(b) a DNA methyltransferase encoded by a polynucleotide having at least 70% identity with SEQ ID NO: 19, 25 or 27;
(c) a DNA methyltransferase encoded by a polynucleotide that hybridizes under high stringency conditions with (i) a polynucleotide comprising SEQ ID NO: 19, 25 or 27, or (ii) the full-length complement of (i);
(d) a variant of the DNA methyltransferase of SEQ ID NO: 33, 36 or 43 comprising a substitution, in one embodiment a conservative substitution, deletion, and/or insertion at one or more positions and having DNA methyltransferase activity;
(e) a DNA methyltransferase encoded by a polynucleotide that differs from SEQ ID NO: 19, 25 or 27 due to the degeneracy of the genetic code; and
(f) a fragment of the DNA methyltransferase of (a), (b), (c), (d) or (e) that has DNA methyltransferase activity.

In one embodiment, the DNA methyltransferase used in these methods that methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33 is in one embodiment selected as described in more detail above from the group consisting of:

(a) a DNA methyltransferase having at least 90% identity with SEQ ID NO: 33, 35, 36, 37, 38, 39, 40, 41, 42, or 43;
(b) a DNA methyltransferase encoded by a polynucleotide having at least 80% identity with SEQ ID NO: 18, 19, 20, 21, 24, 25, 26, 27, 28, 29, 30, 31, or 32;
(c) a DNA methyltransferase encoded by a polynucleotide that hybridizes under high stringency conditions with (i) a polynucleotide comprising SEQ ID NO: 18, 19, 20, 21, 24, 25, 26, 27, 28, 29, 30, 31, or 32, or (ii) the full-length complement of (i);
(d) a variant of the DNA methyltransferase of SEQ ID NO: 33, 35, 36, 37, 38, 39, 40, 41, 42, or 43 comprising a substitution, deletion, and/or insertion at one or more positions and having DNA methyltransferase activity;
(e) a DNA methyltransferase encoded by a polynucleotide that differs from SEQ ID NO: 18, 19, 20, 21, 24, 25, 26, 27, 28, 29, 30, 31, or 32 due to the degeneracy of the genetic code; and
(f) a fragment of the DNA methyltransferase of (a), (b), (c), (d) or (e) that has DNA methyltransferase activity.

In one embodiment, the DNA methyltransferase used in these methods of the present invention is a DNA methyltransferase having at least 80%, at least 85%, at least 90%, at least 91%, at least 92%, at least 93%, at least 94%, at least 95%, at least 96%, at least 97%, at least 98%, at least 99% or even 100% sequence identity to an amino acid sequence displayed in SEQ ID NO: 33, 35, 36 or 43, wherein the DNA methyltransferase methylates DNA resulting in a DNA containing 5-methylcytosine within the recognition sequence GCNGC and comprises less than 35 amino acid residues between amino acid residue 72 and amino acid residue 106 according to the numbering of SEQ ID NO: 33.

Preferably, the DNA methyltransferase used in the methods of the present invention that methylates DNA resulting in a DNA containing 5-methylcytosine within the recognition sequence GCNGC comprises less than 23 amino acid residues between amino acid residue 84 and amino acid residue 106 according to the numbering of SEQ ID NO: 33, and preferably selected from the group consisting of:

(a) a DNA methyltransferase having at least 90%, at least 95%, at least 98%, or 100% identity with SEQ ID NO: 33; and
(b) a DNA methyltransferase encoded by a polynucleotide having at least 90%, at least 95%, at least 98%, or 100% identity with SEQ ID NO: 18.

More preferably, the DNA methyltransferase used in the methods of the present invention that methylates DNA resulting in a DNA containing 5-methylcytosine within the recognition sequence GCNGC and comprises less than 5 amino acid residues between amino acid residue 101 and amino acid residue 106 according to the numbering of SEQ ID NO: 33 is selected from the group consisting of:

(a) a DNA methyltransferase having at least 90%, at least 95%, at least 98%, or 100% identity with SEQ ID NO: 33; and
(b) a DNA methyltransferase encoded by a polynucleotide having at least 90%, at least 95%, at least 98%, or 100% identity with SEQ ID NO: 18.

In one embodiment, the DNA methyltransferase used in the methods of the present invention comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, wherein the DNA methyltransferase methylates DNA resulting in a DNA containing 5-methylcytosine within the recognition sequence GCNGC.

In a preferred embodiment, the DNA methyltransferase described herein and used in the methods of the present invention methylates DNA resulting in a DNA containing 5-methylcytosine within the recognition sequence GCNGC and further comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, wherein the DNA methyltransferase comprises 0-4, preferably 2-4, more preferably 3-4, 0, 1, 2, 3, or 4, preferably 4 amino acid residues between amino acid residue 101 and amino acid residue 106 according to the numbering of SEQ ID NO: 33.

In one embodiment, the present invention is directed to a method of producing a DNA methyltransferase, comprising the steps of (a) providing a recombinant host cell comprising a heterologous polynucleotide encoding a DNA methyltransferase wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33, by introducing the polynucleotide into the host cell;
(b) cultivating the recombinant host cell of step (a) under conditions conductive for the production of the DNA methyltransferase; and
(b) optionally, recovering the DNA methyltransferase.

The preferred recombinant host cell for this method is selected from the group consisting of *Escherichia coli, Bacillus subtilis*, and *Bacillus licheniformis.*

In one embodiment, the present invention is directed to a method of producing bacterial transformants, comprising:

(a) introducing into a first bacterial host cell a polynucleotide comprising a polynucleotide sequence encoding a DNA methyltransferase to produce a methylated DNA containing 5-methylcytosine within the recognition sequence GCNGC, wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;
(b) transferring the methylated DNA from the first bacterial host cell into a second bacterial host cell, wherein the second bacterial host cell comprises a restriction endonuclease able to degrade the DNA but unable to degrade the methylated DNA; and
(c) isolating transformants of the second bacterial host cell comprising the methylated DNA.

In a preferred embodiment, the present invention is directed to a method of producing bacterial transformants, comprising:

(a) introducing into a first bacterial host cell a polynucleotide comprising a polynucleotide sequence encoding a DNA methyltransferase to produce a methylated DNA containing 5-methylcytosine within the recognition sequence GCNGC, wherein the DNA methyltransferase methylates DNA resulting in a DNA containing 5-methylcytosine within the recognition sequence GCNGC and wherein the DNA methyltransferase comprises less than 23 amino acid residues between amino acid residue 84 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;
(b) transferring the methylated DNA from the first bacterial host cell into a second bacterial host cell, wherein the second bacterial host cell comprises a restriction endonuclease able to degrade the DNA but unable to degrade the methylated DNA; and
(c) isolating transformants of the second bacterial host cell comprising the methylated DNA.

In a more preferred embodiment, the present invention is directed to a method of producing bacterial transformants, comprising:

(a) introducing into a first bacterial host cell a polynucleotide comprising a polynucleotide sequence encoding a DNA methyltransferase to produce a methylated DNA containing 5-methylcytosine within the recognition sequence GCNGC, wherein the DNA methyltransferase methylates DNA resulting in a DNA containing 5-methylcytosine within the recognition sequence GCNGC and wherein the DNA methyltransferase comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;
(b) transferring the methylated DNA from the first bacterial host cell into a second bacterial host cell, wherein the second bacterial host cell comprises a restriction endonuclease able to degrade the DNA but unable to degrade the methylated DNA; and
(c) isolating transformants of the second bacterial host cell comprising the methylated DNA.

The preferred first host cell for this method is selected from the group consisting of *Escherichia coli*, and *Bacillus subtilis*. Preferred second host cells for this method is *Bacillus licheniformis.*

In a preferred embodiment, the present invention is directed to a method of producing bacterial transformants of *Bacillus licheniformis*, comprising:

(a) introducing into a first bacterial host cell, preferably, selected from *Escherichia coli* and *Bacillus subtilis*, a polynucleotide comprising a polynucleotide sequence encoding a DNA methyltransferase to produce a methylated DNA containing 5-methylcytosine within the recognition sequence GCNGC, wherein the DNA methyltransferase methylates DNA resulting in a DNA containing 5-methylcytosine within the recognition sequence GCNGC and wherein the DNA methyltransferase comprises less than 23 amino acid residues between amino acid residue 84 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;

(b) transferring the methylated DNA from the first bacterial host cell into a second bacterial host cell, wherein the second bacterial host cell is *Bacillus licheniformis* which comprises a restriction endonuclease able to degrade the DNA but unable to degrade the methylated DNA; and (c) isolating transformants of the second bacterial host cell comprising the methylated DNA.

In an even more preferred embodiment, the present invention is directed to a method of producing bacterial transformants of *Bacillus licheniformis*, comprising:

(a) introducing into a first bacterial host cell, preferably, selected from *Escherichia coli* and *Bacillus subtilis*, a polynucleotide comprising a polynucleotide sequence encoding a DNA methyltransferase to produce a methylated DNA containing 5-methylcytosine within the recognition sequence GCNGC, wherein the DNA methyltransferase methylates DNA resulting in a DNA containing 5-methylcytosine within the recognition sequence GCNGC and wherein the DNA methyltransferase comprises less than 5 amino acid residues between amino acid residue 101 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;

(b) transferring the methylated DNA from the first bacterial host cell into a second bacterial host cell, wherein the second bacterial host cell is *Bacillus licheniformis* which comprises a restriction endonuclease able to degrade the DNA but unable to degrade the methylated DNA; and (c) isolating transformants of the second bacterial host cell comprising the methylated DNA.

In one embodiment, the present invention is directed to a method of producing bacterial transformants, comprising:

(a) introducing into a first bacterial host cell a polynucleotide comprising a polynucleotide sequence encoding a DNA methyltransferase and a DNA that shall be methylated by the DNA methyltransferase produce a methylated DNA containing 5-methylcytosine within the recognition sequence GCNGC, wherein the DNA methyltransferase comprises less than 35 amino acid residues between amino acid residue 72 and amino acid residue 106 according to the numbering of SEQ ID NO: 33;

(b) transferring the methylated DNA from the first bacterial host cell into a second bacterial host cell, wherein the second bacterial host cell comprises a restriction endonuclease able to degrade the DNA but unable to degrade the methylated DNA; and (c) isolating transformants of the second bacterial host cell comprising the methylated DNA.

In one embodiment, the present invention is directed to a method of producing bacterial transformants, comprising:

(a) introducing into a first bacterial host cell a polynucleotide comprising a polynucleotide sequence encoding a DNA methyltransferase and a DNA that shall be methylated by the DNA methyltransferase produce a methylated DNA containing 5-methylcytosine within the recognition sequence GCNGC, wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;

(b) transferring the methylated DNA from the first bacterial host cell into a second bacterial host cell, wherein the second bacterial host cell comprises a restriction endonuclease able to degrade the DNA but unable to degrade the methylated DNA; and (c) isolating transformants of the second bacterial host cell comprising the methylated DNA.

In another embodiment, the DNA methyltransferase is native or heterologous to the first bacterial host cell. In one embodiment the DNA methyltransferase is heterologous to the first bacterial host cell.

In another embodiment, the DNA methyltransferase is heterologous to the second bacterial host cell.

In one embodiment, for the method of producing bacterial transformants the second bacterial host cell differs from the first bacterial host cell. In one embodiment, the second bacterial host cell differs from the first bacterial host cell in the restriction modification system, in one embodiment, in that the first bacterial cell does not recognize DNA as foreign, which is recognized as foreign by the second bacterial host cell. In one embodiment, the first bacterial host cell does not comprise a restriction endonuclease that degrades or substantially degrades unmethylated DNA or wherein the restriction endonucleases of the first bacterial host cell cleaves DNA at a sequence that occurs with limited frequency in the DNA, which shall be methylated by the DNA methyltransferase. In one embodiment, the first bacterial host cell does not comprise a restriction endonuclease able to degrade the DNA but unable to degrade the methylated DNA.

The preferred first host cell for this method is selected from *Escherichia coli* and *Bacillus subtilis*. Preferred second host cells for this method is *Bacillus licheniformis.*

In one embodiment, in the first bacterial host cell the uptake of foreign DNA is not limited or not substantially limited by a restriction modification system. This is typically the case, but not limited thereto, in standard *E. coli* or *B. subtilis* cloning hosts. Standard *E. coli* cloning hosts include but are not limited to DH5alpha (Invitrogen), DH10B, (Invitrogen), Omnimax (Invitrogen), INV110 (Invitrogen), TOP10 (Invitrogen), HB101 (Promega), SURE (Stratagene), XL1-Blue (Stratagen), TG1 (Lucigen), and JM109 (NEB). These *E. coli* hosts are defective in the EcoKI restriction-modification systems, some in addition defective in the methylation-dependent restrictases mcrA, mcrB, mcrC, mrr, some in addition defective in dam and dcm DNA-methyltransferases. *Bacillus subtilis* cloning hosts such *B. subtilis* carrying a defective hsd(RI)R-M-locus such as *B. subtilis* IG-20 (BGSC 1A436) or a defective hsdRM1 mutation such as *B. subtilis* 1012 WT (Mobitec).

In one embodiment, for the method of producing bacterial transformants the first bacterial host cell is deficient in producing a DNA methylation pattern that is recognized as foreign by the second bacterial host cell, in one embodiment, the first bacterial host cell is dam and/or dcm methylation deficient. In one embodiment, the first bacterial cell is an *Escherichia coli* cell or a *Bacillus subtilis* cell. In one embodiment, the first bacterial cell is an *Escherichia coli* cell, which is deficient in one or more DNA methyltransferases that methylate adenosine within GATC and/or the second cytosine within CCAGG/CCTGG. In a specific embodiment the first bacterial cell is an *Escherichia coli* cell that is dam- and/or dcm-methylation deficient. In one embodiment, the first bacterial cell is an *Escherichia coli* cell, which is recA positive. In another embodiment the first bacterial cell is an *Escherichia coli* cell that is dam- and/or dcm-methylation deficient and which is recA positive.

In one embodiment, for the method of producing bacterial transformants the second bacterial host cell is a *Bacillus* cell, in a specific embodiment, a *Bacillus licheniformis* cell. In another embodiment, the second bacterial host cell is a *Bacillus licheniformis* cell with a restriction modification system comprising the recognition sequence GCNGC, in a specific embodiment a *Bacillus licheniformis* ATCC 53926 cell.

In one embodiment the second bacterial host cell is a *Bacillus licheniformis* cell and the first bacterial host cell is an *Escherichia coli* or a *Bacillus subtilis* cell. In another embodiment, the first bacterial host cell is *Fusobacterium nucleatum*, in a specific embodiment *Fusobacterium nucleatum* 4HI. In one embodiment, the first bacterial host cell is *Fusobacterium nucleatum*, in a specific embodiment, *Fusobacterium nucleatum* 4HI and the second bacterial host cell is a *Bacillus* cell, in a specific embodiment, *Bacillus licheniformis.*

In one embodiment, the polynucleotide comprising the polynucleotide encoding the DNA methyltransferase is a plasmid DNA. In another embodiment, the polynucleotide comprising the polynucleotide encoding the DNA methyltransferase is integrated into the genome of the first bacterial host cell.

The methylated DNA generated in the first bacterial host cell by the activity of the DNA methyltransferase can be a chromosomal DNA or an extra-chromosomal DNA. In one embodiment, the methylated DNA is a plasmid DNA.

In another embodiment, the present invention is directed to a method of producing methylated DNA with a DNA methyltransferase as described herein. This can be done either in vitro or in vivo. In such embodiment, the present invention is directed to a method for producing a methylated DNA comprising the steps of (a) methylating in vitro or in vivo a DNA with a DNA methyltransferase comprising a methylation recognition sequence GCNGC to produce a methylated DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33; and
(b) isolating the methylated DNA.

Preferably, the present invention is directed to a method of producing methylated DNA with a DNA methyltransferase as described herein. This can be done either in vitro or in vivo. In such embodiment, the present invention is directed to a method for producing a methylated DNA comprising the steps of (a) methylating in vitro or in vivo a DNA with a DNA methyltransferase comprising a methylation recognition sequence GCNGC to produce a methylated DNA containing 5-methylcytosine within the recognition sequence GCNGC and wherein the DNA methyltransferase methylates DNA resulting in a DNA containing 5-methylcytosine within the recognition sequence GCNGC and wherein the DNA methyltransferase comprises less than 23 amino acid residues between amino acid residue 84 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33; and
(b) isolating the methylated DNA.

In one embodiment, the DNA methyltransferase recombinantly used is further characterized as described above. The expression construct encoding the DNA methyltransferase and the host cell for expressing the DNA methyltransferase are in one embodiment as described above.

In one embodiment, the methylated DNA is a chromosomal DNA, in another embodiment fragments of a chromosomal DNA. In yet another embodiment, the methylated DNA is an extra-chromosomal DNA, in specific embodiment, the extra-chromosomal DNA is a plasmid DNA, a viral DNA, or a linear DNA. In one embodiment, the methylated DNA is a DNA comprising a polynucleotide sequence encoding a protein. In another embodiment, the methylated DNA is a DNA that does not comprise a polynucleotide sequence encoding a protein.

The in vitro methylated DNA can also be used for the production of bacterial transformants. Hence, in one embodiment, the present invention is directed to a method of producing bacterial transformants, comprising the steps of (a) methylating in vitro a DNA with a DNA methyltransferase comprising a methylation recognition sequence GCNGC to produce a methylated DNA containing 5-methylcytosine within the recognition sequence GCNGC, and wherein the DNA methyltransferase comprises less than 35 amino acid residues between amino acid residue 72 and amino acid residue 106 according to the numbering of SEQ ID NO: 33;
(b) introducing the methylated DNA into a bacterial host cell, wherein the bacterial host cell comprises a restriction endonuclease able to degrade the DNA but unable to degrade the methylated DNA; and
(c) isolating transformants of the bacterial host cell comprising the methylated DNA.

The in vitro methylated DNA can also be used for the production of bacterial transformants. Hence, in one embodiment, the present invention is directed to a method of producing bacterial transformants, comprising the steps of (a) methylating in vitro a DNA with a DNA methyltransferase comprising a methylation recognition sequence GCNGC to produce a methylated DNA containing 5-methylcytosine within the recognition sequence GCNGC, and wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33;
(b) introducing the methylated DNA into a bacterial host cell, wherein the bacterial host cell comprises a restriction endonuclease able to degrade the DNA but unable to degrade the methylated DNA; and
(c) isolating transformants of the bacterial host cell comprising the methylated DNA.

In one embodiment, the DNA methyltransferase is heterologous to the bacterial host cell.

In one embodiment, the DNA methyltransferase used is further characterized as described above. The expression construct encoding the DNA methyltransferase and the host cell for expressing the DNA methyltransferase are in one embodiment as described above.

In another embodiment, the present invention is directed to the use of a methylated DNA for improving the transformation efficiency of the DNA in a bacterial host cell. In one embodiment, the present invention is directed to the use of a methylated DNA obtained by any of the methods described herein using the DNA methyltransferase as described herein for improving the transformation efficiency of the DNA in a bacterial host cell.

Thus, in one embodiment, the present invention is directed to the use of a methylated DNA obtained by a method comprising the steps of (a) methylating in vitro or in vivo a DNA within the recognition sequence GCNGC with a DNA methyltransferase comprising a methylation recognition sequence GCNGC to produce a methylated DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33; and
(b) isolating the methylated DNA;

for improving the transformation efficiency of the DNA in a bacterial host cell, in one embodiment further, comprising the steps of (c) introducing the methylated DNA into a bacterial host cell, wherein the bacterial host cell comprises a restriction endonuclease able to degrade the DNA but unable to degrade the methylated DNA; and optionally
(d) isolating transformants of the bacterial host cell comprising the methylated DNA.

Thus, in one embodiment, the present invention is directed to the use of a methylated DNA obtained by a method comprising the steps of (a) methylating in vitro or in vivo a DNA within the recognition sequence GCNGC with a DNA methyltransferase comprising a methylation recognition sequence GCNGC to produce a methylated DNA containing 5-methylcytosine within the recognition sequence GCNGC and wherein the DNA methyltransferase methylates DNA resulting in a DNA containing 5-methylcytosine within the recognition sequence GCNGC and wherein the DNA methyltransferase comprises less than 35 amino acid residues between amino acid residue 72 and amino acid residue 106 according to the numbering of SEQ ID NO: 33 and is a DNA methyltransferase having at least 80%, at least 85%, at least 90%, at least 91%, at least 92%, at least 93%, at least 94%, at least 95%, at least 96%, at least 97%, at least 98%, at least 99% or 100% sequence identity to an amino acid sequence displayed in SEQ ID NO: 33; and
(b) isolating the methylated DNA;

for improving the transformation efficiency of the DNA in a bacterial host cell, in one embodiment further, comprising the steps of (c) introducing the methylated DNA into a bacterial host cell, wherein the bacterial host cell comprises a restriction endonuclease able to degrade the DNA but unable to degrade the methylated DNA; and optionally
(d) isolating transformants of the bacterial host cell comprising the methylated DNA.

The preferred host cell for this method is *Bacillus licheniformis.*

Protein of Interest

The recombinant host cells created by the methods described herein are particularly useful as host cells for the expression of polynucleotides native or foreign to the cells. Therefore, the present invention is also directed to a method of cultivating a transformant obtained by any of the methods described herein and using the DNA methyltransferase as described herein. In a particular embodiment, the present invention is further directed to methods of expressing a heterologous polynucleotide comprising: (a) cultivating the recombinant cell under conditions conducive for expression of the heterologous polynucleotide; and (b) optionally recovering a polypeptide encoded by the polynucleotide.

In a particular embodiment, the present invention is further directed to methods of producing a native or foreign polypeptide comprising: (a) cultivating the recombinant cell under conditions conducive for production of the polypeptide; and (b) optionally recovering the polypeptide.

Thus, the present invention is also directed to a method for producing a heterologous protein of interest in a bacterial cell comprising the step of cultivating the isolated transformant of the second bacterial host cell obtained by any of the methods described herein for a time and under conditions sufficient to produce the heterologous protein. In one embodiment, the heterologous protein of interest is encoded by the methylated DNA obtained by any of the methods described herein.

In a further embodiment the present invention is directed to a method for producing a heterologous protein of interest in a bacterial cell comprising the steps (a) methylating in vitro or in vivo a DNA with a DNA methyltransferase comprising a methylation recognition sequence GCNGC to produce a methylated DNA containing 5-methylcytosine within the recognition sequence GCNGC, and wherein the DNA methyltransferase comprises less than 35 amino acid residues between amino acid residue 72 and amino acid residue 106 according to the numbering of SEQ ID NO: 33;
(b) isolating the methylated DNA;
(c) introducing the methylated DNA into a bacterial host cell, in one embodiment wherein the bacterial host cell comprises a restriction endonuclease able to degrade the DNA but unable to degrade the methylated DNA;
(d) isolating transformants of the bacterial host cell comprising the methylated DNA;
(e) cultivating one or more of the isolated transformants of the bacterial host cell for a time and under conditions sufficient to produce the heterologous protein;

wherein the heterologous protein is encoded by a polynucleotide comprised in the methylated DNA or by a polynucleotide separate from the methylated DNA. In one embodiment the heterologous protein of interest is encoded by the methylated DNA.

The bacterial host cells are cultivated in a nutrient medium suitable for production of a polypeptide of interest using methods known in the art. For example, the cell may be cultivated by shake flask cultivation, small-scale or largescale fermentation (including continuous, batch, fed-batch, or solid state fermentations) in laboratory or industrial fermenters performed in a suitable medium and under conditions allowing the polypeptide of interest to be expressed and/or isolated. In one embodiment, the cultivation of the bacterial host cell is by fermentation in industrial scale. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The protein of interest can accumulate in the cell or can be secreted outside of the cell. The secreted polypeptide of interest can be recovered directly from the medium. The polypeptide of interest may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), Enzyme Handbook, Springer-Verlag, New York, 1990). Assays for determining activity of a restriction endonuclease or DNA methyltransferase are described herein.

The resulting protein of interest may be isolated by methods known in the art. For example, a protein of interest may be isolated from the fermentation broth by conventional procedures including, but not limited to, centrifugation, filtration, extraction, spray-drying, evaporation, or precipitation. Depending on the expression construct used, the protein of interest can be secreted into the fermentation broth or can remain inside the host cell. In case of the latter, the protein of interest can be recovered from the fermentation broth by applying a step where the cells are lysed. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). The purified polypeptide may then be concentrated by procedures known in the art including, but not limited to, ultrafiltration and evaporation, in particular, thin film evaporation. In another embodiment, the protein of interest is not purified from the fermentation broth. In a specific embodiment, the protein of interest is not secreted in the fermentation broth and not recovered from the fermentation broth.

In one embodiment, the protein of interest is an enzyme. The enzyme may be, but is not limited to, a detergent enzyme and an enzyme suitable for human and/or animal nutrition. In one embodiment, the enzyme is classified as an oxidoreductase (EC 1), a transferase (EC 2), a hydrolase (EC 3), a lyase (EC 4), an isomerase (EC 5), or a Ligase (EC 6) (EC-numbering according to Enzyme Nomenclature, Recommendations (1992) of the Nomenclature Committee of the International Union of Biochemistry and Molecular Biology including its supplements published 1993-1999). In one embodiment, the protein of interest is a protein conferring resistance to antibiotics to a host cell.

In another embodiment, the enzyme is a hydrolase (EC 3), in one embodiment a glycosidase (EC 3.2) or a peptidase (EC 3.4). In one embodiment, enzymes selected from the group consisting of an amylase (in particular an alpha-amylase (EC 3.2.1.1)), a cellulase (EC 3.2.1.4), a lactase (EC 3.2.1.108), a mannanase (EC 3.2.1.25), a lipase, a phytase (EC 3.1.3.8), and a protease. In one embodiment, the enzyme is selected from the group consisting of oxidoreductase, transferase, hydrolase, lyase, isomerase, ligase, aminopeptidase, amylase, asparaginase, carbohydrase, carboxypeptidase, catalase, cellulase, chitinase, cutinase, cyclodextrin glycosyltransferase, deoxyribonuclease, esterase, alpha-galactosidase, betagalactosidase, glucoamylase, alpha-glucosidase, beta-glucosidase, hyaluronic acid synthase, invertase, laccase, lipase, mannosidase, mutanase, oxidase, a pectinolytic enzyme, peroxidase, phytase, polyphenoloxidase, protease, ribonuclease, transglutaminase, and orxylanase. In particular an enzyme selected from the group consisting of amylase, protease, lipase, mannanase, phytase, and cellulase, in a specific embodiment amylase or protease, in one embodiment, a serine protease (EC 3.4.21). In another embodiment the enzyme is a subtilisin protease.

EXAMPLES

The following examples only serve to illustrate the invention. The numerous possible variations that are obvious to a person skilled in the art also fall within the scope of the invention.

Unless otherwise stated the following experiments have been performed by applying standard equipment, methods, chemicals, and biochemicals as used in genetic engineering and fermentative production of chemical compounds by cultivation of microorganisms. See also Sambrook et al. (Sambrook, J. and Russell, D. W. Molecular cloning. A laboratory manual, 3rd ed, Cold Spring Harbor Laboratory Press, Cold Spring Harbor, N.Y. 2001) and Chmiel et al. (Bioprocesstechnik 1. Einfuhrung in die Bioverfahrenstechnik, Gustav Fischer Verlag, Stuttgart, 1991).

Electrocompetent *Bacillus licheniformis* Cells and Electroporation

Transformation of DNA into *B. licheniformis* ATCC 53926 s performed via electroporation. Preparation of electrocompetent *B. licheniformis* ATCC 53926 cells and transformation of DNA is performed as essentially described by Brigidi et al (Brigidi, P., Mateuzzi, D. (1991). Biotechnol. Techniques 5, 5) with the following modification: Upon transformation of DNA, cells are recovered in 1 ml LBSPG buffer and incubated for 60 min at 37° C. (Vehmaanpera J., 1989, FEMS Microbio. Lett., 61: 165-170) following plating on selective LB-agar plates. If not stated differently, DNA foreign to DNA from *B. licheniformis* ATCC 53926, is in vitro methylated according to the method as described in patent DE4005025.

Plasmid Isolation

Plasmid DNA was isolated from *Bacillus* and *E. coli* cells by standard molecular biology methods described in (Sambrook, J. and Russell, D. W. Molecular cloning. A laboratory manual, 3rd ed, Cold Spring Harbor Laboratory Press, Cold Spring Harbor, N.Y. 2001) or the alkaline lysis method (Birnboim, H. C., Doly, J. (1979). Nucleic Acids Res 7(6): 1513-1523). *Bacillus* cells were in comparison to *E. coli* treated with 10 mg/ml lysozyme for 30 min at 37° C. prior to cell lysis.

Plasmids

Plasmid pUK56 and pUK56S: Protease Expression Plasmid

The protease expression cassette of plasmid pCB56C (U.S. Pat. No. 5,352,604) was PCR-amplified with oligonucleotides SEQ ID NO: 1 and SEQ ID NO: 2 and the pUB110 plasmid backbone comprising repU and the kanamycin resistance gene was PCR-amplified with oligonucleotides SEQ ID NO: 3 and SEQ ID NO: 4. The PCR fragments were cut with restriction enzymes SacI and SnabI, ligated with T4-DNA ligase (NEB) following transformation into *Bacillus subtilis* 168 competent cells according to the protocol of Spizizen (Anagnostopoulos, C. and Spizizen, J. (1961). J. Bacteriol. 81, 741-746.) Correct clones of final plasmid pUK56 were analyzed be restriction enzyme digest and sequencing. The plasmid pUK56 was cut with SnaBI and the fragment of pBR322 was PCR-amplified with oligonucleotides SEQ ID NO: 5 and SEQ ID NO: 6 cut with SnabI/EcoRV (accession number pBR322 J01749.1), and cloned into pUK56 following transformation into *E. coli* XL1-Blue competent cells (Stratagene). The *E. coli/Bacillus* shuttle plasmid pUK56S with a functional SnaBI RE sites was recovered.

Plasmid pLCS3: Expression Plasmid

The low-copy origin of replication pSC101 from plasmid pZS4-Int-1 (Lutz, R. and Bujard, H. (1997); Nucleic Acids Res. 25, 1203-1210; accession number U66308) was recovered by digestion with restriction endonucleases XbaI and ScaI and cloned into pZA3PLtetO-1 luc (accession number U66309) cut with restriction endonucleases ScaI and AvrII to replace the replication origin yielding plasmid pLCS3.

Plasmid pLCS4: Expression Plasmid

The kanamycin resistance gene fragment (SacI/XhoI) from pZE2 PLtetO-1 MCS2 (Lutz, R. and Bujard, H. (1997); Nucleic Acids Res. 25, 1203-1210; gene accession number U66312) was cloned into pLCS3 cut with restriction endonucleases SacI/XhoI to replace the chloramphenicol resistance gene yielding plasmid pLCS4.

Plasmid pEDS3: Expression Plasmid

The synthetic DNA fragment comprising a fragment of the control region of the secA gene from *B. licheniformis* (SEQ ID NO: 9), T0 lambda terminator (Stueber, D. and Bujard, H. (1982), EMBO J. 1, 1399-1404) comprising two BsaI RE sites, flanked by XhoI and XbaI (SEQ ID NO: 10) restriction sites was cloned into pLCS3 plasmid cut with XhoI and XbaI yielding plasmid pEDS3.

Plasmid pMDS001-006: DNA-Methyltransferase Gene Expression Constructs

The genes for the DNA-Methyltransferases were ordered as synthetic gene fragments comprising the 5'UTR/RBS of the secA gene from *B. licheniformis* (SEQ ID NO: 13), the coding sequence (cds) for the MTase gene (see sequence listing), flanked by BsaI restriction sites with compatible overhangs upon restriction for subsequent cloning into plasmid pEDS3. Internal BsaI restriction sites were removed by variation of the codon-triplet.

TABLE 1

DNA-Methyltransferase expression constructs

| MTase polynucleotide (SEQ ID NO:) | Destination plasmid | MTase plasmid |
|---|---|---|
| SEQ ID NO: 22 | pEDS3 | pMDS001 |
| SEQ ID NO: 23 | pEDS3 | pMDS002 |
| SEQ ID NO: 19 | pEDS3 | pMDS003 |
| SEQ ID NO: 25 | pEDS3 | pMDS004 |
| SEQ ID NO: 27 | pEDS3 | pMDS005 |
| SEQ ID NO: 24 | pEDS3 | pMDS006 |

Plasmid pBIL009: *Bacillus subtilis* Integration Plasmid

The plasmid pBS1C amyE integration plasmid (Radeck, J. et al. (2013). J. Biol. Eng 7, 29) for *B. subtilis* was amplified by PCR with oligonucleotides SEQ ID NO: 14 and SEQ ID NO: 15 restricted with BsaI following cloning into the pLCS4 plasmid backbone comprising pSC101 replication origin and the kanamycin resistance gene recovered as XbaI/XhoI restriction digest fragment. The ligation mixture was transformed into *E. coli* XL1-Blue cells (Stratagene) and clones recovered on LB-agar plates containing 20 μg/ml Kanamycin. Positive clones yielding plasmid pBIL009 were analyzed by restriction digest and functional chloramphenicol resistance gene.

Plasmid pMIS012: DNA-Methyltransferase—*B. subtilis* Gene Expression Construct

The DNA-methyltransferase expression construct of pMDS003 was PCR-amplified with oligonucleotides SEQ ID NO: 16 and SEQ ID NO: 17 restricted with BamHI/XbaI following cloning into the pBIL009 plasmid backbone recovered as BamHI/XbaI restriction digest fragment. The ligation mixture was transformed into *E. coli* XL1-Blue cells (Stratagene) and clones recovered on LB-agar plates containing 20 μg/ml Kanamycin. Positive clones yielding plasmid pMIS012 were analyzed by restriction digest and functional chloramphenicol resistance gene.

Structure Prediction

Structures for the methyltransferases were predicted using the homology modelling toolkit SWISS-MODEL (Biasini M., Bienert S., Waterhouse A., Arnold K., Studer G., Schmidt T., Kiefer F., Cassarino T. G., Bertoni M., Bordoli L., Schwede T. (2014). SWISS-MODEL: modelling protein tertiary and quaternary structure using evolutionary information Nucleic Acids Research 2014 (1 Jul. 2014) 42 (W1): W252-W258) using default parameters and the following structural templates from the RCSB PDB database (Berman H. M., Westbrook J., Feng Z., Gilliland G., Bhat T. N., Weissig H., Shindyalov I. N., Bourne P. E. (2000) The Protein Data Bank Nucleic Acids Research, 28: 235-242): 2uyc_A (used for SEQ ID NO: 33 (M_Fnu4HI), SEQ ID NO: 34 (M_RBH3250), SEQ ID NO: 41 (M_CocII)), 2i9k_C (used for SEQ ID NO: 36 (M_Bsp6I), SEQ ID NO: 43 (M_LlaDII)), 3swr_A (used for SEQ ID NO: 37 (M_Cdi13307II), SEQ ID NO: 38 (M_Cdi630IV)), 1mht_C (used for SEQ ID NO: 39 (M_Ckr177III)), 2z6u_A (used for SEQ ID NO: 40 (M_CmaLM2II)) and 9mht_C (used for SEQ ID NO: 42 (M_Fsp4HI)).

Structural Alignment

Predicted structures were structurally aligned to the predicted structure of SEQ ID NO: 33 (M_Fnu4HI) with TMalign, version 20160521 (Y. Zhang, J. Skolnick (2005), TM-align: A protein structure alignment algorithm based on TM-score, Nucleic Acids Research, 33: 2302-2309) using the default parameters.

Structure-Based Multiple Sequence Alignment

Pairwise structural alignments were combined into a multiple sequence alignment using MAFFT, version 7.221 (Katoh, S. (2013) MAFFT multiple sequence alignment software version 7: improvements in performance and usability. Molecular Biology and Evolution 30:772-780) using default parameters of the merge mode. Secondary structure annotation was added to the figure as a consensus of structural predictions.

Sequence Selection

All DNA (cytosine-5)-methyltransferases with a recognition sequence of GCNGC and that were experimentally verified with a state-of-the-art technique (determined by having 'PacBio' in their comments field) were extracted from REBASE (Roberts R J, Vincze T, Posfai J, Macelis D (2015) REBASE-a database for DNA restriction and modification: enzymes, genes and genomes. Nucleic Acids Research 43: D298-D299). To this set of methyltransferases, sequences were added for which in-house data (M.Fnu4HI and M.RBH03250) or data from literature (M.Fsp4HI (Chmuzh, E. V. and Degtiarev, S. K., 2007, Mol. Biol. (Mosk) 41, 43-50), M.Bsp6I (Lubys et al., 1995, Gene 157: 25-29), M.LlaDII (Madsen et al., 1995, Applied and Environmental Microbiology, 64(7): 2424-2431)) confirm the recognition sequences.

Example 1

Generation of Methylated DNA In Vivo in *E. coli* Cells

Competent *E. coli* INV110 cells (Invitrogen/Life technologies) were transformed with plasmid pUK65S and selected on LB-plates with 20 μg/ml Kanamycin yielding *E. coli* strain Ec #082. *E. coli* strain Ec #082 was made competent according to the method of Chung (Chung, C. T., Niemela, S. L., and Miller, R. H. (1989). One-step preparation of competent *Escherichia coli*: transformation and storage of bacterial cells in the same solution. Proc. Natl. Acad. Sci. U.S.A 86, 2172-2175) and transformed with DNA-methyltransferase encoding expression plasmids (Table 1) following selection on LB-agar plates containing 20 μg/ml kanamycin and 30 μg/ml chloramphenicol. MTase expression plasmids were constructed as described above (Table 1). *E coli* strain name, Plasmid names and MTase genes are indicated.

TABLE 2

| *E. coli* Name | Plasmids | MTase polynucleotide (SEQ ID NO) |
|---|---|---|
| Ec#082 | pUK56S | — |
| Ec#083 | pUK56S, pMDS001 | 22 |
| Ec#084 | pUK56S, pMDS002 | 23 |
| Ec#085 | pUK56S, pMDS003 | 19 |
| Ec#086 | pUK56S, pMDS004 | 25 |
| Ec#087 | pUK56S, pMDS005 | 27 |
| Ec#088 | pUK56S, pMDS006 | 24 |

Figure 2:
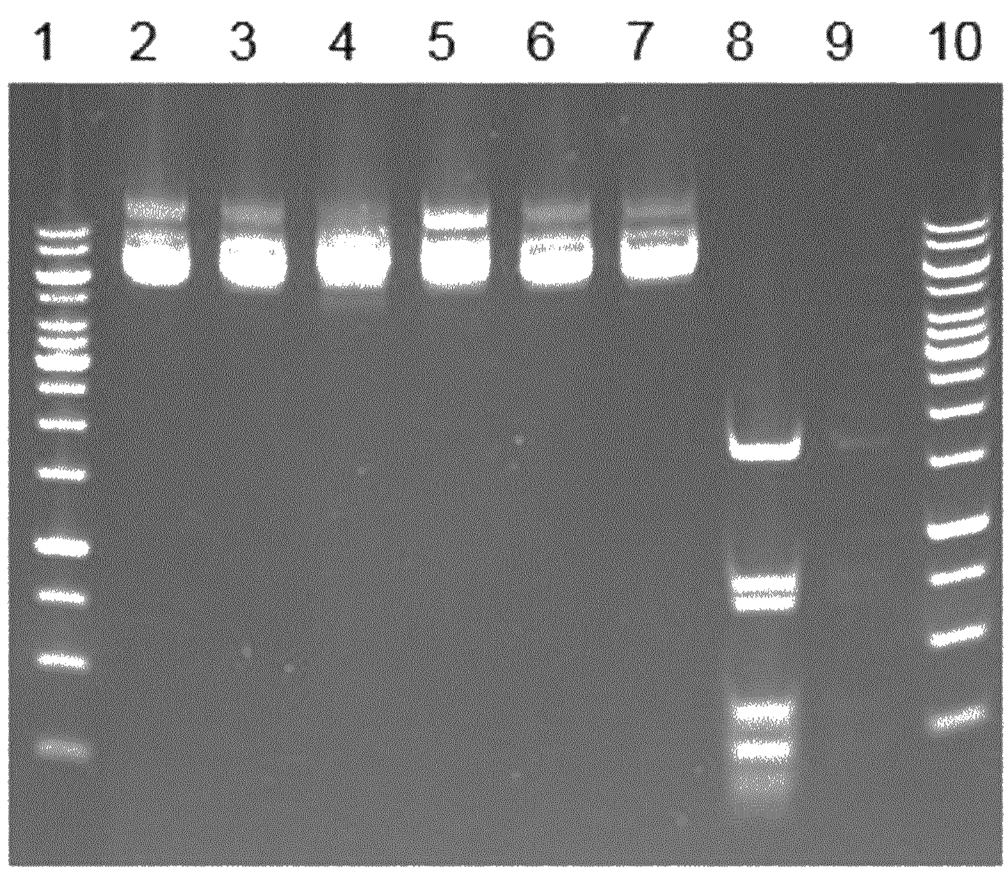
FIG. 2 shows a 0.8% agarose gel of a SatI restriction digests of plasmids isolated from different MTase containing *E. coli* strains (Example 1). Lane 1: DNA marker—Generuler 1 kb DNA Ladder (ThermoFisher Scientific). Lane 2: Ec #83, Lane 3: Ec #84, Lane 4: Ec #85, Lane 5: Ec #86, Lane 6: Ec #87, Lane 7: Ec #88. Lane 8: Ec #82. Lane 10: DNA marker.

Total plasmid DNA was isolated from the different *E. coli* strains according to standard methods in molecular biology (Sambrook, J. and Russell, D. W. Molecular cloning. A laboratory manual, 3rd ed, Cold Spring Harbor Laboratory Press, Cold Spring Harbor, N.Y. 2001) and the efficiency of in vivo methylation determined by restriction of 1 μg plasmid DNA with SatI (ThermoFisher Scientific) which is inhibited from cleavage by 5-methylcytosine within the recognition sequence GCNGC. Restriction reactions were analyzed by agarose gel electrophoresis with ethidium bromide staining for visualization. The Generuler 1 kb DNA Ladder (ThermoFisher Scientific) was used for estimation of DNA fragment size (FIG. 2). Plasmid DNA isolated from *E. coli* strains with GCNGC specific 5-methylcytosine DNA methylation is protected from restriction by SatI, whereas pUK56S from *E. coli* strain Ec #082 is not.

Example 2

Transformation of Methylated DNA from *E. coli* Cells into *Bacillus licheniformis.*

Figure 3:
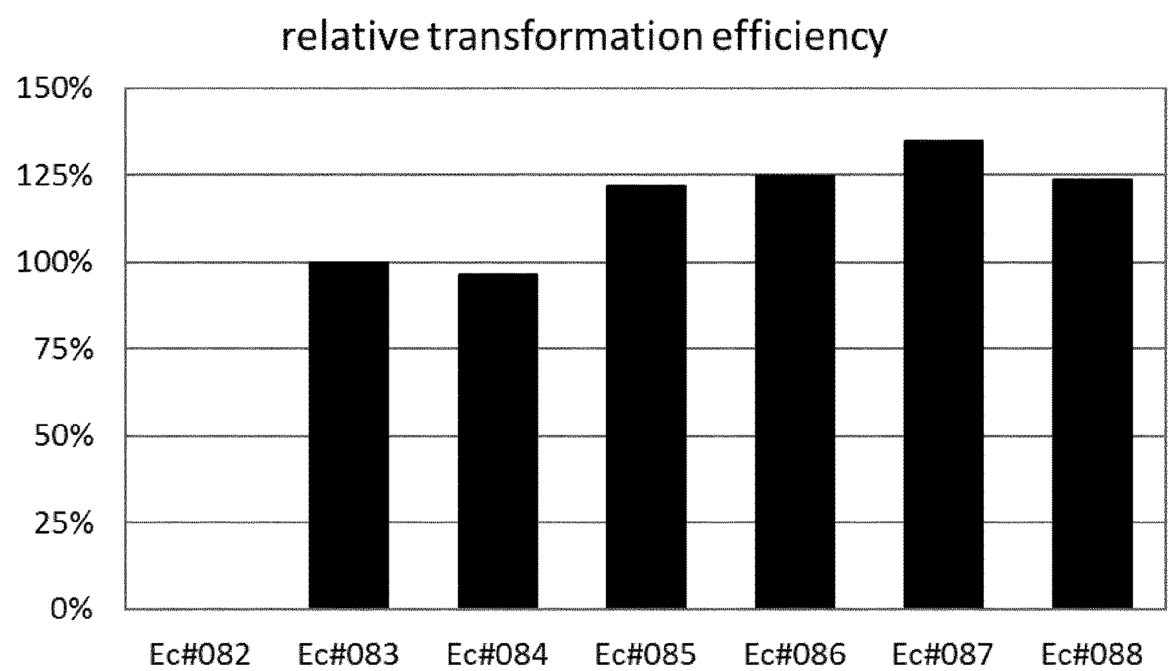
FIG. 3 shows the relative transformation efficiencies into *B. licheniformis* ATCC 53926 cells of plasmid DNA isolated from different *E. coli* strains as described in Example 2. The *E. coli* strain Ec #083 carries the *B. licheniformis* ATCC 53926 DNA methyltransferase and was set to 100%. The *E. coli* strain Ec #084 carries a codon-optimized variant of the *B. licheniformis* ATCC 53926 DNA methyltransferase and serves as control for gene expression. Plasmid DNA from *E. coli* Ec #082 which was not methylated by a GCNGC specific DNA methyltransferase did not recover any transformants. Plasmid DNA isolated from *E. coli* strains carrying MTases having a similar structure and being heterologous to *B. licheniformis* ATCC 53926 (Ec #85-87) transformed into *B. licheniformis* ATCC 53926 resulted in significantly increased transformation efficiencies. Plasmid DNA isolated from the *E. coli* strain carrying the homologous MTase (Ec #88) of *B. licheniformis* ATCC 53926 with a deletion of amino acids 103-108 from SEQ ID NO: 34 (6 amino acids were truncated in total, resulting in SEQ ID NO: 35) also resulted in a significantly increased transformation efficiency compared to Ec #83.

Plasmid DNA was isolated from *E. coli* cells Ec #082-Ec #088 as described in Example 1 and 1 μg plasmid DNA transformed into *B. licheniformis* ATCC 53926 electrocompetent cells as essentially described by Brigidi et al (Brigidi, P., Mateuzzi, D. (1991). Biotechnol. Techniques 5, 5) with the following modification: Upon transformation of DNA, cells are recovered in 1 ml LBSPG-buffer and incubated for 60 min at 37° C. (Vehmaanpera J., 1989, FEMS Microbio. Lett., 61: 165-170) following plating on LB-agar plates containing 20 μg/ml Kanamycin. LB-agar plates are incubated overnight at 37° C. and the transformation efficiency as colony-forming-units (cfu) determined. The transformation efficiencies of plasmid DNA from different *E. coli* strains were normalized against *E. coli* strain Ec #083 which was set to 100%. Note, the *E. coli* strain Ec #083 carries the *B. licheniformis* ATCC 53926 DNA methyltransferase. The *E. coli* strain Ec #084 carries a codon-optimized variant of the *B. licheniformis* ATCC 53926 DNA methyltransferase and serves as control for gene expression. Plasmid DNA pUK56S from *E. coli* Ec #082 which was not methylated by a GCNGC specific DNA methyltransferase did not recover any transformants. Surprisingly, plasmid DNA isolated from *E. coli* strains carrying MTases (Ec #85-87) heterologous to *B. licheniformis* ATCC 53926 transformed into *B. licheniformis* ATCC 53926 resulted in significantly increased transformation efficiencies (FIG. 3). Moreover, plasmid DNA isolated from the *E. coli* strain carrying the homologous MTase (Ec #88) of *B. licheniformis* ATCC 53926 with a deletion of amino acids 103-108 from SEQ ID NO: 34 (6 amino acids were truncated in total, resulting in SEQ ID NO: 35) also resulted in a significantly increased transformation efficiency compared to Ec #83.

Example 3

In Vivo Methylation in *B. subtilis.*

The MTase expression plasmid pMIS012 for integration into the amyE gene of *B. subtilis* was linearized with restriction enzyme SacI following transformation of 2 μg of linearized plasmid DNA into *B. subtilis* 168 cells made competent according to the method of Spizizen (Anagnostopoulos, C. and Spizizen, J. (1961). J. Bacteriol. 81, 741-746). Cells were spread and incubated overnight at 37° C. on LB-agar plates containing 10 μg/ml chloramphenicol. Grown colonies were picked and stroke on both LB-agar plates containing 10 μg/ml chloramphenicol and LB-agar plates containing 10 μg/ml chloramphenicol and 0.5% soluble starch (Sigma) following incubation overnight at 37° C. The starch plates were covered with iodine containing Lugols solution and positive integration clones identified with negative amylase activity. Genomic DNA of positive clones was isolated by standard phenol/chlorform extraction methods after 30 min treatment with lysozyme (10 mg/ml) at 37° C., following analysis of correct integration of the MTase expression cassette by PCR. The resulting *B. subtilis* strain is named Bs #053.

Figure 4:
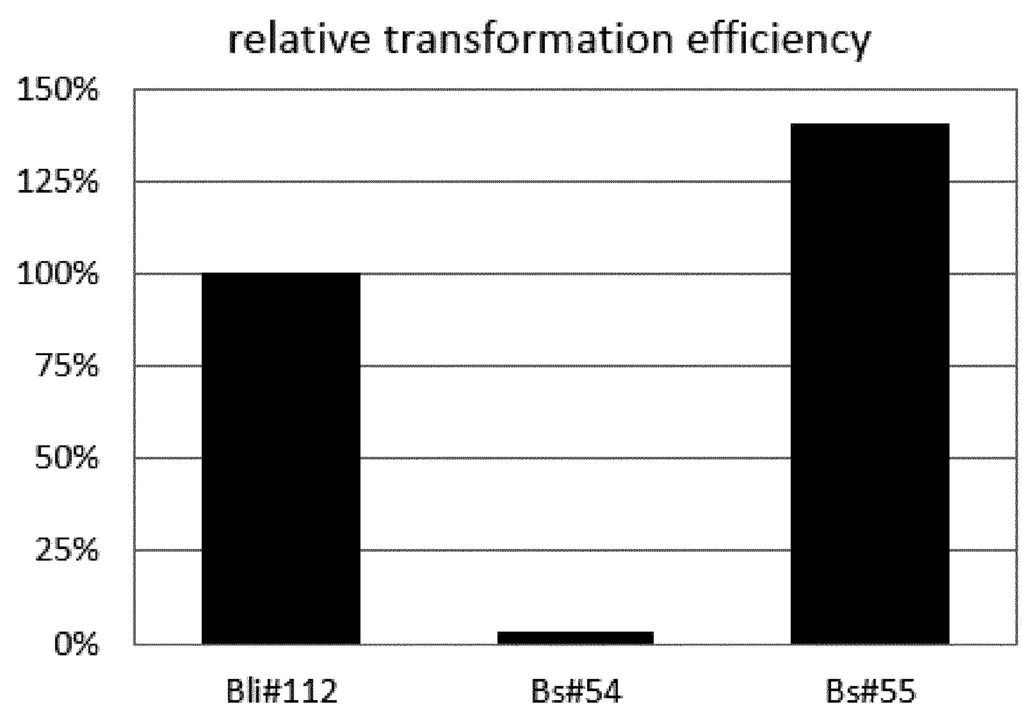
FIG. 4 shows the relative transformation efficiencies into *B. licheniformis* ATCC 53926 cells of pUK56 plasmid DNA isolated from *B. subtilis* Bs #54 and Bs #55 strains as described in Example 3. The transformation efficiency of pUK56 plasmid DNA isolated from *B. licheniformis* Bli #112, carrying the *B. licheniformis* ATCC 53926 DNA methylation pattern, was set to 100%.

Plasmid pUK56 was transformed into *B. subtilis* 168 and *B. subtilis* Bs #053 cells made competent according to the method of Spizizen (Anagnostopoulos, C. and Spizizen, J. (1961). J. Bacteriol. 81, 741-746). The plasmid DNA pUK56 was in vitro methylated as described in patent DE4005025 following transformation into *B. licheniformis* ATCC 53926 electrocompetent cells as described in Example 2. Transformants were spread and incubated overnight at 37° C. on LB-agar plates containing 20 μg/ml kanamycin and 1% skim milk generating *B. subtilis* strains Bs #54 and Bs #55 and *B. licheniformis* strain Bli #112 respectively. Plasmid DNA pUK56 was isolated from *B. subtilis* strains Bs #54 and Bs #55 and *B. licheniformis* strain Bli #112 as described in Example 1 after 30 min treatment with lysozyme (10 mg/ml) at 37° C. 1 μg plasmid DNA each was transformed into *B. licheniformis* ATCC 53926 electrocompetent cells as described in Example 2. The transformation efficiencies of plasmid pUK56 from *B. subtilis* Bs #54 and Bs #55 were normalized against the transformation efficiency of plasmid pUK56 isolated from *B. licheniformis* Bli #112 which was set to 100%. Surprisingly, plasmid DNA pUK56 isolated from *B. subtilis* Bs #55, carrying a MTase heterologous to *B. licheniformis* ATCC 53926, in comparison to plasmid DNA pUK56 isolated from *B. licheniformis* Bli #112, carrying the native *B. licheniformis* ATCC 53926 DNA methylation pattern, resulted in a significantly increased transformation efficiency (FIG. 4). In contrast, almost no colonies were recovered after transformation of plasmid pUK56 from *B. subtilis* Bs #54, which served as control.

The invention claimed is:

1. A method for producing a methylated DNA comprising the steps of (a) methylating in vitro or in vivo a DNA with a DNA methyltransferase comprising a methylation recognition sequence GCNGC to produce a methylated DNA containing 5-methylcytosine within the recognition sequence GCNGC, wherein the DNA methyltransferase comprises less than 35 amino acid residues between amino acid residue 72 and amino acid residue 106 according to the numbering of SEQ ID NO: 33; and (b) isolating the methylated DNA.

2. The method of claim 1, wherein the DNA methyltransferase comprises less than 23 amino acid residues between amino acid residue 84 and amino acid residue 106 according to the numbering of SEQ ID NO: 33.

3. The method of claim 1, wherein the DNA methyltransferase comprises less than 5 amino acid residues between amino acid residue 101 and amino acid residue 106 according to the numbering of SEQ ID NO: 33.

4. The method of any of claim 1, wherein the DNA methyltransferase comprises less than 11 amino acid residues between amino acid residue 72 and amino acid residue 83 according to the numbering of SEQ ID NO: 33.

5. The method of claim 1, wherein the DNA methyltransferase is selected from the group consisting of: (a) a DNA methyltransferase having at least 55% identity with SEQ ID NO: 33 and (b) a DNA methyltransferase encoded by a polynucleotide having at least 70% identity with SEQ ID NO: 19.

* * * * *